(12) United States Patent
Yang et al.

(10) Patent No.: US 7,553,846 B2
(45) Date of Patent: Jun. 30, 2009

(54) 2-ALKYLBENZOXAZOLE CARBOXAMIDES AS 5-HT$_3$ MODULATORS

(75) Inventors: Zhicai Yang, Schenectady, NY (US); David D. Manning, Duanesburg, NY (US)

(73) Assignee: Albany Molecular Research, Inc., Albany, NY (US)

( * ) Notice: Subject to any disclaimer, the term of this patent is extended or adjusted under 35 U.S.C. 154(b) by 21 days.

(21) Appl. No.: 11/834,909

(22) Filed: Aug. 7, 2007

(65) Prior Publication Data

US 2008/0214601 A1 Sep. 4, 2008

Related U.S. Application Data

(60) Provisional application No. 60/821,650, filed on Aug. 7, 2006.

(51) Int. Cl.
*A01N 43/42* (2006.01)
*A61K 31/44* (2006.01)
*A01N 43/90* (2006.01)
*C07D 453/02* (2006.01)

(52) U.S. Cl. .................. 514/299; 514/305; 546/133; 546/183

(58) Field of Classification Search .................. 514/299, 514/305; 546/133, 183
See application file for complete search history.

(56) References Cited

U.S. PATENT DOCUMENTS

| 5,260,303 | A | 11/1993 | Becker et al. |
| 5,631,257 | A | 5/1997 | Iwamatsu et al. |
| 6,353,010 | B1 * | 3/2002 | Dyke et al. .................. 514/367 |

FOREIGN PATENT DOCUMENTS

| EP | 0621271 A1 | 10/1994 |
| EP | 0975327 B1 | 2/2000 |
| WO | WO2003037896 A1 | 5/2003 |
| WO | WO2006089100 A1 | 8/2006 |

OTHER PUBLICATIONS

PCT International Search Report for PCT/US2007/075355 dated Feb. 7, 2008.
PCT International Search Report for PCT/US2007/075378 dated Feb. 26, 2008.

* cited by examiner

*Primary Examiner*—D. Margaret Seaman
*Assistant Examiner*—Niloofar Rahmani
(74) *Attorney, Agent, or Firm*—Heslin Rothenberg Farley & Mesiti P.C.

(57) ABSTRACT

Compounds of formulae I and II:

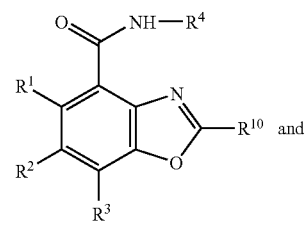

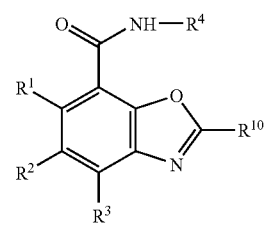

are disclosed as 5-HT$_3$ inhibitors. Those compounds are useful in treating CINV, IBS-D and other diseases and conditions.

16 Claims, No Drawings

2-ALKYLBENZOXAZOLE CARBOXAMIDES AS 5-HT$_3$ MODULATORS

CROSS-REFERENCE TO RELATED APPLICATIONS

This application claims priority from U.S. Provisional Application Ser. No. 60/821,650, filed Aug. 7, 2006, the entire contents of which are incorporated herein by reference.

FIELD OF THE INVENTION

The invention relates to a genus of 2-alkylbenzoxazole carboxamides that are useful in treating chemotherapy-induced nausea and vomiting (CINV) and in treating diarrhea-predominant Irritable Bowel Syndrome (IBS-D).

BACKGROUND OF THE INVENTION

Nausea and vomiting caused by chemotherapy remain among the most distressing side effects for patients undergoing treatment for cancer. Depending upon the chemotherapy agents or regimens given, up to 90% of patients may suffer from some form of chemotherapy-induced nausea and vomiting (CINV). Symptoms from CINV can be severely debilitating and often result in patients refusing further courses of chemotherapy, with obviously unfavorable consequences with respect to progression of the cancer. Furthermore, CINV is burdensome on the medical system, consuming time from the healthcare staff, who could otherwise attend to other patients or medical issues.

CINV is divided into two main categories: acute CINV and delayed CINV. Acute CINV occurs within the first 24 hours of treatment; delayed CINV occurs from 24 hours to 120 hours following treatment. Delayed CINV remains a highly undertreated side effect in patients undergoing chemotherapy, as healthcare providers tend to underestimate the number of patients who suffer from delayed CINV. Furthermore, delayed CINV greatly impairs patients' ability to provide care to themselves once they have been discharged.

Compounds that inhibit serotonin receptors are currently the most effective antiemetics; they constitute the single greatest advance in the management of nausea and vomiting in patients with cancer and have had additional application in radiation-induced nausea and vomiting (RINV) and post-operative nausea and vomiting (PONV). Blocking the 5-HT$_3$ receptor from the serotonin signal produced from chemotherapy-induced damage to the gut's enterochromaffin cells, which house the majority of the body's serotonin reserves, via either a peripheral or central mechanism appears to prevent acute emesis. Except for palonosetron (Aloxi®), 5-HT$_3$ inhibitors have been approved for and most effective against the treatment of acute CINV. Palonosetron, which must be given intravenously, is the only 5-HT$_3$ inhibitor currently approved for the prevention of both acute and delayed CINV. The efficacy of palonosetron against delayed emesis has been postulated to be due to its long serum half-life. Therefore persons of skill in the art accept that 5-HT$_3$ inhibitors that have long serum half-lives will be effective therapeutic agents for both acute and delayed CINV; those that have short half-lives will be useful to treat acute CINV. In addition, the combination of palonosetron, a 5-HT$_3$ inhibitor, and aprepitant (EMEND®), a neurokinin antagonist, has been shown to be highly effective in preventing both acute and delayed CINV following a variety of moderately to highly emetogenic chemotherapy regimens in clinical trials. Notably, combination therapy of either NK1 antagonists or 5-HT$_3$ antagonists with corticosteroids such as dexamethasone, improve the performance of these drugs against acute or delayed emesis. To that point, EMEND® labeling indicates that the drug is dosed with a corticosteroid and a 5-HT$_3$ antagonist.

Irritable Bowel Syndrome (IBS) generally occurs in three types: diarrhea predominant (IBS-D), constipation predominant (IBS-C) and IBS with alternating symptoms termed IBS-A or mixed-mode (IBS-M). Diarrhea predominant Irritable Bowel Syndrome is a debilitating, though seldom fatal, disease. The typical sufferer of IBS-D exhibits primary symptoms including multiple and daily explosive diarrhea attacks and severe daily abdominal cramps. The most common secondary side effects include panic attacks, depression, withdrawal from social and family activities and malnutrition.

At present, compounds that inhibit 5-HT$_3$ receptors are the only effective treatment for IBS-D. The only drug currently approved for IBS-D is alosetron, which was introduced by Glaxo, withdrawn by the FDA because it appeared to cause ischemic colitis, then reinstated by the FDA because the demand was so great for some treatment for IBS-D. In 2002, the US Food and Drug Administration approved alosetron hydrochloride (LOTRONEX®) tablets under restricted conditions for women in whom the medical benefits outweigh the risks. The restrictions on the approval reflect the serious gastrointestinal adverse events that have been reported with the use of alosetron. A second structurally related 5-HT$_3$ inhibitor, cilansetron, had been making its way through clinical trials and recently received a non-approvable letter from the FDA. New, structurally unrelated 5-HT$_3$ inhibitors may be useful for the treatment of IBS-D.

Clearly there is a need for improved therapy for both CINV and IBS-D.

SUMMARY OF THE INVENTION

It has now been found that certain benzoxazoles of the general formula

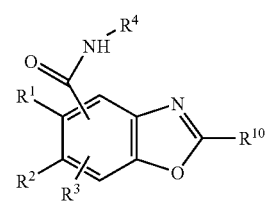

are potent and selective inhibitors of the 5-HT$_3$ receptor. In these compounds $R^1$, $R^2$ and $R^3$ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;

$R^4$ is a residue chosen from:

(i) a saturated nitrogen heterocycle or methyl-substituted saturated nitrogen heterocycle, in which said nitrogen is tertiary, said heterocycle containing at least one 5 or 6-membered ring; and (ii) an imidazolylalkyl residue wherein the imidazole of said imidazolylalkyl is optionally substituted with up to three groups chosen from halogen, (C$_1$-C$_4$)alkyl, substituted (C$_1$-C$_4$)alkyl and NH$_2$; and $R^{10}$ is chosen from the group consisting of
(i) hydrogen;
(ii) $(C_1-C_{10})$alkyl;
(iii) substituted $(C_1-C_{10})$alkyl;
(iv) saturated C-attached heterocyclyl; and
(v) substituted, saturated C-attached heterocyclyl.

In another aspect, the invention relates to pharmaceutical compositions comprising a pharmaceutically acceptable carrier and a therapeutically effective amount of a compound of formula I or II. The compositions may comprise an additional antiemetic agent, particularly a neurokinin antagonist. The compositions may also include a corticosteroid.

In another aspect, the invention relates to a method of treating a disorder arising from inappropriate activity of the serotonin type 3 receptor or dependent upon modulation of the serotonin type 3 receptor. The method comprises administering a therapeutically effective amount of a compound of formula I or II. Exemplary disorders arising from inappropriate activity of the serotonin type 3 receptor or dependent upon modulation of the serotonin type 3 receptor include emesis, particularly CINV, and IBS-D. Other such disorders include psychological disorders, obesity, substance abuse disorders, dementia associated with a neurodegenerative disease, cognition loss, pain, fibromyalgia syndrome and chronic fatigue syndrome (see US published application 2004/0204467). Serotonin type 3 receptor antagonists are also known to be useful for the prevention and treatment of bronchial asthma, bulimia nervosa, sleep apnea, pruritis and migraine (see Costall and Naylor, Current Drug Targets—CNS & Neurological Disorders, 2004:3 27-37 and Israili, Current Med. Chem.—CNS Agents, 2001:1 171-199). Serotonin type 3 receptor antagonists are also known to be useful for the prevention and treatment of epilepsy. Application of such compounds for the treatment of epilepsy has been demonstrated in International Application Number PCT/GB2006/002733.

DETAILED DESCRIPTION OF THE INVENTION

Throughout this specification the substituents are defined when introduced and retain their definitions.

Benzoxazoles of the general formula

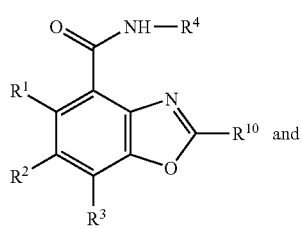

are potent and selective inhibitors of the 5-HT$_3$ receptor. The genus may be divided into two subgenera, the 4-carboxamides (I) and the 7-carboxamides (II):

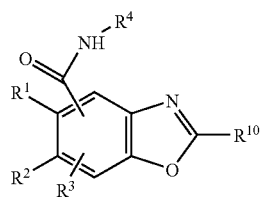

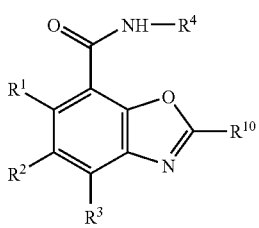

In a first aspect the invention relates to compounds of formula I and II. In some embodiments, $R^4$ is

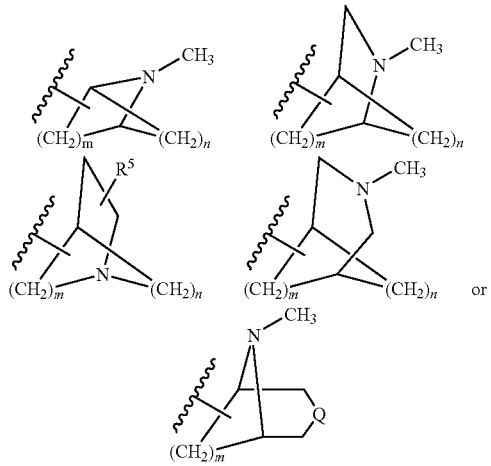

and m is 1, 2, 3 or 4; n is 0, 1, 2, 3 or 4; Q is N(CH$_3$) or —O—; and $R^5$ is hydrogen or methyl. For example, $R^4$ may be quinuclidine, tropane, azabicyclo[3.3.1]nonane, methyl azabicyclo[3.3.1]nonane or dimethyl diazabicyclo[3.3.1]nonane.

In some embodiments, $R^1$, $R^2$ and $R^3$ are hydrogen; in others one of $R^1$, $R^2$, and $R^3$ is halogen.

In some embodiments, $R^{10}$ is chosen from the group consisting of hydrogen and (C$_1$ to C$_3$)alkyl. In other embodiments, $R^{10}$ is chosen from the group consisting of (C$_4$ to C$_{10}$)alkyl and substituted (C$_1$-C$_{10}$)alkyl. Examples of such embodiments are those in which $R^{10}$ is chosen from

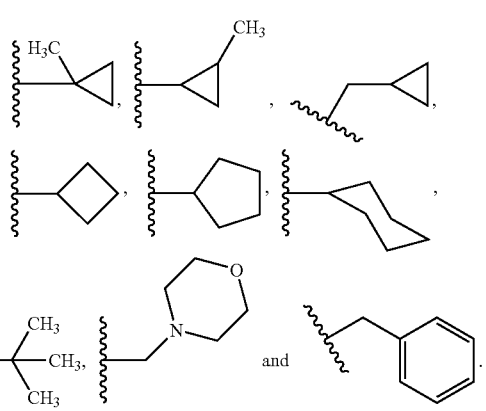

In other embodiments, $R^{10}$ is chosen from the group consisting of saturated, C-attached, nitrogenous heterocyclyl; and substituted, saturated, C-attached, nitrogenous heterocyclyl. Examples include

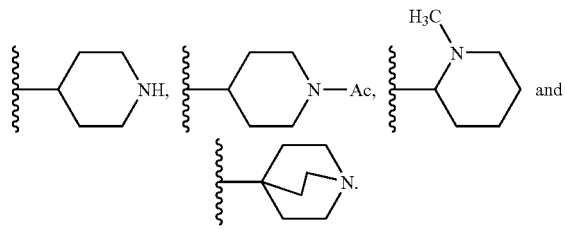

In other embodiments, $R^{10}$ is chosen from the group consisting of saturated, C-attached, oxygen heterocyclyl; and substituted, saturated, C-attached, oxygen heterocyclyl, for example, tetrahydropyran-4-yl.

Compounds falling within the foregoing parent genus and its subgenera are useful as 5-$HT_3$ inhibitors. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a composition aspect, is all compounds of formulae I and II, except those that are in the public's possession.

Definitions

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like. Certain moieties require explicit mention. The statement that alkyl is intended to include linear, branched, or cyclic hydrocarbon structures and combinations thereof means that the following combination of linear and cyclic structural elements (and similar combinations)

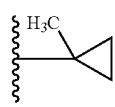

is considered an "alkyl" group. $C_1$ to $C_{20}$ hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl (Ac), benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a residue in which an aryl moiety is attached to the parent through an alkyl. Examples are benzyl, phenethyl and the like. Tolyl is not arylalkyl; tolyl is alkylaryl. Heteroarylalkyl means a heteroaryl residue attached to the parent via alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Nitrogen heterocycles are heterocycles containing at least one nitrogen. They may additionally include other heteroatoms and multiple nitrogens. Examples include quinuclidine, tropane, piperidine, piperazine, morpholine, quinoline and thiazole. It is to be noted that heteroaryl is a subset of heterocycle in which the heterocycle is aromatic. Dihydroheteroaryl are, as the name implies, heteraryl residues formally reduced by one mole of hydrogen. An example of a dihydroheteroaryl residue is 2,3-dihydrobenzofuran.

Substituted alkyl, aryl, cycloalkyl, heterocyclyl etc. refer to alkyl, aryl, cycloalkyl, or heterocyclyl wherein up to four H atoms in each residue are replaced with halogen, haloalkyl, hydroxy, loweralkoxy, carboxy, alkoxycarbonyl (COOR), carboxamido (—$CONR_2$), sulfonamido (—$SO_2NR_2$), cyano, carbonyl, nitro, amino, alkylamino, dialkylamino, mercapto, alkylthio, sulfoxide, sulfone, acylamino, amidino, phenyl, benzyl, heteroaryl, heterocyclyl; phenoxy, benzyloxy, or heteroaryloxy. In the foregoing listing, R is hydrogen or alkyl.

The term "halogen" means fluorine, chlorine, bromine or iodine.

Some of the compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E or a mixture of the two in any proportion.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, chlorine and iodine include $^3$H, $^{14}$C, $^{35}$S, $^{18}$F, $^{36}$Cl and $^{125}$I, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds of the invention may be conveniently divided into two subgenera, the benzoxazole-4-carboxamides I and the benzoxazole-7-carboxamides II:

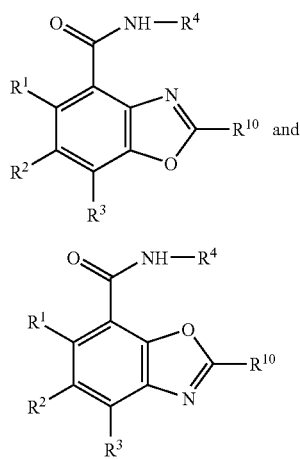

In these compounds, $R^4$ represents a saturated nitrogen heterocycle or methyl-substituted saturated nitrogen heterocycle, in which the nitrogen is tertiary. A nitrogen heterocycle (also referred to as a nitrogenous heterocycle) is a heterocycle containing at least one nitrogen in the ring; it may contain additional nitrogens, as well as other heteroatoms. Nitrogenous heterocycles include piperidine, methylpiperidine, quinuclidine, tropane, azabicyclo[3.3.3]nonane, methyl azabicyclo[3.3.1]nonane, 9-azabicyclo[3.3.1]nonan-3-one, and

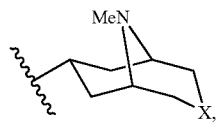

in which X is NCH$_3$, O, S, SO or SO$_2$.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations" is incorporated herein by reference.

Generalized synthetic schemes are presented below:

SCHEME A

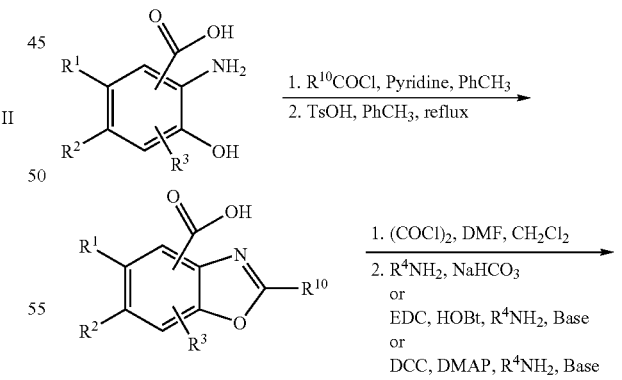

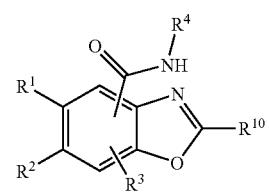

SCHEME B

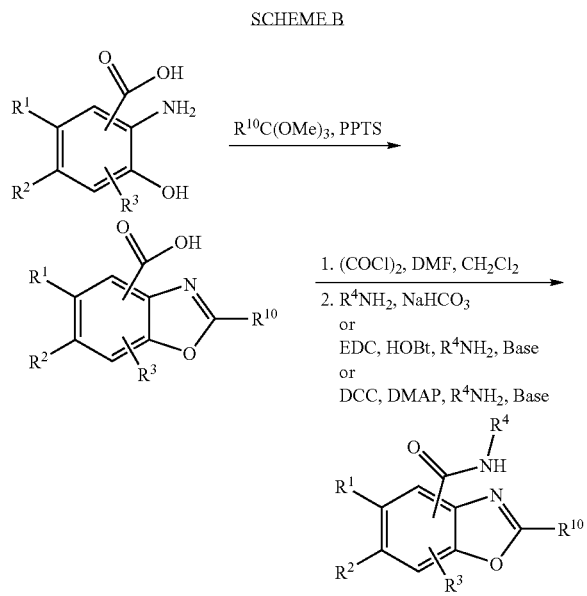

EXAMPLES

Exemplary syntheses are provided below.

Example 1

Preparation of Endo-N-(9-Methyl-9-azabicyclo[3.3.1]non-3-yl)-2-cyclopropylbenzoxazole-4-carboxamide Step A: To a mixture of 2-amino-3-hydroxybenzoic acid hydrobromide (0.25 g, 1.07 mmol) and cyclopropanecarbonyl chloride (0.10 mL, 1.07 mmol) in dichloromethane (8 mL) was added triethylamine (0.60 mL, 4.28 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (8 mL) and the solution was treated with p-toluenesulfonic acid monohydrate (204 mg, 1.07 mmol). The reaction mixture was then heated to reflux for 5 h. The reaction was cooled to room temperature, poured into water and extracted with ethyl acetate. The organic layer was separated then washed with water, brine, dried ($Na_2SO_4$), filtered and concentrated. The crude product was purified by column chromatography (silica gel, 9:1 to 3:1 ethyl acetate/methanol) to afford 2-cyclopropylbenzoxazole-4-carboxylic acid (0.14 g, 65%) as a white solid: $^1$H NMR (500 MHz, DMSO-$d_6$) δ 12.92 (br s, 1H), 7.85 (dd, J=8.0, 0.6 Hz, 1H), 7.81 (d, J=7.8 Hz, 1H), 7.38 (t, J=7.8 Hz, 1H), 2.37-2.31 (m, 1H), 1.26-1.16 (m, 4H); MS (ESI+) m/z 204 (M+H).

Step B: A mixture of 2-cyclopropylbenzoxazole-4-carboxylic acid from Step A (65 mg, 0.32 mmol), endo-3-amino-9-methyl-9-azabicyclo[3.3.1]nonane dihydrochloride (73 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (2 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford endo-N-(9-methyl-9-azabicyclo[3.3.1]non-3-yl)-2-cyclopropylbenzoxazole-4-carboxamide (45 mg, 41%) as a white solid: $^1$H NMR (500 MHz, CDCl$_3$) δ 8.91 (d, J=6.0 Hz, 1H), 8.12 (dd, J=8.0, 1.0 Hz, 1H), 7.53 (dd, J=8.0, 1.0 Hz, 1H), 7.39 (t, J=8.0 Hz, 1H), 4.57-4.51 (m, 1H), 3.09 (d, J=10.5 Hz, 2H), 2.61-2.55 (m, 2H), 2.53 (s, 3H), 2.35-2.25 (m, 1H), 2.12-1.95 (m, 3H), 1.60-1.40 (m, 3H), 1.45-1.22 (m, 4H), 1.12 (d, J=12.5 Hz, 2H); MS (ESI+) m/z 340 (M+H); HPLC>99% (AUC), $t_R$=12.12 min.

Example 2

Preparation of (S)—N-(1-Azabicyclo[2.2.2]oct-3-yl)-2-cyclopropylbenzoxazole-4-carboxamide A mixture of 2-cyclopropylbenzoxazole-4-carboxylic acid (65 mg, 0.32 mmol), (S)-(−)-3-aminoquinuclidine dihydrochloride (64 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (2 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)—N-(1-azabicyclo[2.2.2]oct-3-yl)-2-cyclopropylbenzoxazole-4-carboxamide (43 mg, 43%) as a colorless semisolid: $^1$H NMR (500 MHz, CDCl$_3$) δ 9.43 (d, J=7.0 Hz, 1H), 8.10 (dd, J=7.5, 1.0 Hz, 1H), 7.56 (dd, J=8.0, 2.0 Hz, 1H), 7.36 (t, J=8.5 Hz, 1H), 4.28-4.22 (m, 1H), 3.49 (ddd, J=11.5, 9.5, 2.0 Hz, 1H), 3.10-2.85 (m, 4H), 2.75 (dd, J=14.0, 4.5 Hz, 1H), 2.28-2.20 (m, 1H), 2.12-2.06 (m, 1H), 2.00-1.90 (m, 1H), 1.75-1.69 (m, 2H), 1.60-1.50 (m, 1H), 1.35-1.22 (m, 4H); MS (ESI+) m/z 312 (M+H); HPLC>99% (AUC), $t_R$=12.31 min.

Example 3

Preparation of Endo-N-(9-Methyl-9-azabicyclo[3.3.1]non-3-yl)-2-tert-butylbenzoxazole-4-carboxamide Step A: To a mixture of 2-amino-3-hydroxybenzoic acid hydrobromide (0.30 g, 1.28 mmol) and pivaloyl chloride (0.16 mL, 1.28 mmol) in dichloromethane (10 mL) was added triethylamine (0.72 mL, 5.12 mmol) dropwise, then the reaction mixture was stirred at room temperature for 1 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (10 mL) and the solution was treated with p-toluenesulfonic acid monohydrate (240 mg, 1.26 mmol). The reaction mixture was then heated to reflux for 1.5 h. The reaction was cooled to room temperature, poured into water and extracted with ethyl acetate. The organic layer was separated then washed with water, brine, dried ($Na_2SO_4$), filtered and concentrated. The crude product was purified by column chromatography (silica gel, 9:1 to 3:1 ethyl acetate/methanol) to afford 2-tert-butylbenzoxazole-4-carboxylic acid (0.15 g, 53%) as a white solid: $^1$H NMR (300 MHz, DMSO-$d_6$) δ 7.75-7.71 (m, 2H), 7.33 (t, J=7.8 Hz, 1H), 1.45 (s, 9H); MS (ESI+) m/z 220 (M+H).

Step B: A mixture of 2-tert-butylbenzoxazole-4-carboxylic acid from Step A (70 mg, 0.32 mmol), endo-3-amino-9-methyl-9-azabicyclo[3.3.1]nonane dihydrochloride (73 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford endo-N-(9-methyl-9-azabicyclo[3.3.1]non-3-yl)-2-tert-butylbenzoxazole-4-carboxamide (89 mg, 78%) as a white solid: $^1$H NMR (500 MHz, CDCl$_3$) δ 9.10 (d, J=7.5 Hz, 1H), 8.14 (dd, J=8.0, 1.0 Hz, 1H), 7.59 (dd, J=7.5, 1.5 Hz, 1H), 7.39 (t, J=8.0 Hz, 1H), 4.56-4.50 (m, 1H), 3.08 (d, J=10.5 Hz, 2H), 2.65-2.58 (m, 2H), 2.53 (s, 3H), 2.10-1.95 (m, 3H), 1.60-1.52 (m, 1H), 1.52 (s, 9H), 1.47-1.40 (m, 2H), 1.15 (d, J=12.5 Hz, 2H); MS (ESI+) m/z 356 (M+H); HPLC>99% (AUC), $t_R$=12.89 min.

Example 4

Preparation of (S)—N-(1-Azabicyclo[2.2.2]oct-3-yl)-2-tert-butylbenzoxazole-4-carboxamide A mixture of 2-tert-butylbenzoxazole-4-carboxylic acid (70 mg, 0.32 mmol), (S)-(−)-3-aminoquinuclidine dihydrochloride (64 mg, 0.32 mmol), 1-ethyl-3-(3-dimethylaminopropyl)carbodiimide hydrochloride (123 mg, 0.64 mmol) and 1-hydroxybenzotriazole (86 mg, 0.64 mmol) in DMF (1.5 mL) was stirred at room temperature for 5 min, then triethylamine (0.17 mL, 1.28 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)—N-(1-azabicyclo[2.2.2]oct-3-yl)-2-tert-butylbenzoxazole-4-carboxamide (68 mg, 65%) as a colorless semi-solid: $^1$H NMR (500 MHz, CDCl$_3$) δ 9.60 (d, J=7.5 Hz, 1H), 8.13 (dd, J=7.5, 1.0 Hz, 1H), 7.62 (dd, J=8.0, 2.0 Hz, 1H), 7.41 (t, J=8.0 Hz, 1H), 4.32-4.26 (m, 1H), 3.47 (ddd, J=11.5, 9.5, 2.0 Hz, 1H), 3.06-2.83 (m, 4H), 2.75 (dd, J=14.0, 4.5 Hz, 1H), 2.10-1.95 (m, 2H), 1.76-1.70 (m, 2H), 1.60-1.54 (m, 1H), 1.52 (s, 9H); MS (ESI+) m/z 328 (M+H); HPLC>99% (AUC), $t_R$=11.84 min.

Example 5

Preparation of Endo-N-(9-Methyl-9-azabicyclo [3.3.1]non-3-yl)-2-cyclopentylbenzoxazole-4-carboxamide Hydrochloride Step A: To a suspension of 2-amino-3-hydroxybenzoic acid hydrobromide (300 mg, 1.28 mmol) in dichloromethane (8 mL) was added cyclopentane carbonyl chloride (0.16 mL, 1.28 mmol). The resulting reaction mixture was stirred at room temperature for 10 min, then triethylamine (0.71 mL, 5.13 mmol) was added and the reaction mixture was stirred at room temperature overnight. The reaction was diluted in dichloromethane (30 mL) and quenched with aqueous 2 N HCl (10 mL) until the solution reached pH 1. The aqueous layer was further extracted with dichloromethane (2×30 mL). The organic layers were washed with water and brine, dried over $Na_2SO_4$, filtered and concentrated to an orange solid. The amide product was directly re-dissolved in toluene (8 mL) and the solution was treated with p-toluenesulfonic acid monohydrate (296 mg, 1.56 mmol). The reaction mixture was then heated to reflux for 3 h. The reaction was cooled to room temperature and the toluene was evaporated. The reaction mixture was poured into water and extracted with ethyl acetate. The organic layer was separated, washed with water, brine, dried over $Na_2SO_4$, filtered and concentrated. The crude product was purified by column chromatography (silica gel, 9:1 to 3:1 ethyl acetate/methanol) to afford 2-cyclopentylbenzoxazole-4-carboxylic acid (179 mg, 75%) as a pale orange solid: $^1$H NMR (500 MHz, DMSO-$d_6$) δ 7.85-7.72 (m, 2H), 7.39-7.29 (m, 1H), 2.05-1.50 (m, 9H); MS (ESI+) m/z 232 (M+H).

Step B: A mixture of 2-cyclopentylbenzoxazole-4-carboxylic acid (85 mg, 0.37 mmol), endo-3-amino-9-methyl-9-azabicyclo[3.3.1]nonane dihydrochloride (100 mg, 0.44 mmol), 1-ethyl-3-(3-dimethylaminopropyl)carbodiimide hydrochloride (142 mg, 0.74 mmol) and 1-hydroxybenzotriazole (100 mg, 0.74 mmol) in DMF (2.5 mL) was stirred for 10 min at room temperature, then triethylamine (0.26 mL, 1.85 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and semi-preparative HPLC to afford the free base as a white solid. The free base was dissolved in anhydrous ethyl ether (3 mL). HCl solution (1 M in ether, 0.3 mL, 0.3 mmol) was added. A white precipitate was formed and the mixture was diluted with ethyl ether and left to stand overnight. The solution was decanted off and the solid was dried under high vacuum to afford endo-N-(9-methyl-9-azabicyclo[3.3.1]non-3-yl)-2-cyclopentylbenzoxazole-4-carboxamide hydrochloride (46 mg, 75%) as a white solid: $^1$H NMR (500 MHz, CDCl$_3$) δ 12.23 (br s, 0.5H), 11.83 (br s, 0.5H), 9.50 (d, J=6.0 Hz, 0.5H), 9.38 (d, J=5.0 Hz, 0.5H), 8.12 (dd, J=7.5, 1.0 Hz, 1H), 8.09 (dd, J=8.0, 0.5 Hz, 1H), 7.66 (dd, J=8.5, 1.0 Hz, 1H), 7.62 (dd, J=8.0, 0.5 Hz, 1H), 7.46-7.38 (m, 2H), 4.77-4.69 (m, 0.5H), 4.59-4.52 (m, 0.5H), 3.50-3.49 (m, 1H), 2.95-2.82 (m, 5H), 2.62-2.55 (m, 1H), 2.25-1.62 (m, 14H); MS (ESI+) m/z 368 (M+H); HPLC 96.4% (AUC), $t_R$=12.40 min.

Example 6

Preparation of (S)—N-(1-Azabicyclo[2.2.2]oct-3-yl)-2-cyclopentylbenzoxazole-4-carboxamide Hydrochloride A mixture of 2-cyclopentylbenzoxazole-4-carboxylic acid (85 mg, 0.37 mmol), (S)-3-aminoquinuclidine dihydrochloride (88 mg, 0.44 mmol), 1-ethyl-3-(3-dimethylaminopropyl)carbodiimide hydrochloride (142 mg, 0.74 mmol) and 1-hydroxybenzotriazole (100 mg, 0.74 mmol) in DMF (2.5 mL) was stirred at room temperature for 10 min, then triethylamine (0.26 mL, 1.85 mmol) was added. The resulting reaction mixture was stirred at room temperature overnight. The mixture was diluted with dichloromethane (30 mL), and then washed with a saturated solution of sodium bicarbonate. The aqueous layer was further extracted with dichloromethane (2×30 mL). The combined organics were dried ($Na_2SO_4$), filtered and concentrated. The crude material was purified by column chromatography (silica gel, 90:9:1 ethyl acetate/methanol/concentrated ammonium hydroxide) and semi-preparative HPLC to afford the free base (17 mg, 14%) as an oil. The free base was dissolved in anhydrous ethyl ether (0.8 mL) and dichloromethane (0.3 mL). HCl solution (1 M in ether, 0.1 mL, 0.1 mmol) was added. A white precipitate was formed and the mixture was diluted with ethyl ether and left to stand overnight. The solution was decanted off and the solid was dried under high vacuum to afford (S)—N-(1-azabicyclo[2.2.2]oct-3-yl)-2-cyclopentylbenzoxazole-4-carboxamide hydrochloride (13 mg, 74%) as a white solid: $^1$H NMR (500 MHz, $CDCl_3$) δ 12.47 (br s, 1H), 9.62 (d, J=6.5 Hz, 1H), 8.09 (dd, J=8.0, 1.0 Hz, 1H), 7.66 (dd, J=8.0, 0.5 Hz, 1H), 7.43 (t, J=7.5 Hz, 1H), 4.68-4.62 (m, 1H), 3.80 (t, J=10.5 Hz, 1H), 3.39-3.28 (m, 1H), 3.23-3.16 (m, 1H), 2.85 (d, J=5.0 Hz, 1H), 2.48 (s, 1H), 2.38-2.29 (m, 1H), 2.27-2.18 (m, 2H), 2.15-2.07 (m, 2H), 2.06-1.96 (m, 4H), 1.95-1.75 (m, 6H); MS (ESI+) m/z 340 (M+H); HPLC 98.4% (AUC), $t_R$=11.94 min.

Example 7

Preparation of Endo-N-(9-Methyl-9-azabicyclo[3.3.1]non-3-yl)-2-(1-methylcyclopropyl)benzoxazole-4-carboxamide Hydrochloride Step A: To an ice-cold solution of 1-methylcyclopropanecarboxylic acid (214 mg, 2.14 mmol) in dichloromethane (10 mL) was added oxalyl chloride (0.19 mL, 2.14 mmol) dropwise. The ice bath was removed and stirring was continued for 1 h. 2-Amino-3-hydroxybenzoic acid hydrobromide (500 mg, 2.14 mmol) was added followed by triethylamine (0.90 mL, 6.42 mmol). The resulting reaction mixture was stirred at room temperature overnight. The reaction was quenched with aqueous 1 N HCl (25 mL) until the solution reached pH 1. The reaction mixture was extracted with dichloromethane. The combined organic layers were dried over $Na_2SO_4$, filtered and concentrated to a brown solid. The crude was dissolved in toluene (10 mL) and the solution was treated with p-toluenesulfonic acid monohydrate (477 mg, 2.50 mmol). The reaction mixture was then heated to reflux for 1 h. The reaction was cooled to room temperature, poured into water and extracted with ethyl acetate. The organic layer was separated, then washed with water (5×50 mL), brine, dried ($Na_2SO_4$), filtered and concentrated to afford 2-(1-methylcyclopropyl)benzoxazole-4-carboxylic acid (306 mg, 65%) as a light yellow solid: $^1$H NMR (500 MHz, DMSO-$d_6$) δ 12.89 (br s, 1H), 7.85 (dd, J=8.0, 0.9 Hz, 1H), 7.81 (dd, J=7.7, 0.9 Hz, 1H), 7.39 (t, J=7.9 Hz, 1H), 2.91 (s, 3H), 1.42-1.37 (m, 2H), 1.10-1.05 (m, 2H); MS (ESI+) m/z 218 (M+H).

Step B: A mixture of 2-(1-methylcyclopropyl)benzoxazole-4-carboxylic acid (60 mg, 0.27 mmol), endo-3-amino-9-methyl-9-azabicyclo[3.3.1]nonane dihydrochloride (77 mg, 0.34 mmol), 1-ethyl-3-(3-dimethylaminopropyl)carbodiimide hydrochloride (103 mg, 0.54 mmol) and 1-hydroxybenzotriazole (73 mg, 0.54 mmol) in DMF (2 mL) was stirred at room temperature for 5 min, then triethylamine (0.11 mL, 0.81 mmol) was added. The resulting reaction mixture was stirred at room temperature for 12 h. The mixture was diluted with dichloromethane (20 mL), and then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 90:9:1 dichloromethane/methanol/concentrated ammonium hydroxide) to afford the carboxamide (69 mg, 79%) as a light brown solid: $^1$H NMR (500 MHz, $CDCl_3$) δ 8.95 (d, J=6.4 Hz, 1H), 8.11 (dd, J=7.8, 1.0 Hz, 1H), 7.51 (dd, J=8.0, 0.9 Hz, 1H), 7.32 (t, J=7.9 Hz, 1H), 4.50-4.40 (m, 1H), 3.20-3.10 (m, 2H), 2.65-2.57 (m, 2H), 2.56 (s, 3H), 2.15-1.95 (m, 4H), 1.75-1.65 (m, 1H), 1.60-1.40 (m, 4H), 1.30-1.24 (m, 3H), 1.20-1.15 (m, 2H), 1.09-1.05 (m, 1H); MS (ESI+) m/z 354 (M+H).

Step C: To a solution of endo-N-(9-methyl-9-azabicyclo[3.3.1]nonan-3-yl)-2-(1-methylcyclopropyl)benzoxazole-4-carboxamide (64 mg, 0.18 mmol) in methanol (2.0 mL) was added a solution of HCl in diethyl ether (1 N, 0.36 mL, 0.36 mmol) at 0° C. slowly. The reaction mixture was diluted with diethyl ether. The resulting solid was filtered and washed with diethyl ether to afford endo-N-(9-methyl-9-azabicyclo[3.3.1]non-3-yl)-2-(1-methylcyclopropyl)benzoxazole-4-carboxamide hydrochloride (67 mg, 95%) as a white solid: $^1$H NMR (500 MHz, DMSO-$d_6$) δ 9.98 (br s, 0.3H), 9.44 (br s, 0.7H), 9.18 (d, J=6.8 Hz, 0.3H), 8.96 (d, J=6.8 Hz, 0.7H), 7.95-7.88 (m, 2H), 7.50-7.42 (m, 1H), 4.55-4.50 (m, 0.7H), 4.38-4.32 (m, 0.3H), 3.68-3.62 (m, 1.3H), 3.59-3.52 (m, 0.7H), 2.88-2.82 (m, 3H), 2.75-2.60 (m, 2H), 2.35-2.10 (m, 3H), 1.82-1.70 (m, 3H), 1.60-1.42 (m, 7H), 1.20-1.14 (m, 2H); MS (ESI+) m/z 354 (M+H); HPLC>99% (AUC), $t_R$=12.08 min.

Example 8

Preparation of (S)—N-(1-Azabicyclo[2.2.2]oct-3-yl)-2-(1-methylcyclopropyl)benzoxazole-4-carboxamide Hydrochloride Step A: A mixture of 2-(1-methylcyclopropyl)benzoxazole-4-carboxylic acid (60 mg, 0.27 mmol), (S)-(−)-3-aminoquinuclidine dihydrochloride (67 mg, 0.34 mmol), 1-ethyl-3-(3-dimethylaminopropyl)carbodiimide hydrochloride (103 mg, 0.54 mmol) and 1-hydroxybenzotriazole (73 mg, 0.54 mmol) in DMF (2 mL) was stirred at room temperature for 5 min, then triethylamine (0.11 mL, 0.81 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 90:9:1 dichloromethane/methanol/concentrated ammonium hydroxide) to afford (S)—N-(1-azabicyclo[2.2.2]oct-3-yl)-2-(1-methylcyclopropyl)benzoxazole-4-carboxamide (69 mg, 79%) as a light brown semi-solid: $^1$H NMR (500 MHz, CDCl$_3$) δ 9.61 (d, J=7.3 Hz, 1H), 8.10 (dd, J=7.8, 1.0 Hz, 1H), 7.55 (dd, J=8.0, 0.9 Hz, 1H), 7.36 (t, J=7.9 Hz, 1H), 4.34-4.28 (m, 1H), 3.55 (m, 1H), 3.10-3.00 (m, 2H), 2.96-2.88 (m, 2H), 2.82-2.74 (m, 1H), 2.12-2.02 (m, 2H), 1.80-1.75 (m, 2H), 1.65 (s, 3H), 1.64-1.57 (m, 1H), 1.52-1.48 (m, 2H), 1.10-1.05 (m, 2H); MS (ESI+) m/z 326 (M+H).

Step B: To a solution of (S)—N-(1-azabicyclo[2.2.2]oct-3-yl)-2-(1-methylcyclopropyl)benzoxazole-4-carboxamide (63 mg, 0.19 mmol) in methanol (2 mL) was added a solution of HCl in diethyl ether (1 N, 0.38 mL, 0.38 mmol) at room temperature slowly. The reaction mixture was diluted with diethyl ether. The resulting solid was filtered and washed with diethyl ether to afford (S)—N-(1-azabicyclo[2.2.2]oct-3-yl)-2-(1-methylcyclopropyl)benzoxazole-4-carboxamide hydrochloride (60 mg, 88%) as a white solid: $^1$H NMR (500 MHz, DMSO-d$_6$) δ 10.22 (br s, 1H), 9.36 (d, J=6.6 Hz, 1H), 8.10 (d, J=8.0 Hz, 2H), 7.46 (t, J=7.9 Hz, 1H), 4.45-4.36 (m, 1H), 3.77-3.70 (m, 1H), 3.35-3.26 (m, 2H), 3.24 (t, J=7.9 Hz, 2H), 3.17 (dd, J=13.2, 3.7 Hz, 1H), 2.30-2.15 (m, 2H), 2.00-1.90 (m, 3H), 1.61 (s, 3H), 1.48-1.40 (m, 2H), 1.20-1.15 (m, 2H); MS (ESI+) m/z 326 (M+H); HPLC>99% (AUC), t$_R$=11.65 min.

Example 9

Preparation of Endo-N-(9-Methyl-9-azabicyclo[3.3.1]non-3-yl)-2-benzylbenzoxazole-4-carboxamide Hydrochloride Step A: To a mixture of 2-amino-3-hydroxybenzoic acid hydrobromide (0.5 g, 2.14 mmol) and triethylamine (0.90 mL, 6.42 mmol) in dichloromethane (15 mL) was added phenylacetyl chloride (0.28 mL, 2.14 mmol) dropwise, then the reaction mixture was stirred at room temperature overnight. The reaction mixture was diluted with dichloromethane, and then washed with 2 N HCl. The aqueous layer was extracted with dichloromethane. The combined organic layers were washed with brine, dried (Na$_2$SO$_4$), filtered and concentrated. The crude product was dissolved in toluene (8 mL) and the solution was treated with p-toluenesulfonic acid monohydrate (537 mg, 2.83 mmol). The reaction mixture was then heated to reflux for 5 h. The reaction was cooled to room temperature, poured into water and extracted with ethyl acetate. The organic layer was separated, then washed with water (3×100 mL), brine, dried (Na$_2$SO$_4$), filtered and concentrated to afford 2-benzylbenzoxazole-4-carboxylic acid (277 mg, 51%) as a white solid: $^1$H NMR (500 MHz, DMSO-d$_6$) δ 13.08 (br s, 1H), 7.91 (dd, J=7.1, 1.0 Hz, 1H), 7.85 (dd, J=7.7, 1.0 Hz, 1H), 7.44 (t, J=7.9 Hz, 1H), 7.40-7.34 (m, 4H), 7.31-7.27 (m, 1H), 4.40 (s, 2H); MS (ESI+) m/z 254 (M+H).

Step B: A mixture of 2-benzylbenzoxazole-4-carboxylic acid (76 mg, 0.30 mmol), endo-3-amino-9-methyl-9-azabicyclo[3.3.1]nonane dihydrochloride (86 mg, 0.38 mmol), 1-ethyl-3-(3-dimethylaminopropyl)carbodiimide hydrochloride (115 mg, 0.60 mmol) and 1-hydroxybenzotriazole (81 mg, 0.60 mmol) in DMF (3 mL) was stirred at room temperature for 5 min, then triethylamine (0.17 mL, 1.28 mmol) was added. The resulting reaction mixture was stirred at room temperature for 12 h. The mixture was diluted with ethyl acetate (20 mL), and then washed with a saturated solution of sodium bicarbonate (10 mL). The aqueous layer was further extracted with ethyl acetate (3×25 mL). The combined organics were dried (Na$_2$SO$_4$), filtered and concentrated. The crude material was purified by column chromatography (silica gel, 90:9:1 dichloromethane/methanol/concentrated ammonium hydroxide) to afford the carboxamide (81 mg, 70%) as a white solid: $^1$H NMR (500 MHz, CDCl$_3$) δ 8.93 (br s, 1H), 8.14 (dd, J=8.0, 1.0 Hz, 1H), 7.59 (dd, J=8.0, 1.0 Hz, 1H), 7.42-7.27 (m, 6H), 4.60-4.50 (m, 1H), 4.32 (s, 2H), 3.20-3.10 (m, 2H), 2.65-2.50 (m, 2H), 2.58 (s, 3H), 2.15-1.95 (m, 3H), 1.60-1.50 (m, 3H), 1.22-1.10 (m, 2H); MS (ESI+) m/z 390 (M+H).

Step C: To a solution of endo-N-(9-methyl-9-azabicyclo[3.3.1]nonan-3-yl)-2-benzylbenzoxazole-4-carboxamide (78 mg, 0.2 mmol) in methanol (1.5 mL) was added a solution of HCl in diethyl ether (1 N, 0.4 mL, 0.4 mmol) at room temperature slowly. The reaction mixture was diluted with diethyl ether. The resulting solid was filtered and washed with diethyl ether to afford endo-N-(9-methyl-9-azabicyclo[3.3.1]non-3-yl)-2-benzylbenzoxazole-4-carboxamide hydrochloride (89 mg, quantitative) as a white solid: $^1$H NMR (500 MHz, DMSO-d$_6$) δ 10.62 (br s, 0.3H), 10.27 (br s, 0.7H), 9.12 (d, J=7.3 Hz, 0.3H), 8.90 (d, J=7.3 Hz, 0.7H), 7.95-7.85 (m, 2H), 7.55-7.48 (m, 1H), 7.45-7.38 (m, 4H), 7.35-7.30 (m, 1H), 4.60-4.55 (m, 0.7H), 4.47 (s, 1.3H), 4.46 (s, 0.7H), 4.31-4.28 (m, 0.3H), 3.64-3.56 (m, 1.3H), 3.52-3.45 (m, 0.7H), 2.84-2.80 (m, 3H), 2.75-2.60 (m, 2H), 2.30-2.20 (m, 3H), 1.80-1.30 (m, 5H); MS (ESI+) m/z 390 (M+H); HPLC 97.6% (AUC), t$_R$=12.10 min.

Example 10

Preparation of (S)—N-(1-Azabicyclo[2.2.2]oct-3-yl)-2-benzylbenzoxazole-4-carboxamide Hydrochloride Step A: A mixture of 2-benzylbenzoxazole-4-carboxylic acid (76 mg, 0.30 mmol), (S)-(−)-3-aminoquinuclidine dihydrochloride (75 mg, 0.38 mmol), 1-ethyl-3-(3-dimethylaminopropyl)carbodiimide hydrochloride (115 mg, 0.60 mmol) and 1-hydroxybenzotriazole (81 mg, 0.60 mmol) in DMF (3 mL) was stirred at room temperature for 5 min, then triethylamine (0.13 mL, 0.90 mmol) was added. The resulting reaction mixture was stirred at room temperature for 12 h. The mixture was diluted with ethyl acetate (50 mL), then washed with a saturated solution of sodium bicarbonate. The aqueous layer was further extracted with ethyl acetate (3×25 mL). The combined organics were dried (Na$_2$SO$_4$), filtered and concentrated. The crude material was purified by column chromatography (silica gel, 90:9:1 dichloromethane/methanol/concentrated ammonium hydroxide) to afford the carboxamide (89 mg, 82%) as a white solid: $^1$H NMR (500 MHz, CDCl$_3$) δ 9.34 (d, J=7.1 Hz, 1H), 8.12 (dd, J=8.0, 1.0 Hz, 1H), 7.63 (dd, J=8.0, 1.0 Hz, 1H), 7.42 (t, J=7.9 Hz, 1H), 7.40-7.32 (m, 5H), 4.32 (s, 2H), 4.31-4.26 (m, 1H), 3.50-3.43 (m, 1H), 3.00-2.82 (m, 2H), 2.75-2.68 (m, 1H), 2.10-2.05 (m, 1H), 1.81-1.70 (m, 3H), 1.55-1.45 (m, 3H); MS (ESI+) m/z 362 (M+H).

Step B: To a solution of (S)—N-(1-azabicyclo[2.2.2]oct-3-yl)-2-benzylbenzoxazole-4-carboxamide (84 mg, 0.23 mmol) in methanol (1.5 mL) was added a solution of HCl in diethyl ether (1 N, 0.5 mL, 0.5 mmol) at room temperature slowly. The reaction mixture was diluted with diethyl ether. The resulting solid was filtered and washed with diethyl ether to afford (S)—N-(1-azabicyclo[2.2.2]oct-3-yl)-2-benzylbenzoxazole-4-carboxamide hydrochloride (71 mg, 78%) as a white solid: $^1$H NMR (500 MHz, DMSO-d$_6$) δ 10.05 (br s, 1H), 9.19 (d, J=7.1 Hz, 1H), 7.95 (d, J=8.0 Hz, 1H), 7.88 (d, J=8.0 Hz, 1H), 7.52 (t, J=7.9 Hz, 1H), 7.45-7.30 (m, 5H), 4.48 (s, 2H), 4.37-4.32 (m, 1H), 3.75-3.65 (m, 1H), 3.22-3.15 (m, 3H), 3.10-3.05 (m, 2H), 2.15-2.10 (m, 1H), 1.95-1.90 (m, 2H), 1.80-1.60 (m, 2H); MS (ESI+) m/z 362 (M+H); HPLC>99% (AUC), $t_R$=11.81 min.

Example 11

Preparation of Endo-N-(9-Methyl-9-azabicyclo[3.3.1]non-3-yl)-2-(cyclopropylmethyl)benzoxazole-4-carboxamide Hydrochloride Step A: To an ice-cold solution of 2-cyclopropyl acetic acid (321 mg, 3.21 mmol) in dichloromethane (10 mL) was added oxalyl chloride (0.29 mL, 3.21 mmol) dropwise and a few drops of DMF. The ice bath was removed and stirring was continued for 1 h. 2-Amino-3-hydroxybenzoic acid hydrobromide (750 mg, 3.21 mmol) was added followed by triethylamine (0.90 mL, 6.42 mmol). The resulting reaction mixture was stirred at room temperature overnight. The reaction was quenched with aqueous 1 N HCl (25 mL) until the solution reached pH 1. The reaction mixture was extracted with dichloromethane. The combined organic layers were dried over $Na_2SO_4$, filtered and concentrated to a brown solid. The crude was dissolved in toluene (10 mL) and the solution was treated with p-toluenesulfonic acid monohydrate (735 mg, 3.87 mmol). The reaction mixture was then heated to reflux for 3 h. The reaction was cooled to room temperature, poured into water and extracted with ethyl acetate. The organic layer was separated, washed with water (5×50 mL) and brine, dried ($Na_2SO_4$), filtered, and concentrated. The crude was purified by recrystallization from diethyl ether and hexanes to afford 2-(cyclopropylmethyl)benzoxazole-4-carboxylic acid (441 mg, 63%) as a light brown solid: $^1$H NMR (500 MHz, DMSO-$d_6$) δ 13.04 (br s, 1H), 7.94 (dd, J=8.1, 0.9 Hz, 1H), 7.81 (dd, J=7.8, 0.9 Hz, 1H), 7.45 (t, J=7.9 Hz, 1H), 2.92 (d, J=7.0 Hz, 2H), 1.27-1.16 (m, 1H), 0.60-0.54 (m, 2H), 0.36-0.30 (m, 2H); MS (ESI+) m/z 218 (M+H).

Step B: A mixture of 2-(cyclopropylmethyl)benzoxazole-4-carboxylic acid (100 mg, 0.46 mmol), endo-3-amino-9-methyl-9-azabicyclo[3.3.1]nonane dihydrochloride (129 mg, 0.57 mmol), 1-ethyl-3-(3-dimethylaminopropyl)carbodiimide hydrochloride (175 mg, 0.92 mmol) and 1-hydroxybenzotriazole (124 mg, 0.92 mmol) in DMF (2 mL) was stirred at room temperature for 5 min, then triethylamine (0.19 mL, 1.28 mmol) was added. The resulting reaction mixture was stirred at room temperature for 12 h. The mixture was diluted with ethyl acetate (20 mL), then washed with a saturated solution of sodium bicarbonate (15 mL). The aqueous layer was further extracted with ethyl acetate (3×100 mL). The combined organics were dried ($Na_2SO_4$), filtered and concentrated. The crude material was purified by column chromatography (silica gel, 90:9:1 dichloromethane/methanol/concentrated ammonium hydroxide) to afford the carboxamide (101 mg, 62%) as a light brown semi-solid: $^1$H NMR (500 MHz, CDCl$_3$) δ 9.03 (d, J=6.4 Hz, 1H), 8.15 (dd, J=7.8, 1.0 Hz, 1H), 7.61 (dd, J=8.0, 0.9 Hz, 1H), 7.41 (t, J=7.9 Hz, 1H), 4.50-4.40 (m, 1H), 3.20-3.10 (m, 2H), 2.90 (d, J=7.0 Hz, 2H), 2.63-2.58 (m, 2H), 2.56 (s, 3H), 2.15-1.95 (m, 3H), 1.60-1.50 (m, 3H), 1.30-1.22 (m, 1H), 1.20-1.10 (m, 2H), 0.71-0.60 (m, 2H), 0.42-0.34 (m, 2H); MS (ESI+) m/z 354 (M+H).

Step C: To a solution of endo-N-(9-methyl-9-azabicyclo[3.3.1]nonan-3-yl)-2-(1-methylcyclopropyl)benzoxazole-4-carboxamide (98 mg, 0.27 mmol) in methanol (0.5 mL) was added a solution of HCl in diethyl ether (1 N, 0.35 mL, 0.35 mmol) at room temperature slowly. The reaction mixture was diluted with diethyl ether. The resulting solid was filtered and washed with diethyl ether to afford endo-N-(9-methyl-9-azabicyclo[3.3.1]non-3-yl)-2-(cyclopropylmethyl)benzoxazole-4-carboxamide hydrochloride (55 mg, 52%) as a light brown solid: $^1$H NMR (500 MHz, DMSO-$d_6$) δ 10.30 (br s, 0.3H), 9.60 (br s, 0.7H), 9.26 (d, J=7.3 Hz, 0.3H), 8.97 (d, J=7.3 Hz, 0.7H), 7.95-7.88 (m, 2H), 7.55-7.48 (m, 1H), 4.65-4.58 (m, 0.7H), 4.38-4.30 (m, 0.3H), 3.70-3.66 (m, 1.3H), 3.62-3.58 (m, 0.7H), 2.94 (s, 2H), 2.88-2.82 (m, 3H), 2.75-2.60 (m, 2H), 2.28-2.20 (m, 1H), 2.18-2.05 (m, 2H), 1.82-1.75 (m, 3H), 1.60-1.48 (m, 2H), 1.30-1.20 (m, 1H), 0.65-0.55 (m, 2H), 0.40-0.30 (m, 2H); MS (ESI+) m/z 354 (M+H); HPLC>99% (AUC), $t_R$=12.22 min.

Example 12

Preparation of (S)—N-(1-Azabicyclo[2.2.2]oct-3-yl)-2-(cyclopropylmethyl)benzoxazole-4-carboxamide Hydrochloride Step A: A mixture of 2-(cyclopropylmethyl)benzoxazole-4-carboxylic acid (100 mg, 0.46 mmol), (S)-(−)-3-aminoquinuclidine dihydrochloride (113 mg, 0.57 mmol), 1-ethyl-3-(3-dimethylaminopropyl)carbodiimide hydrochloride (175 mg, 0.92 mmol) and 1-hydroxybenzotriazole (124 mg, 0.92 mmol) in DMF (2 mL) was stirred at room temperature for 5 min, then triethylamine (0.19 mL, 1.38 mmol) was added. The resulting reaction mixture was stirred at room temperature for 12 h. The mixture was diluted with ethyl acetate (20 mL), then washed with a saturated solution of sodium bicarbonate (10 mL). The aqueous layer was further extracted with ethyl acetate (3×15 mL). The combined organics were dried ($Na_2SO_4$), filtered and concentrated. The crude material was purified by column chromatography (silica gel, 90:9:1 dichloromethane/methanol/concentrated ammonium hydroxide) to afford the carboxamide (98 mg, 66%) as a light brown semi-solid: $^1$H NMR (500 MHz, CDCl$_3$) δ 9.53 (d, J=7.1 Hz, 1H), 8.14 (dd, J=7.8, 1.0 Hz, 1H), 7.63 (dd, J=8.0, 0.9 Hz, 1H), 7.42 (t, J=7.9 Hz, 1H), 4.35-4.27 (m, 1H), 3.54-3.46 (m, 1H), 3.10-2.90 (m, 6H), 2.78 (dd, J=14.0, 4.5 Hz, 1H), 2.15-2.10 (m, 1H), 2.08-2.01 (m, 1H), 1.82-1.75 (m, 2H), 1.64-1.57 (m, 1H), 1.35-1.25 (m, 1H), 0.71-0.60 (m, 2H), 0.42-0.34 (m, 2H); MS (ESI+) m/z 326 (M+H).

Step B: To a solution of (S)—N-(1-azabicyclo[2.2.2]oct-3-yl)-2-(cyclopropylmethyl)benzoxazole-4-carboxamide (94 mg, 0.29 mmol) in methanol (0.5 mL) was added a solution of HCl in diethyl ether (1 N, 0.32 mL, 0.34 mmol) at 0° C. slowly. The reaction mixture was diluted with diethyl ether. The resulting solid was filtered and washed with diethyl ether to afford (S—N-(1-azabicyclo[2.2.2]oct-3-yl)-2-(cyclopropylmethyl)benzoxazole-4-carboxamide hydrochloride (81 mg, 77%) as a white solid: $^1$H NMR (500 MHz, DMSO-$d_6$) δ 10.12 (br s, 1H), 9.36 (d, J=6.6 Hz, 1H), 7.97 (d, J=8.1 Hz, 2H), 7.46 (t, J=7.9 Hz, 1H), 4.45-4.38 (m, 1H), 3.80-3.47 (m, 1H), 3.28-3.22 (m, 2H), 3.15 (dd, J=14.0, 4.5 Hz, 1H), 3.00 (d, J=7.0 Hz, 2H), 2.30-2.16 (m, 2H), 2.00-1.90 (m, 3H), 1.61 (s, 3H), 1.48-1.40 (m, 2H), 1.20-1.15 (m, 2H); MS (ESI+) m/z 326 (M+H); HPLC>99% (AUC), $t_R$=11.65 min.

Example 13

Preparation of Endo-N-(9-Methyl-9-azabicyclo[3.3.1]non-3-yl)-2-(2-methylcyclopropyl)benzoxazole-4-carboxamide Hydrochloride Step A: To an ice-cold solution of 2-methylcyclopropanecarboxylic acid (214 mg, 2.14 mmol) in dichloromethane (10 mL) was added oxalyl chloride (0.19 mL, 2.14 mmol) dropwise and a few drops of DMF. The ice bath was removed and stirring was continued for 1 h. 2-Amino-3-hydroxybenzoic acid hydrobromide (500 mg, 2.14 mmol) was added followed by triethylamine (0.90 mL, 6.42 mmol). The resulting reaction mixture was stirred at room temperature overnight. The reaction was quenched with aqueous 1 N HCl (25 mL) until the solution reached pH 1. The reaction mixture was extracted with dichloromethane. The combined organic layers were dried over $Na_2SO_4$, filtered and concentrated to a brown solid. The crude was dissolved in toluene (10 mL) and the solution was treated with p-toluenesulfonic acid monohydrate (574 mg, 3.0 mmol). The reaction mixture was then heated to reflux for 5 h. The reaction was cooled to room temperature, poured into water and extracted with ethyl acetate. The organic layer was separated then washed with water (5×150 mL), brine, dried ($Na_2SO_4$), filtered and concentrated to afford 2-(2-methylcyclopropyl)benzoxazole-4-carboxylic acid (409 mg, 88%) as a yellow solid: $^1H$ NMR (500 MHz, DMSO-$d_6$) δ 12.92 (br s, 1H), 7.84 (dd, J=8.1, 1.0 Hz, 1H), 7.81 (dd, J=7.8, 1.0 Hz, 1H), 7.38 (t, J=7.9 Hz, 1H), 2.10-2.05 (m, 1H), 1.62-1.57 (m, 1H), 1.41-1.34 (m, 1H), 1.28 (d, J=6.5 Hz, 3H), 1.08-1.02 (m, 1H); MS (ESI+) m/z 218 (M+H).

Step B: A mixture of 2-(2-methylcyclopropyl)benzoxazole-4-carboxylic acid (200 mg, 0.92 mmol), endo-3-amino-9-methyl-9-azabicyclo[3.3.1]nonane dihydrochloride (261 mg, 1.15 mmol), 1-ethyl-3-(3-dimethylaminopropyl)carbodiimide hydrochloride (351 mg, 1.84 mmol) and 1-hydroxybenzotriazole (248 mg, 1.15 mmol) in DMF (2 mL) was stirred at room temperature for 5 min, then triethylamine (0.38 mL, 2.76 mmol) was added. The resulting reaction mixture was stirred at room temperature for 12 h. The mixture was diluted with dichloromethane (100 mL), then washed with a saturated solution of sodium bicarbonate (20 mL). The aqueous layer was further extracted with dichloromethane (3×150 mL). The combined organics were dried ($Na_2SO_4$), filtered and concentrated. The crude material was purified by column chromatography (silica gel, 90:9:1 dichloromethane/methanol/concentrated ammonium hydroxide) to afford the carboxamide (207 mg, 64%) as a brown solid: $^1H$ NMR (500 MHz, $CDCl_3$) δ 8.95 (d, J=6.4 Hz, 1H), 8.11 (dd, J=7.8, 1.0 Hz, 1H), 7.51 (dd, J=8.0, 0.9 Hz, 1H), 7.32 (t, J=7.9 Hz, 1H), 4.50-4.40 (m, 1H), 3.20-3.10 (m, 2H), 2.65-2.57 (m, 2H), 2.56 (s, 3H), 2.15-1.95 (m, 4H), 1.75-1.65 (m, 1H), 1.60-1.40 (m, 4H), 1.30-1.24 (m, 3H), 1.20-1.15 (m, 2H), 1.09-1.05 (m, 1H); MS (ESI+) m/z 354 (M+H).

Step C: To a solution of endo-N-(9-methyl-9-azabicyclo[3.3.1]nonan-3-yl)-2-(2-methylcyclopropyl)benzoxazole-4-carboxamide (201 mg, 0.57 mmol) in methanol (0.5 mL) was added a solution of HCl in diethyl ether (1 N, 1.13 mL, 1.13 mmol) at room temperature slowly. The reaction mixture was diluted with diethyl ether. The resulting solid was filtered and washed with diethyl ether to afford endo-N-(9-methyl-9-azabicyclo[3.3.1]non-3-yl)-2-(2-methylcyclopropyl)benzoxazole-4-carboxamide hydrochloride (221 mg, 98%) as a white solid and as a mixture of diastereomers: $^1H$ NMR (500 MHz, $CDCl_3$) δ 12.24 (br s, 0.4H), 11.79 (br s, 0.6H), 9.41 (d, J=5.9 Hz, 0.4H), 9.35 (d, J=5.6 Hz, 0.6H), 8.08 (dd, J=7.8, 0.9 Hz, 0.4H), 8.04 (dd, J=7.8, 0.9 Hz, 0.6H), 7.59 (dd, J=8.1, 0.9 Hz, 0.4H), 7.54 (dd, J=8.1, 0.9 Hz, 0.6H), 7.38 (t, J=7.9 Hz, 0.4H), 7.34 (t, J=7.9 Hz, 0.6H), 4.76-4.70 (m, 0.7H), 4.56-4.52 (m, 0.3H), 3.65-3.60 (m, 2H), 2.95-2.55 (m, 7H), 2.15-2.05 (m, 1H), 2.02-1.90 (m, 2H), 1.85-1.60 (m, 5H), 1.52- 1.42 (m, 1H), 1.32-1.28 (m, 3H), 1.15-1.05 (m, 1H); MS (ESI+) m/z 354 (M+H); HPLC>99% (AUC), $t_R$=12.01 min.

Example 14

Preparation of (S)—N-(1-Azabicyclo[2.2.2]oct-3-yl)-2-(2-methylcyclopropyl)benzoxazole-4-carboxamide Hydrochloride Step A: A mixture of 2-(2-methylcyclopropyl)benzoxazole-4-carboxylic acid (200 mg, 0.92 mmol), (S)-(−)-3-aminoquinuclidine dihydrochloride (229 mg, 1.15 mmol), 1-ethyl-3-(3-dimethylaminopropyl)carbodiimide hydrochloride (351 mg, 1.84 mmol) and 1-hydroxybenzotriazole (248 mg, 1.84 mmol) in DMF (6 mL) was stirred at room temperature for 5 min, then triethylamine (0.38 mL, 2.76 mmol) was added. The resulting reaction mixture was stirred at room temperature for 12 h. The mixture was diluted with dichloromethane (100 mL), then washed with a saturated solution of sodium bicarbonate (20 mL). The aqueous layer was further extracted with dichloromethane (3×150 mL). The combined organics were dried ($Na_2SO_4$), filtered and concentrated. The crude material was purified by column chromatography (silica gel, 90:9:1 dichloromethane/methanol/concentrated ammonium hydroxide) to afford the product (155 mg, 52%) as a colorless semi-solid and as a mixture of two diastereomers: $^1H$ NMR (500 MHz, $CDCl_3$) δ 9.44 (d, J=7.1 Hz, 1H), 8.10 (dd, J=7.5, 1.0 Hz, 1H), 7.56 (dd, J=8.0, 2.0 Hz, 1H), 7.34 (t, J=8.0 Hz, 1H), 4.32-4.26 (m, 1H), 3.54-3.46 (m, 1H), 3.10-2.90 (m, 4H), 2.75 (dd, J=14.0, 4.5 Hz, 1H), 2.15-2.10 (m, 1H), 2.04-1.94 (m, 2H), 1.80-1.75 (m, 2H), 1.70-1.60 (m, 2H), 1.50-1.45 (m, 1H), 1.28 (d, J=6.5 Hz, 3H), 1.10-1.05 (m, 1H); MS (ESI+) m/z 326 (M+H).

Step B: To a solution of (S)—N-(1-azabicyclo[2.2.2]oct-3-yl)-2-(2-methylcyclopropyl)benzoxazole-4-carboxamide (149 mg, 0.45 mmol) in methanol (0.5 mL) was added a solution of HCl in diethyl ether (1 N, 0.92 mL, 0.92 mmol) at room temperature slowly. The reaction mixture was diluted with diethyl ether. The resulting solid was filtered and washed with diethyl ether to afford (S)—N-(1-azabicyclo[2.2.2]oct-3-yl)-2-(2-methylcyclopropyl)benzoxazole-4-carboxamide hydrochloride (82 mg, 51%) as a white solid and as a mixture of diastereomers: $^1H$ NMR (500 MHz, DMSO-$d_6$) δ 12.68 (br s, 1H), 9.51 (br s, 1H), 8.12 (d, J=8.0 Hz, 1H), 7.68 (d, J=8.0 Hz, 1H), 7.38 (t, J=7.9 Hz, 1H), 4.69-4.58 (m, 1H), 3.80-3.70 (m, 1H), 3.50-3.20 (m, 5H), 2.60-2.50 (m, 1H), 2.40-2.35 (m, 1H), 2.25-1.95 (m, 4H), 1.65-1.60 (m, 1H), 1.50-1.42 (m, 1H), 1.35-1.30 (m, 2H), 1.17-1.10 (m, 2H); MS (ESI+) m/z 326 (M+H); HPLC 98.9% (AUC), $t_R$=11.59 min.

Example 15

Preparation of Endo-N-(9-Methyl-9-azabicyclo[3.3.1]non-3-yl)-2-cyclohexylbenzoxazole-4-carboxamide Hydrochloride Step A: To a mixture of 2-amino-3-hydroxybenzoic acid hydrobromide (500 mg, 2.13 mmol) and cyclohexane carbonyl chloride (0.29 mL, 2.13 mmol) in dichloromethane (20 mL) was added triethylamine (0.90 mL, 6.41 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (8 mL) and the solution was treated with p-toluenesulfonic acid monohydrate (485 mg, 2.55 mmol). The reaction mixture was then heated to reflux for 5 h. The reaction was cooled to room temperature, poured into water and extracted with ethyl acetate. The organic layer was separated, then washed with water (7×100 mL), brine, dried ($Na_2SO_4$), filtered and concentrated. The crude product was purified by re-crystallization from ethyl acetate and hexanes to afford 2-cyclohexylbenzoxazole-4-carboxylic acid (346 mg, 66%) as a brown solid: $^1$H NMR (500 MHz, DMSO-$d_6$) δ 13.01 (br s, 1H), 7.92 (dd, J=8.0, 0.9 Hz, 1H), 7.84 (dd, J=7.8, 0.9 Hz 1H), 7.44 (t, J=7.8 Hz, 1H), 3.08-3.02 (m, 1H), 2.14-2.05 (m, 2H), 1.82-1.75 (m, 2H), 1.72-1.60 (m, 3H), 1.47-1.38 (m, 2H), 1.35-1.25 (m, 1H); MS (ESI+) m/z 246 (M+H).

Step B: A mixture of 2-cyclohexylbenzoxazole-4-carboxylic acid (100 mg, 0.41 mmol), endo-3-amino-9-methyl-9-azabicyclo[3.3.1]nonane dihydrochloride (118 mg, 0.51 mmol), 1-ethyl-3-(3-dimethylaminopropyl)carbodiimide hydrochloride (175 mg, 0.82 mmol) and 1-hydroxybenzotriazole (109 mg, 0.82 mmol) in DMF (5 mL) was stirred at room temperature for 5 min, then triethylamine (0.17 mL, 1.26 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×50 mL). The combined organics were dried ($Na_2SO_4$), filtered and concentrated. The crude material was purified by column chromatography (silica gel, 90:9:1 dichloromethane/methanol/concentrated ammonium hydroxide) to afford the carboxamide (143 mg, 91%) as a light brown semi-solid: $^1$H NMR (500 MHz, CDCl$_3$) δ 9.11 (d, J=6.0 Hz, 1H), 8.13 (dd, J=8.0, 1.0 Hz, 1H), 7.59 (dd, J=8.0, 0.9 Hz, 1H), 7.39 (t, J=8.0 Hz, 1H), 4.62-4.52 (m, 1H), 3.05-3.00 (m, 1H), 2.61-2.55 (m, 2H), 2.60 (s, 3H), 2.21-2.00 (m, 5H), 1.90-1.86 (m, 2H), 1.78-1.70 (m, 4H), 1.65-1.35 (m, 9H); MS (ESI+) m/z 382 (M+H).

Step C: To a solution of the carboxamide of step B (136 mg, 0.35 mmol) in methanol (1.0 mL) was added a solution of HCl in diethyl ether (1 N, 0.71 mL, 0.71 mmol) at 0° C. slowly. The reaction mixture was diluted with diethyl ether. The resulting solid was filtered and washed with diethyl ether to afford endo-N-(9-methyl-9-azabicyclo[3.3.1]non-3-yl)-2-cyclohexylbenzoxazole-4-carboxamide hydrochloride (159 mg, quantitative) as a white solid: $^1$H NMR (500 MHz, CDCl$_3$) δ 12.24 (br s, 0.3H), 11.83 (br s, 0.7H), 9.53 (d, J=5.4 Hz, 0.3H), 9.39 (d, J=5.4 Hz, 0.7H), 8.12 (dd, J=7.7, 0.8 Hz, 0.3H), 8.08 (dd, J=7.7, 0.8 Hz, 0.7H), 7.66 (dd, J=8.1, 0.8 Hz, 0.3H), 7.62 (dd, J=8.1, 0.8 Hz, 0.7H), 7.44 (t, J=7.9 Hz, 0.3H), 7.40 (t, J=7.9 Hz, 0.7H), 4.75-4.68 (m, 0.7H), 4.56-4.50 (m, 0.3H), 3.65-3.50 (m, 2H), 3.05-3.00 (m, 1H), 2.95-2.82 (m, 5H), 2.80-2.60 (m, 2H), 2.20-2.05 (m, 4H), 2.00-1.65 (m, 9H), 1.50-1.25 (m, 3H); MS (ESI+) m/z 382 (M+H); HPLC>99% (AUC), $t_R$=12.72 min.

Example 16

Preparation of (S)—N-(1-Azabicyclo[2.2.2]oct-3-yl)-2-cyclohexylbenzoxazole-4-carboxamide Hydrochloride Step A: A mixture of 2-cyclohexylbenzoxazole-4-carboxylic acid (100 mg, 0.41 mmol), (S)-(−)-3-aminoquinuclidine dihydrochloride (102 mg, 0.51 mmol), 1-ethyl-3-(3-dimethylaminopropyl)carbodiimide hydrochloride (155 mg, 0.81 mmol) and 1-hydroxybenzotriazole (109 mg, 0.81 mmol) in DMF (5 mL) was stirred at room temperature for 5 min, then triethylamine (0.17 mL, 1.28 mmol) was added. The resulting reaction mixture was stirred at room temperature for 12 h. The mixture was diluted with ethyl acetate (20 mL), then washed with a saturated solution of sodium bicarbonate (20 mL). The aqueous layer was further extracted with ethyl acetate (3×100 mL). The combined organics were washed with water (3×150 mL), dried ($Na_2SO_4$), filtered and concentrated. The crude material was purified by column chromatography (silica gel, 90:9:1 dichloromethane/methanol/concentrated ammonium hydroxide) to afford the carboxamide (139 mg, 95%) as a light brown solid: $^1$H NMR (500 MHz, CDCl$_3$) δ 9.58 (d, J=6.5 Hz, 1H), 8.12 (dd, J=7.8, 1.0 Hz, 1H), 7.61 (dd, J=8.0, 0.9 Hz, 1H), 7.41 (t, J=7.9 Hz, 1H), 4.35-4.28 (m, 1H), 3.55-3.45 (m, 1H), 3.10-2.90 (m, 5H), 2.81 (dd, J=14.0, 4.5 Hz, 1H), 2.24-2.22 (m, 2H), 2.16-2.11 (m, 1H), 2.10-2.00 (m, 1H), 1.90-1.85 (m, 2H), 1.80-1.68 (m, 5H), 1.66-1.57 (m, 1H), 1.53-1.42 (m, 2H), 1.40-1.34 (m, 1H); MS (ESI+) m/z 354 (M+H).

Step B: To a solution of (S)—N-(1-azabicyclo[2.2.2]oct-3-yl)-2-cyclohexylbenzoxazole-4-carboxamide (136 mg, 0.39 mmol) in methanol (1.0 mL) was added a solution of HCl in diethyl ether (1 N, 0.8 mL, 0.8 mmol) at room temperature slowly. The reaction mixture was diluted with diethyl ether. The resulting solid was filtered and washed with diethyl ether to afford (S)—N-(1-azabicyclo[2.2.2]oct-3-yl)-2-cyclohexylbenzoxazole-4-carboxamide hydrochloride (147 mg, 96%) as a white solid: $^1$H NMR (500 MHz, CDCl$_3$) δ 12.68 (br s, 1H), 9.62 (d, J=6.5 Hz, 1H), 8.11 (dd, J=7.8, 1.0 Hz, 1H), 7.67 (dd, J=8.0, 0.9 Hz, 1H), 7.43 (t, J=7.9 Hz, 1H), 4.70-4.63 (m, 1H), 3.80-3.74 (m, 1H), 3.45-3.28 (m, 3H), 3.25-3.15 (m, 1H), 3.07-3.00 (m, 1H), 2.53-2.46 (m, 1H), 2.40-2.30 (m, 1H), 2.24-2.07 (m, 4H), 2.05-1.95 (m, 1H), 1.93-1.84 (m, 2H), 1.83-1.63 (m, 4H), 1.55-1.42 (m, 2H), 1.40-1.30 (m, 1H); MS (ESI+) m/z 354 (M+H); HPLC>99% (AUC), $t_R$=12.30 min.

Example 17

Preparation of Endo-N-(9-Methyl-9-azabicyclo[3.3.1]non-3-yl)-2-cyclobutylbenzoxazole-4-carboxamide Hydrochloride Step A: To a mixture of 2-amino-3-hydroxybenzoic acid hydrobromide (0.50 g, 2.13 mmol) and cyclobutanecarbonyl chloride (0.24 mL, 2.13 mmol) in dichloromethane (20 mL) was added triethylamine (0.90 mL, 6.41 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried ($Na_2SO_4$), filtered and concentrated. The crude product was dissolved in toluene (8 mL) and the solution was treated with p-toluenesulfonic acid monohydrate (676 mg, 3.56 mmol). The reaction mixture was then heated to reflux for 5 h. The reaction was cooled to room temperature, poured into water and extracted with ethyl acetate. The combined organic layers were washed with water and brine, dried ($Na_2SO_4$), filtered and concentrated. The crude product was purified by re-crystallization from ethyl acetate and hexanes to afford 2-cyclobutylbenzoxazole-4-carboxylic acid (420 mg, 73%) as a brown solid: $^1$H NMR (500 MHz, DMSO-$d_6$) δ 12.96 (br s, 1H), 7.92 (dd, J=8.1, 0.8 Hz, 1H), 7.84 (dd, J=7.6, 0.8 Hz, 1H), 7.44 (t, J=7.9 Hz, 1H), 3.95-3.85 (m, 1H), 2.46-2.39 (m, 4H), 2.28-2.00 (m, 2H); MS (ESI+) m/z 218 (M+H).

Step B: A mixture of 2-cyclobutylbenzoxazole-4-carboxylic acid (208 mg, 0.96 mmol), endo-3-amino-9-methyl-9-azabicyclo[3.3.1]nonane dihydrochloride (238 mg, 0.19 mmol), 1-ethyl-3-(3-dimethylaminopropyl)carbodiimide hydrochloride (367 mg, 1.92 mmol) and 1-hydroxybenzotriazole (259 mg, 1.92 mmol) in DMF (10 mL) was stirred at room temperature for 5 min, then triethylamine (0.54 mL, 3.84 mmol) was added. The resulting reaction mixture was stirred at room temperature for 12 h. The mixture was diluted with dichloromethane (100 mL), then washed with a saturated solution of sodium bicarbonate (50 mL). The aqueous layer was further extracted with dichloromethane (3×150 mL). The combined organics were dried ($Na_2SO_4$), filtered and concentrated. The crude material was purified by column chromatography (silica gel, 90:9:1 dichloromethane/methanol/concentrated ammonium hydroxide) to afford the amide (241 mg, 71%) as a light brown semi-solid: $^1$H NMR (300 MHz, $CDCl_3$) δ 9.11 (d, J=6.0 Hz, 1H), 8.14 (dd, J=8.0, 1.0 Hz, 1H), 7.59 (dd, J=8.0, 0.9 Hz, 1H), 7.40 (t, J=8.0 Hz, 1H), 4.60-4.50 (m, 1H), 3.90-3.80 (m, 1H), 3.30-3.20 (m, 2H), 2.61-2.55 (m, 6H), 2.60 (s, 3H), 2.30-2.00 (m, 6H), 1.60-1.50 (m, 2H), 1.20-1.10 (m, 2H); MS (ESI+) m/z 354 (M+H).

Step C: To a solution of the carboxamide from step B (239 mg, 0.67 mmol) in methanol (1.0 mL) was added a solution of HCl in diethyl ether (1 N, 1.35 mL, 1.35 mmol) at room temperature slowly. The reaction mixture was diluted with diethyl ether. The resulting solid was filtered and washed with diethyl ether to afford endo-N-(9-methyl-9-azabicyclo[3.3.1]non-3-yl)-2-cyclobutylbenzoxazole-4-carboxamide hydrochloride (15 mg, 6%) as a white solid: $^1$H NMR (500 MHz, $CDCl_3$) δ 12.26 (br s, 0.4H), 11.84 (br s, 0.6H), 9.53 (d, J=5.6 Hz, 0.4H), 9.39 (d, J=5.6 Hz, 0.6H), 8.13 (dd, J=7.7, 0.8 Hz, 0.4H), 8.09 (dd, J=7.7, 0.8 Hz, 0.6H), 7.66 (dd, J=8.1, 0.8 Hz, 0.4H), 7.62 (dd, J=8.1, 0.8 Hz, 0.6H), 7.47 (t, J=7.9 Hz, 0.4H), 7.41 (t, J=7.9 Hz, 0.6H), 4.78-4.70 (m, 0.6H), 4.56-4.50 (m, 0.4H), 3.39-3.38 (m, 1H), 3.60-3.55 (m, 2H), 2.95-2.82 (m, 5H), 2.80-2.45 (m, 6H), 2.30-2.22 (m, 3H), 2.00-1.90 (m, 1H), 1.85-1.60 (m, 4H); MS (ESI+) m/z 354 (M+H); HPLC>99% (AUC), $t_R$=12.72 min.

Example 18

Preparation of (S)—N-(1-Azabicyclo[2.2.2]oct-3-yl)-2-cyclobutylbenzoxazole-4-carboxamide Hydrochloride Step A: A mixture of 2-cyclobutylbenzoxazole-4-carboxylic acid (208 mg, 0.96 mmol), (S)-(−)-3-aminoquinuclidine dihydrochloride (238 mg, 1.19 mmol), 1-ethyl-3-(3-dimethylaminopropyl)carbodiimide hydrochloride (367 mg, 1.92 mmol) and 1-hydroxybenzotriazole (259 mg, 1.92 mmol) in DMF (10 mL) was stirred at room temperature for 5 min, then triethylamine (0.54 mL, 3.84 mmol) was added. The resulting reaction mixture was stirred at room temperature for 12 h. The mixture was diluted with dichloromethane (100 mL), then washed with a saturated solution of sodium bicarbonate (50 mL). The aqueous layer was further extracted with dichloromethane (3×150 mL). The combined organics were dried ($Na_2SO_4$), filtered and concentrated. The crude material was purified by column chromatography (silica gel, 89:10:1 dichloromethane/methanol/concentrated ammonium hydroxide) to afford the amide (229 mg, 73%) as a light brown solid: $^1$H NMR (500 MHz, $CDCl_3$) δ 9.57 (d, J=7.8 Hz, 1H), 8.13 (dd, J=7.8, 1.0 Hz, 1H), 7.62 (dd, J=8.0, 0.9 Hz, 1H), 7.41 (t, J=7.9 Hz, 1H), 4.36-4.26 (m, 1H), 3.90-3.76 (m, 1H), 3.56-3.46 (m, 1H), 3.10-2.90 (m, 4H), 2.82 (dd, J=14.0, 4.5 Hz, 1H), 2.60-2.48 (m, 4H), 2.30-2.00 (m, 4H), 1.84-1.72 (m, 2H), 1.60-1.55 (m, 1H); MS (ESI+) m/z 326 (M+H).

Step B: To a solution of (S)—N-(1-azabicyclo[2.2.2]oct-3-yl)-2-cyclobutylbenzoxazole-4-carboxamide (226 mg, 0.69 mmol) in methanol (1.0 mL) was added a solution of HCl in diethyl ether (1 N, 0.8 mL, 0.8 mmol) at room temperature slowly. The reaction mixture was diluted with diethyl ether. The resulting solid was filtered and washed with diethyl ether to afford (S)—N-(1-azabicyclo[2.2.2]oct-3-yl)-2-cyclobutylbenzoxazole-4-carboxamide hydrochloride (151 mg, 60%) as a white solid: $^1$H NMR (500 MHz, $CDCl_3$) δ 12.68 (br s, 1H), 9.61 (d, J=7.0 Hz, 1H), 8.13 (dd, J=7.8, 1.0 Hz, 1H), 7.62 (dd, J=8.0, 0.9 Hz, 1H), 7.44 (t, J=7.8 Hz, 1H), 4.68-4.62 (m, 1H), 3.90-3.75 (m, 2H), 3.50-3.23 (m, 5H), 2.60-2.50 (m, 5H), 2.40-2.30 (m, 1H), 2.25-1.95 (m, 5H); MS (ESI+) m/z 326 (M+H); HPLC>99% (AUC), $t_R$=11.60 min.

Example 19

Preparation of (S)—N-(1-Azabicyclo[2.2.2]oct-3-yl)-6-fluoro-2-cyclopropylbenzoxazole-4-carboxamide Hydrochloride Step A: Iodine (3.6 g, 14.2 mmol) was added to a mixture of methyl 2-amino-5-fluorobenzoate (2.4 g, 14.2 mmol), silver sulfate (4.42 g, 14.2 mmol) and ethanol (30 mL) at room temperature. The mixture was stirred under nitrogen for 1 h, and then quenched with a saturated solution of sodium bicarbonate, extracted with ethyl acetate. The combined organic layers were washed with brine, dried ($Na_2SO_4$), filtered and concentrated. The crude material was purified by column chromatography (silica gel, 90:10 hexanes/ethyl acetate) to afford methyl 2-amino-5-fluoro-3-iodobenzoate (3.9 g, 93%) as a light yellow solid: $^1$H NMR (300 MHz, $CDCl_3$) δ 7.66-7.58 (m, 2H), 6.21 (br s, 2H), 3.89 (s, 3H); $^{19}$F NMR (282 MHz, $CDCl_3$) δ 127.87; MS (ESI+) m/z 296 (M+H).

Step B: A mixture of methyl 2-amino-5-fluoro-3-iodobenzoate from Step A (500 mg, 1.69 mmol), bis(pinacolato)diboron (515 mg, 2.03 mmol), potassium acetate (497 mg, 5.07 mmol), and toluene (10 mL) was deoxygenated with nitrogen for 15 min. $PdCl_2$(dppf) (277 mg, 0.34 mmol) was added. The mixture was heated at 100° C. under nitrogen for 24 h and then cooled to room temperature, quenched with a saturated solution of sodium bicarbonate, extracted with ethyl acetate. The combined organic layers were washed with brine, dried ($Na_2SO_4$), filtered and concentrated. The crude material was purified by column chromatography (silica gel, 90:10 hexanes/ethyl acetate) to afford the borolane (264 mg, 53%) as a light yellow solid: $^1$H NMR (300 MHz, $CDCl_3$) δ 7.64 (dd, J=9.6, 3.3 Hz, 1H), 7.52 (dd, J=8.1, 3.3 Hz, 1H), 6.88 (br s, 2H), 3.85 (s, 3H), 1.35 (s, 12H); $^{19}$F NMR (282 MHz, $CDCl_3$) δ −131.16; MS (ESI+) m/z 296 (M+H).

Step C: Cyclopropanecarboxylic acid chloride (0.26 mL, 2.9 mmol) was added to a solution of the amine from Step B (560 mg, 1.90 mmol) in methylene chloride (5 mL) at room temperature, followed by triethylamine (0.53 mL, 3.8 mmol). The mixture was stirred under nitrogen overnight and then quenched with a saturated solution of sodium bicarbonate, extracted with methylene chloride. The combined organic layers were washed with brine, dried ($Na_2SO_4$), filtered and concentrated to afford the crude amide (680 mg, 98%) as a light yellow solid: $^1$H NMR (300 MHz, $CDCl_3$) δ 12.30 (br s, 1H), 7.62-7.54 (m, 2H), 3.95 (s, 3H), 1.80-1.70 (m, 1H), 1.41 (dd, J=4.2, 3.3 Hz, 2H), 1.28 (s, 12H), 1.15 (dd, J=7.8, 3.3 Hz, 2H); $^{19}$F NMR (282 MHz, $CDCl_3$) δ 115.70; MS (ESI+) m/z 364 (M+H).

Step D: To a solution of sodium hydroxide (112 mg, 2.81 mmol) and sodium bicarbonate (628 mg, 7.48 mmol) in water (20 mL) at 0° C., was added oxone (1.73 g, 2.81 mmol), followed by the borolane from Step C (680 mg, 1.87 mmol) in acetone (20 mL). The mixture was allowed to warm to room temperature and stirred for 2 h, and then quenched with water, extracted with methylene chloride. The combined organic layers were washed with brine, dried (Na$_2$SO$_4$), filtered and concentrated. The crude material was purified by Combi-flash chromatography (silica gel, 90:10 hexanes/ethyl acetate) to afford methyl 2-(cyclopropanecarboxamido)-5-fluoro-3-hydroxybenzoate (180 mg, 38%) as a white solid: $^1$H NMR (300 MHz, CDCl$_3$) δ 11.30 (br s, 1H), 10.58 (s, 1H), 7.29 (dd, J=8.4, 3.0 Hz, 1H), 6.94 (dd, J=8.4, 3.0 Hz, 1H), 3.95 (s, 3H), 1.82-1.74 (m, 1H), 1.19-1.14 (m, 2H), 1.04-0.95 (m, 2H); $^{19}$F NMR (282 MHz, CDCl$_3$) δ −115.74; MS (ESI+) m/z 254 (M+H).

Step E: A mixture of 2-(cyclopropanecarboxamido)-5-fluoro-3-hydroxybenzoate from Step D (180 mg, 0.71 mmol), p-toluenesulfonic acid monohydrate (202 mg, 1.07 mmol) and toluene (5 mL) was heated at reflux under nitrogen for 3 h. The reaction mixture was then cooled to room temperature, diluted with ethyl acetate, washed with a saturated solution of sodium bicarbonate and brine, dried over sodium sulfate, filtered and concentrated. The crude material was purified by Combi-flash chromatography (silica gel, 60:40 hexanes/ethyl acetate) to afford methyl 2-cyclopropyl-6-fluorobenzoxazole-4-carboxylate (115 mg, 69%) as a white solid: $^1$H NMR (300 MHz, CDCl$_3$) δ 7.68 (dd, J=10.2, 2.4 Hz, 1H), 7.34 (dd, J=7.5, 2.4 Hz, 1H), 4.02 (s, 3H), 2.39-2.29 (m, 1H), 1.35-1.29 (m, 2H), 1.26-1.17 (m, 2H); $^{19}$F NMR (282 MHz, CDCl$_3$) δ −116.29; MS (ESI+) m/z 236 (M+H).

Step F: A mixture of the ester from Step E (115 mg, 0.49 mmol), 2 N NaOH (2.0 mL, 4.0 mmol), and methanol (5 mL) was stirred at room temperature under nitrogen for 2 h. The reaction mixture was acidified with 1 N HCl, extracted with methylene chloride, washed with brine, dried over sodium sulfate, filtered and concentrated to afford 2-cyclopropyl-6-fluorobenzoxazole-4-carboxylic acid (105 mg, 97%) as a white solid: $^1$H NMR (300 MHz, CDCl$_3$) δ 12.90 (br s, 1H), 7.91 (dd, J=8.1, 2.4 Hz, 1H), 7.58 (dd, J=10.2, 2.4 Hz, 1H), 2.39-2.29 (m, 1H), 1.25-1.14 (m, 4H); $^{19}$F NMR (282 MHz, CDCl$_3$) δ −116.79; MS (ESI+) m/z 222 (M+H).

Step G: A mixture of 2-cyclopropyl-6-fluorobenzoxazole-4-carboxylic acid from Step F (50 mg, 0.23 mmol), (S)-3-aminoquinuclidine dihydrochloride (55 mg, 0.28 mmol), 1-ethyl-3-(3-dimethylaminopropyl)carbodiimide hydrochloride (88 mg, 0.46 mmol) and 1-hydroxybenzotriazole (62 mg, 0.46 mmol) in DMF (5 mL) was stirred under nitrogen at room temperature for 10 min, and then triethylamine (0.19 mL, 1.4 mmol) was added. The resulting reaction mixture was stirred at room temperature overnight, and then was quenched with a saturated solution of sodium bicarbonate, extracted with methylene chloride. The combined organic layers were dried (Na$_2$SO$_4$), filtered and concentrated. The crude material was purified by Combi-flash chromatography (silica gel, 90:9:1 ethyl acetate/methanol/concentrated ammonium hydroxide) to afford the desired amide (50 mg, 67%) as a light yellow solid: $^1$H NMR (300 MHz, CDCl$_3$) δ 9.36 (d, J=7.5 Hz, 1H), 7.84 (dd, J=10.5, 2.4 Hz, 1H), 7.29 (dd, J=7.5, 2.4 Hz, 1H), 4.24-4.19 (m, 1H), 3.45 (ddd, J=14.0, 9.5, 2.0 Hz, 1H), 3.10-2.65 (m, 5H), 2.28-2.06 (m, 2H), 1.95-1.85 (m, 1H), 1.75-1.52 (m, 3H), 1.31-1.25 (m, 4H); $^{19}$F NMR (282 MHz, CDCl$_3$) δ −115.30; MS (ESI+) m/z 330 (M+H).

Step H: Hydrogen chloride in diethyl ether (1.0 M, 0.15 mL, 0.15 mmol) was added dropwise to a solution of the amide from Step G (50 mg, 0.15 mmol) in methylene chloride (1 mL) and diethyl ether (5 mL) at 0° C. The mixture was stirred for 5 min, and then diethyl ether (30 mL) was added. The resulting solid was filtered, washed with diethyl ether, and dried under vacuum overnight to afford (S)—N-(1-azabicyclo[2.2.2]oct-3-yl)-6-fluoro-2-cyclopropylbenzoxazole-4-carboxamide hydrochloride (45 mg, 82%) as a white solid: $^1$H NMR (300 MHz, DMSO-d$_6$) δ 10.26 (br s, 1H), 9.16 (d, J=6.6 Hz, 1H), 7.94 (dd, J=8.1, 2.4 Hz, 1H), 7.60 (dd, J=10.5, 2.4 Hz, 1H), 4.42-4.34 (m, 1H), 3.72 (ddd, J=14.0, 9.5, 2.0 Hz, 1H), 3.40-3.15 (m, 5H), 2.55-2.45 (m, 1H), 2.28-2.06 (m, 2H), 1.95-1.85 (m, 3H), 1.35-1.22 (m, 4H); $^{19}$F NMR (282 MHz, DMSO-d$_6$) δ −115.68; MS (ESI+) m/z 330 (M+H); HPLC>99% (AUC), t$_R$=11.40 min.

Example 20

Preparation of Endo-N-(9-Methyl-9-azabicyclo[3.3.1]non-3-yl)-6-fluoro-2-cyclopropylbenzoxazole-4-carboxamide Hydrochloride Step A: A mixture of methyl 2-cyclopropyl-6-fluorobenzoxazole-4-carboxylate (50 mg, 0.23 mmol), endo-3-amino-9-methyl-9-azabicyclo[3.3.1]nonane dihydrochloride (64 mg, 0.28 mmol), 1-ethyl-3-(3-dimethylaminopropyl)carbodiimide hydrochloride (88 mg, 0.46 mmol) and 1-hydroxybenzotriazole (62 mg, 0.46 mmol) in DMF (5 mL) was stirred under nitrogen at room temperature for 10 min, and then triethylamine (0.19 mL, 1.4 mmol) was added. The resulting reaction mixture was stirred at room temperature overnight, and then was quenched with a saturated solution of sodium bicarbonate, extracted with methylene chloride. The combined organic layers were washed with brine, dried (Na$_2$SO$_4$), filtered and concentrated. The crude material was purified by Combi-flash chromatography (silica gel, 90:9:1 ethyl acetate/methanol/concentrated ammonium hydroxide) to afford the carboxamide (62 mg, 77%) as a light yellow solid: $^1$H NMR (300 MHz, CDCl$_3$) δ 8.83 (d, J=7.5 Hz, 1H), 7.86 (dd, J=10.5, 2.4 Hz, 1H), 7.26 (dd, J=7.5, 2.4 Hz, 1H), 4.62-4.45 (m, 1H), 3.13-3.06 (m, 2H), 2.62-2.55 (m, 2H), 2.54 (s, 3H), 2.35-1.98 (m, 4H), 1.62-1.46 (m, 2H), 1.31-1.13 (m, 6H); $^{19}$F NMR (282 MHz, CDCl$_3$) δ −115.55; MS (ESI+) m/z 358 (M+H).

Step B: Hydrogen chloride in diethyl ether (1.0 M, 0.2 mL, 0.2 mmol) was added dropwise to a solution of the amide from Step A (62 mg, 0.17 mmol) in methanol (1 mL) and diethyl ether (5 mL) at 0° C. The mixture was stirred for 5 min, and then diethyl ether (30 mL) was added. The resulting solid was filtered, washed with diethyl ether, and dried under vacuum overnight to afford endo-N-(9-methyl-9-azabicyclo[3.3.1]non-3-yl)-6-fluoro-2-cyclopropylbenzoxazole-4-carboxamide hydrochloride (46 mg, 68%) as a white solid: $^1$H NMR (300 MHz, DMSO-d$_6$) δ 10.25 (br s, 0.4H), 9.72 (br s, 0.6H), 9.07 (d, J=6.0 Hz, 0.4H), 8.81 (d, J=6.9 Hz, 0.6H), 7.98-7.90 (m, 1H), 7.65-7.59 (m, 1H), 4.62-4.30 (m, 1H), 3.68-3.55 (m, 2H), 2.84 (s, 1.5H), 2.83 (s, 1.5H), 2.68-2.55 (m, 2H), 2.45-2.35 (m, 1H), 2.25-1.75 (m, 4H), 1.60-1.46 (m, 3H), 1.35-1.16 (m, 6H); $^{19}$F NMR (282 MHz, DMSO-d$_6$) δ −115.69; MS (ESI+) m/z 358 (M+H); HPLC>99% (AUC), t$_R$=11.86 min.

Example 21

Preparation of N-(9-Ethyl-9-azabicyclo[3.3.1]non-3-yl)-2-cyclopropylbenzoxazole-4-carboxamide Hydrochloride Step A: A mixture of endo-3-amino-9-methyl-9-azabicyclo[3.3.1]nonane dihydrochloride (500 mg, 2.20 mmol), (Boc)$_2$O (528 mg, 2.42 mmol), triethylamine (0.92 mL, 6.6 mmol) and methylene chloride (10 mL) was stirred under nitrogen at room temperature overnight, and then quenched with a saturated solution of sodium bicarbonate, extracted with methylene chloride. The combined organic layers were washed with brine, dried (Na$_2$SO$_4$), filtered and concentrated to give crude tert-butyl 9-methyl-9-azabicyclo[3.3.1]nonan-3-ylcarbamate (530 mg, 95%) as a white solid: $^1$H NMR (500 MHz, CDCl$_3$) δ 4.26 (br s, 1H), 3.98 (br s, 1H), 3.03-3.00 (m, 2H), 2.45 (s, 3H), 2.43-2.36 (m, 2H), 1.95-1.86 (m, 3H), 1.48-1.46 (m, 1H), 1.44 (s, 9H), 1.16-0.98 (m, 4H); MS (ESI+) m/z 255 (M+H).

Step B: To a solution of the carbamate from Step A (430 mg, 1.69 mmol) in THF (2 mL) at 0° C. was added a solution of sodium hydroxide (2.0 g, 50 mmol) in water (20 mL), followed by a solution of KMnO$_4$ (2.0 g, 12.6 mmol) in water (100 mL). The mixture was allowed to warm to room temperature and stirred overnight. Additional KMnO$_4$ (2.0 g, 12.6 mmol) solution was added at room temperature and the mixture was stirred for additional 1 h. The mixture was extracted with methylene chloride. The combined organic layers were washed with brine, dried (Na$_2$SO$_4$), filtered and concentrated to afford tert-butyl 9-azabicyclo[3.3.1]nonan-3-ylcarbamate (360 mg, 89%) as an off-white solid: $^1$H NMR (500 MHz, CDCl$_3$) δ 4.32 (br s, 1H), 3.66 (br s, 1H), 3.33-3.00 (m, 2H), 2.25-2.00 (m, 2H), 1.85-1.48 (m, 5H), 1.45 (s, 9H), 1.40-1.35 (m, 2H), 1.09-1.02 (m, 2H); MS (ESI+) m/z 241 (M+H).

Step C: Ethyl iodide (50 μL, 0.63 mmol) was added to a solution of the amine from Step B (100 mg, 0.42 mmol) in methylene chloride (2 mL) at 0° C. The mixture was allowed to warm to room temperature and stirred for 30 h. The mixture was quenched with a saturated solution of sodium bicarbonate and extracted with methylene chloride. The combined organic layers were washed with brine, dried (Na$_2$SO$_4$), filtered and concentrated. The crude material was purified by column chromatography (silica gel, 90:9:1 ethyl acetate/methanol/concentrated ammonium hydroxide) to afford tert-butyl 9-ethyl-9-azabicyclo[3.3.1]nonan-3-ylcarbamate (50 mg, 45%) as a white solid: $^1$H NMR (500 MHz, CDCl$_3$) δ 4.28 (br s, 1H), 3.99 (br s, 1H), 3.13-3.10 (m, 2H), 2.63 (q, J=7.0 Hz, 2H), 2.38-2.30 (m, 2H), 1.90-1.82 (m, 3H), 1.48-1.46 (m, 1H), 1.44 (s, 9H), 1.16-0.95 (m, 7H); MS (ESI+) m/z 269 (M+H).

Step D: Trifluoroacetic acid (0.5 mL) was added to a solution of tert-butyl 9-ethyl-9-azabicyclo[3.3.1]nonan-3-ylcarbamate from Step C (50 mg, 0.19 mmol) in methylene chloride (1 mL) at room temperature and the mixture was stirred under nitrogen for 2 h. The mixture was concentrated and the residue was dissolved in methanol (1 mL). HCl in diethyl ether (1.0 M, 2.0 mL, 2.0 mmol) was added dropwise at room temperature and the mixture was stirred for 5 min. The mixture was concentrated again and dried under vacuum overnight to give 9-ethyl-9-azabicyclo[3.3.1]nonan-3-amine dihydrochloride (45 mg, 99%) as a white solid: $^1$H NMR (500 MHz, DMSO-d$_6$) δ 9.75 (br s, 1H), 8.39 (br s, 3H), 4.14 (br s, 1H), 3.73-3.71 (m, 2H), 3.25 (q, J=7.0 Hz, 2H), 2.55-2.48 (m, 2H), 2.05-1.95 (m, 3H), 1.80-1.76 (m, 1H), 1.50-1.22 (m, 7H); MS (ESI+) m/z 169 (M+H).

Step E: A mixture of 2-cyclopropylbenzoxazole-4-carboxylic acid (38 mg, 0.19 mmol), 3-amino-9-ethyl-9-azabicyclo[3.3.1]nonane dihydrochloride from Step D (45 mg, 0.19 mmol), 1-ethyl-3-(3-dimethylaminopropyl)carbodiimide hydrochloride (72 mg, 0.38 mmol) and 1-hydroxybenzotriazole (51 mg, 0.38 mmol) in DMF (5 mL) was stirred under nitrogen at room temperature for 5 min, and then triethylamine (0.16 mL, 1.1 mmol) was added. The resulting reaction mixture was stirred at room temperature overnight, and then was quenched with a saturated solution of sodium bicarbonate, extracted with methylene chloride. The combined organic layers were washed with brine, dried (Na$_2$SO$_4$), filtered and concentrated. The crude material was purified by Combi-flash chromatography (silica gel, 90:9:1 ethyl acetate/methanol/concentrated ammonium hydroxide) to afford the amide (35 mg, 53%) as a light yellow solid: $^1$H NMR (500 MHz, CDCl$_3$) δ 8.91 (d, J=6.5 Hz, 1H), 8.11 (dd, J=7.5, 1.0 Hz, 1H), 7.53 (dd, J=7.5, 1.0 Hz, 1H), 7.34 (t, J=7.5 Hz, 1H), 4.60-4.50 (m, 1H), 3.24-3.20 (m, 2H), 2.73 (q, J=7.0 Hz, 2H), 2.60-2.50 (m, 2H), 2.30-1.90 (m, 4H), 1.60-1.13 (m, 9H), 1.06 (t, J=7.0 Hz, 3H); MS (ESI+) m/z 354 (M+H).

Step F: Hydrogen chloride in diethyl ether (1.0 M, 0.1 mL, 0.1 mmol) was added dropwise to a solution of the amide from Step E (35 mg, 0.1 mmol) in methylene chloride (1 mL) and diethyl ether (2 mL) at 0° C. The mixture was stirred for 5 min, and then diethyl ether (30 mL) was added. The resulting solid was filtered, washed with diethyl ether, and dried under vacuum overnight to afford N-(9-ethyl-9-azabicyclo[3.3.1]non-3-yl)-2-cyclopropylbenzoxazole-4-carboxamide hydrochloride (28 mg, 72%) as an off-white solid: $^1$H NMR (500 MHz, DMSO-d$_6$) δ 9.81 (br s, 0.4H), 9.13 (d, J=5.5 Hz, 1H), 9.12 (br s, 0.6H), 8.88 (d, J=6.5 Hz, 1H), 7.96-7.86 (m, 1H), 7.48-7.43 (m, 1H), 4.60-4.30 (m, 1H), 3.78-3.15 (m, 2H), 2.78 (q, J=7.0 Hz, 2H), 2.68-2.62 (m, 2H), 2.42-2.05 (m, 4H), 1.90-1.23 (m, 12H); MS (ESI+) m/z 354 (M+H); HPLC 96.9% (AUC), t$_R$=11.90 min.

Example 22

Preparation of (S)—N-(1-Azabicyclo[2.2.2]oct-3-yl)-benzoxazole-4-carboxamide Hydrochloride Step A: A mixture of 2-amino-3-hydroxybenzoic acid hydrobromide (300 mg, 1.28 mmol), triethyl orthoformate (0.85 mL, 5.1 mmol), pyridinium p-toluenesulfonate (64 mg, 0.26 mmol) and xylenes (15 mL) was refluxed for 4 h. The reaction mixture was cooled to room temperature and concentrated under reduced pressure to afford the benzoxazole-4-carboxylic acid (210 mg, quantitative) as a light yellow solid: $^1$H NMR (300 MHz, DMSO-d$_6$) δ 13.12 (s, 1H), 8.86 (s, 1H), 8.03 (dd, J=8.1, 0.9 Hz, 1H), 7.92 (dd, J=8.1, 0.9 Hz, 1H), 7.54 (t, J=8.1 Hz, 1H); MS (ESI+) m/z 164 (M+H).

Step B: A mixture of benzoxazole-4-carboxylic acid from Step A (110 mg, 0.64 mmol), (S)-(-)-3-aminoquinuclidine dihydrochloride (130 mg, 0.64 mmol), 1-ethyl-3-(3-dimethylaminopropyl)carbodiimide hydrochloride (245 mg, 1.28 mmol), 1-hydroxybenzotriazole (173 mg, 1.28 mmol) and DMF (5 mL) was stirred at room temperature for 5 min, then triethylamine (0.33 mL, 2.6 mmol) was added. The resulting reaction mixture was stirred at room temperature for 12 h. The mixture was diluted with dichloromethane (20 mL), and then washed with a saturated sodium bicarbonate (10 mL). The aqueous phase was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford the carboxamide (140 mg, 80%) as a white solid: $^1$H NMR (500 MHz, CDCl$_3$) δ 9.27 (d, J=5.0 Hz, 1H), 8.25-8.22 (m, 2H), 7.74 (d, J=8.0 Hz, 1H), 7.53 (t, J=8.0 Hz, 1H), 4.33-4.22 (m, 1H), 3.55-3.43 (m, 1H), 3.07-2.82 (m, 4H), 2.74 (dd, J=13.5, 4.5 Hz, 1H), 2.12-2.07 (m, 1H), 2.00-1.91 (m, 1H), 1.80-1.68 (m, 2H), 1.60-1.51 (m, 1H); MS (ESI+) m/z 272 (M+H).

Step C: To an ice-cold solution of the carboxamide from Step B (140 mg, 0.52 mmol) in dichloromethane (2 mL) and ethyl ether (1 mL) was added HCl (1 M solution in ethyl ether, 0.52 mL, 0.52 mmol). The mixture was stirred at room temperature for 5 min, and then diluted with anhydrous ethyl ether (20 mL). The mixture was left at room temperature for 2 h, and then the resulting precipitate was collected by filtration and washed with ethyl ether (20 mL). The solid was dried on vacuum to afford (S)—N-(1-azabicyclo[2.2.2]oct-3-yl)-benzoxazole-4-carboxamide hydrochloride (68 mg, 43%) as a white solid: $^1$H NMR (500 MHz, DMSO-$d_6$) δ 10.24 (br s, 1H), 9.12 (d, J=6.5 Hz, 1H), 9.07 (s, 1H), 8.04 (dd, J=8.0, 1.0 Hz, 1H), 7.95 (dd, J=8.0, 1.0 Hz, 1H), 7.61 (t, J=8.0 Hz, 1H), 4.42-4.37 (m, 1H), 3.78-3.70 (m, 1H), 3.40-3.15 (m, 5H), 2.28 (dd, J=6.0, 3.0 Hz, 1H), 2.19-2.10 (m, 1H), 1.98-1.85 (m, 3H); MS (ESI+) m/z 272 (M+H); HPLC 92.1% (AUC), $t_R$=10.64 min.

Example 23

Preparation of Endo-N-(9-methyl-9-azabicyclo [3.3.1]non-3-yl)-2-(1-acetylpiperidin-4-yl)benzoxazole-4-carboxamide Hydrochloride Step A: To a suspension of 2-amino-3-hydroxybenzoic acid hydrobromide (2.0 g, 8.5 mmol) in dichloromethane (25 mL) was added triethylamine (4.77 mL, 34.2 mmol) followed by 1-acetylpiperidine-4-carbonyl chloride hydrochloride (1.93 g, 8.55 mmol) at room temperature. The resulting reaction mixture was stirred at room temperature for 17 h. The reaction was quenched with aqueous 2 N HCl (50 mL). The reaction mixture was extracted with dichloromethane (3×250 mL). The combined organic phase was dried (Na$_2$SO$_4$), filtered and concentrated to afford a light yellow solid. The crude solid was dissolved in toluene (20 mL) and the solution was treated with p-toluenesulfonic acid monohydrate (2.08 g, 10.9 mmol). The reaction mixture was then heated to reflux under nitrogen for 10 h. The reaction was cooled to room temperature, poured into water (100 mL) and extracted with ethyl acetate (3×150 mL). The combined organic phase was washed with water (2×100 mL), brine, dried (Na$_2$SO$_4$), filtered and concentrated. The crude product was purified by column chromatography (silica gel, 9:1 to 7:3 ethyl acetate/methanol) to afford 2-(1-acetylpiperidin-4-yl)benzoxazole-4-carboxylic acid (524 mg, 21%) as a brown solid: $^1$H NMR (300 MHz, DMSO-$d_6$) δ 10.81 (br s, 1H), 7.48 (dd, J=7.7, 1.6 Hz, 1H), 6.94 (t, J=7.8 Hz, 1H), 6.89 (dd, J=7.7, 1.6 Hz, 1H), 4.45-4.34 (m, 2H), 3.92-3.82 (m, 2H), 3.18-3.05 (m, 1H), 2.07-2.02 (m, 2H), 2.02 (s, 3H), 1.92-1.82 (m, 2H); MS (ESI+) m/z 289 (M+H).

Step B: A mixture of 2-(1-acetylpiperidin-4-yl)benzoxazole-4-carboxylic acid (0.51 g, 1.77 mmol), endo-3-amino-9-methyl-9-azabicyclo[3.3.1]nonane dihydrochloride (0.44 g, 1.94 mmol), 1-ethyl-3-(3-dimethylaminopropyl)carbodiimide hydrochloride (0.68 g, 3.54 mmol) and 1-hydroxybenzotriazole (0.48 g, 3.54 mmol) in DMF (10 mL) was stirred under nitrogen at room temperature for 10 min, and then triethylamine (1.47 mL, 10.6 mmol) was added. The resulting reaction mixture was stirred at room temperature for 17 h, quenched with a saturated aqueous solution of sodium bicarbonate (15 mL), and then extracted with ethyl acetate (4×150 mL). The combined organic phase was washed with water (4×150 mL), brine (3×150 mL), and dried (Na$_2$SO$_4$), filtered and concentrated. The crude material was purified by column chromatography (silica gel, 90:9:1 dichloromethane/methanol/concentrated ammonium hydroxide) to afford the desired amide (300 mg, 40%) as an off-white solid: $^1$H NMR (500 MHz, CDCl$_3$) δ 8.85 (d, J=6.5 Hz, 1H), 8.17 (dd, J=7.9, 0.9 Hz, 1H), 7.61 (dd, J=7.9, 0.9 Hz, 1H), 7.43 (t, J=7.8 Hz, 1H), 4.65-4.52 (m, 2H), 3.97-3.90 (m, 1H), 3.37-3.25 (m, 2H), 3.18-3.10 (m, 2H), 3.02-2.95 (m, 1H), 2.65-2.57 (m, 2H), 3.55 (s, 3H), 2.30-2.20 (m, 2H), 2.16 (s, 3H), 2.10-1.90 (m, 5H), 1.60-1.44 (m, 3H), 1.22-1.14 (m, 2H); MS (ESI+) m/z 425 (M+H).

Step C: To a solution of the amide from step B (100 mg, 0.24 mmol) in dichloromethane (0.5 mL) was slowly added a solution of HCl in diethyl ether (1.0 N, 0.26 mL, 0.26 mmol) at 0° C. The reaction mixture was diluted with diethyl ether (200 mL). The resulting solid was filtered and washed with diethyl ether (100 mL) to afford of endo-N-(9-methyl-9-azabicyclo[3.3.1]non-3-yl)-2-(1-acetylpiperidin-4-yl)benzoxazole-4-carboxamide hydrochloride (76 mg, 70%) as an off-white solid: $^1$H NMR (500 MHz, CDCl$_3$) δ 12.27 (br s, 0.4H), 11.72 (br s, 0.6H), 9.24 (br s, 1H), 8.17 (d, J=7.7 Hz, 0.4H), 8.11 (d, J=7.7 Hz, 0.6H), 7.69 (d, J=8.0 Hz, 0.4H), 7.65 (d, J=8.0 Hz, 0.6H), 7.48 (t, J=7.8 Hz, 0.4H), 7.44 (t, J=7.8 Hz, 0.6H), 4.87-4.54 (m, 2H), 4.03-3.90 (m, 1H), 3.67-3.35 (m, 2H), 3.40-3.24 (m, 2H), 3.12-2.60 (m, 10H), 2.24-2.11 (m, 5H), 2.03-1.85 (m, 2H), 1.84-1.55 (m, 4H); MS (ESI+) m/z 425 (M+H); HPLC>99% (AUC), $t_R$=13.96 min. Anal. Calcd for $C_{24}H_{32}N_4O_3$·HCl·1.5H$_2$O: C, 59.04; H, 7.40; N, 11.41. Found: C, 59.12; H, 7.43; N, 11.46.

Example 24

Preparation of Endo-N-(9-methyl-9-azabicyclo [3.3.1]non-3-yl)-2-(tetrahydro-2H-pyran-4-yl)benzoxazole-4-carboxamide Hydrochloride Step A: To an ice-cold suspension of tetrahydro-2H-pyran-4-carboxylic acid (0.65 g, 5.0 mmol) in dichloromethane (20 mL) was added oxalyl chloride (0.47 mL, 5.0 mmol) dropwise followed by a few drops of anhydrous DMF. After the ice-water bath was removed, the mixture was stirred for 1 h. To the above solution was added 2-amino-3-hydroxybenzoic acid hydrobromide (1.17 g, 5.0 mmol) followed by triethylamine (2.09 mL, 15.0 mmol). The resulting reaction mixture was stirred at room temperature for 17 h. The reaction was quenched with 1 N HCl (20 mL) and extracted with dichloromethane. The aqueous phase was further extracted with dichloromethane (2×200 mL). The combined organic phase was washed with water (2×100 mL), dried (Na$_2$SO$_4$), filtered and concentrated to afford a light yellow solid. The crude solid was dissolved in toluene (10 mL) and the solution was treated with p-toluenesulfonic acid monohydrate (1.42 g, 7.46 mmol). The reaction mixture was then heated to reflux under nitrogen for 10 h. The reaction was cooled to room temperature, poured into water and extracted with ethyl acetate (2×250 mL). The organic phase was separated, washed with water, brine, dried (Na$_2$SO$_4$), filtered and concentrated to afford the 2-(tetrahydro-2H-pyran-4-yl)benzoxazole-4-carboxylic acid (590 mg, 49%) as a light brown solid: $^1$H NMR (500 MHz, DMSO-$d_6$) δ 12.90 (br s, 1H), 7.93 (dd, J=7.9, 1.0 Hz, 1H), 7.86 (dd, J=7.9, 1.0 Hz, 1H), 7.45 (t, J=7.9 Hz, 1H), 3.97-3.92 (m, 2H), 3.55-3.48 (m, 2H), 3.38-3.30 (m, 1H), 2.07-2.02 (m, 2H), 1.92-1.82 (m, 2H); MS (ESI+) m/z 248 (M+H).

Step B: A mixture of the 2-(tetrahydro-2H-pyran-4-yl)benzoxazole-4-carboxylic acid (290 mg, 1.17 mmol), endo-3-amino-9-methyl-9-azabicyclo[3.3.1]nonane dihydrochloride (334 mg, 1.47 mmol), 1-ethyl-3-(3-dimethylaminopropyl) carbodiimide hydrochloride (447 mg, 2.34 mmol) and 1-hydroxybenzotriazole (316 mg, 2.34 mmol) in DMF (5 mL) was stirred under nitrogen at room temperature for 10 min, and then triethylamine (0.49 mL, 3.51 mmol) was added. The resulting reaction mixture was stirred at room temperature for 17 h; the reaction was quenched with a saturated aqueous solution of sodium bicarbonate (10 mL), and then extracted with ethyl acetate (3×150 mL). The combined organic phase was washed with brine and dried (Na$_2$SO$_4$), filtered and concentrated. The crude material was purified by column chromatography (silica gel, 90:9:1 dichloromethane/methanol/concentrated ammonium hydroxide) to afford the desired amide (214 mg, 48%) as a white solid: $^1$H NMR (500 MHz, CDCl$_3$) δ 8.95 (br s, 1H), 8.17 (dd, J=7.9, 0.8 Hz, 1H), 7.74 (dd, J=7.9, 0.8 Hz, 1H), 7.51 (t, J=7.9 Hz, 1H), 4.61-4.51 (m, 1H), 4.15-4.08 (m, 2H), 3.65-3.60 (m, 2H), 3.32-3.26 (m, 1H), 3.18-3.10 (m, 2H), 2.65-2.55 (m, 5H), 2.17-1.95 (m, 7H), 1.56-1.42 (m, 3H), 1.18-1.09 (m, 2H); MS (ESI+) m/z 384 (M+H).

Step C: To a solution of the amide from step B (208 mg, 0.54 mmol) in methanol (1.5 mL) was slowly added a solution of HCl in diethyl ether (1 N, 0.6 mL, 0.6 mmol) at 0° C. The reaction mixture was diluted with diethyl ether (200 mL). The resulting solid was filtered and washed with diethyl ether (150 mL) to afford endo-N-(9-methyl-9-azabicyclo[3.3.1]non-3-yl)-2-(tetrahydro-2H-pyran-4-yl))benzoxazole-4-carboxamide hydrochloride (186 mg, 82%) as a white solid: $^1$H NMR (500 MHz, CDCl$_3$) δ 12.30 (br s, 0.4H), 11.83 (br s, 0.6H), 9.6 (d, J=4.6 Hz, 0.4H), 9.33-9.28 (m, 0.6H), 8.15 (d, J=7.8 Hz, 0.4H), 8.11 (d, J=7.8 Hz, 0.6H), 7.68 (d, J=8.0 Hz, 0.4H), 7.65 (d, J=8.0 Hz, 0.6H), 7.47 (t, J=8.0 Hz, 0.4H), 7.43 (t, J=8.0 Hz, 0.6H), 4.84-4.74 (m, 0.6H), 4.62-4.52 (m, 0.4H), 4.15-4.07 (m, 2H), 3.64-3.53 (m, 4H), 3.37-3.24 (m, 1H), 3.00-2.60 (m, 7H), 2.27-2.05 (m, 6H), 1.95-1.67 (m, 4H); MS (ESI+) m/z 384 (M+H); HPLC 98.5% (AUC), $t_R$=14.81 min. Anal. Calcd for $C_{22}H_{29}N_3O_3 \cdot HCl \cdot 0.5H_2O$: C, 61.60; H, 7.28; N, 9.80. Found: C, 61.45; H, 7.35; N, 9.73.

Example 25

Preparation of (S)—N-(1-Azabicyclo[2.2.2]oct-3-yl)-2-(tetrahydro-2H-pyran-4-yl)benzoxazole-4-carboxamide Hydrochloride Step A: A mixture of 2-(tetrahydro-2H-pyran-4-yl)benzoxazole-4-carboxylic acid (290 mg, 1.17 mmol), 1-ethyl-3-(3-dimethylaminopropyl)carbodiimide hydrochloride (447 mg, 2.34 mmol), 1-hydroxybenzotriazole (316 mg, 2.34 mmol) and (S)-(–)-3-aminoquinuclidine dihydrochloride (293 mg, 1.47 mmol) in DMF (5 mL) was stirred at room temperature for 10 min, then triethylamine (0.49 mL, 3.51 mmol) was added. The resulting reaction mixture was stirred at room temperature 17 h. The reaction mixture was diluted with ethyl acetate (50 mL), and then treated with a saturated aqueous solution of sodium bicarbonate (10 mL). The organic layer was isolated and the aqueous layer was further extracted with ethyl acetate (3×200 mL). The combined organics were washed with water (3×100 mL) and brine (2×100 mL), dried (Na$_2$SO$_4$), filtered and concentrated. The crude material was purified by column chromatography (silica gel, 90:9:1 dichloromethane/methanol/concentrated ammonium hydroxide) to afford the desired amide (221 mg, 53%) as an off-white solid: $^1$H NMR (500 MHz, CDCl$_3$) δ 9.45 (d, J=7.2 Hz, 1H), 8.15 (dd, J=7.9, 0.9 Hz, 1H), 7.63 (dd, J=7.9, 0.9 Hz, 1H), 7.43 (t, J=8.0 Hz, 1H), 4.32-4.25 (m, 1H), 4.12-4.06 (m, 2H), 3.66-3.58 (m, 2H), 3.52-3.45 (m, 1H), 3.30-3.25 (m, 1H), 3.03-2.96 (m, 2H), 2.94-2.85 (m, 2H), 2.78-2.73 (m, 1H), 2.20-2.12 (m, 2H), 2.10-1.95 (m, 4H), 1.78-1.73 (m, 2H), 1.66-1.55 (m, 1H); MS (ESI+) m/z 356 (M+H).

Step B: To a solution of the amide from Step A (217 mg, 0.61 mmol) in methanol (1.5 mL) was slowly added a solution of HCl in diethyl ether (1 N, 0.67 mL, 0.67 mmol) at 0° C. The reaction mixture was diluted with diethyl ether (200 mL). The resulting solid was filtered and washed with diethyl ether (250 mL) to afford (S)—N-(1-azabicyclo[2.2.2]oct-3-yl)-2-(tetrahydro-2H-pyran-4-yl)benzoxazole-4-carboxamide hydrochloride (206 mg, 83%) as a white solid: $^1$H NMR (500 MHz, CDCl$_3$) δ 12.70 (br s, 1H), 9.47 (d, J=7.2 Hz, 1H), 8.13 (d, J=7.7 Hz, 1H), 7.69 (d, J=7.9 Hz, 1H), 7.47 (t, J=7.9 Hz, 1H), 4.68-4.62 (m, 1H), 4.18-4.10 (m, 2H), 3.79 (t, J=10.2 Hz, 1H), 3.62 (t, J=11.3 Hz, 2H), 3.45-3.18 (m, 6H), 2.55-2.50 (m, 1H), 2.35-2.28 (m, 1H), 2.15-1.95 (m, 6H), 1.75-1.65 (m, 1H); MS (ESI+) m/z 356 (M+H); HPLC 98.6% (AUC), $t_R$=13.32 min. Anal. Calcd for $C_{20}H_{25}N_3O_3 \cdot HCl \cdot 0.5H_2O$: C, 59.92; H, 6.79; N, 10.48; Cl, 8.84. Found: C, 59.61; H, 6.95; N, 10.49; Cl, 8.83.

Example 26

Preparation of Endo-N-(9-Methyl-9-azabicyclo[3.3.1]nonan-3-yl)-2-(quinuclidin-4-yl)benzoxazole-4-carboxamide Dihydrochloride Step A: A mixture of 4-cyano-quinuclidine (0.95 g, 6.97 mmol), and methylene chloride (20 mL) was stirred, and cooled to −78° C. Diisobutylaluminum hydride (1 M solution in hexanes, 17.4 mmol, 17.4 mL) was added dropwise to the reaction mixture and stirring continued 2 h. The reaction was quenched with a saturated aqueous solution of Rochelle's salt (sodium potassium tartrate 10 mL) and the reaction was allowed to warm to room temperature. The aqueous phase was extracted with methylene chloride (2×20 mL), the combined organic phase was washed with water and dried (Na$_2$SO$_4$), concentrated to afforded crude quinuclidine-4-carbaldehyde as a white solid (0.57 g, 55%). The crude product was used without further purification: $^1$H NMR (500 MHz, CDCl$_3$) δ 9.38 (s, 1H), 2.96-2.92 (m, 6H), 1.62-1.53 (m, 6H).

Step B: A mixture of quinuclidine-4-carbaldehyde (0.57 g, 4.10 mmol), piperidine (0.86 g, 1 mL, 10.10 mmol), methyl 2-amino-3-hydroxybenzoate (0.68 g, 4.10 mmol) and methanol (10 mL) was heated to reflux for 40 h. Analysis by LCMS indicated the presence of the requisite intermediate Schiff base. The solvent was removed under reduced pressure, the residue was dissolved in methylene chloride (20 ml) and silver (I) oxide (1.23 g, 5.34 mmol) was added. The reaction mixture was stirred at room temperature for 5 h. Analysis by LCMS indicated consumption of the Schiff base intermediate. The reaction mixture was filtered though diatomaceous earth (10 g) eluting with methylene chloride (50 mL) and concentrated. The crude product was purified by column chromatography (silica gel, 5 to 20% methanol in chloroform) to afford methyl 2-(quinuclidin-4-yl)benzoxazole-4-carboxylate (250 mg, 17%) as an brown solid: $^1$H NMR (300 MHz, CDCl$_3$) δ 7.96 (dd, J=8.0, 1.0 Hz, 1H), 7.67 (dd, J=8.0, 1.0 Hz, 1H), 7.37 (d, d, J=8.0 Hz, 1H), 4.01 (s, 3H), 3.06-3.02 (m, 6H), 2.06-2.01 (m, 6H); MS (ESI+) m/z 287 (M+H).

Step C: A mixture of methyl 2-(quinuclidin-4-yl)benzoxazole-4-carboxylate (233 mg, 0.81 mmol), lithium hydroxide monohydrate (51 mg, 1.22 mmol) and THF/water (2:1, 15 mL) was stirred at room temperature for 6 h. The reaction mixture was concentrated, and washed with brine (10 mL), the precipitate which formed was filtered, washed with hexanes and dried to afford 2-(quinuclidin-4-yl)benzoxazole-4-carboxylic acid (240 mg, 108%) as a brown solid: $^1$H NMR (500 MHz, DMSO-d$_6$) δ 7.80 (d, J=8.0 Hz, 1H), 7.67 (d, J=8.0 Hz, 1H), 7.31 (d, J=8.0 Hz, 1H), 2.83-2.81 (m, 6H), 1.89-1.84 (m, 6H); MS (ESI+) m/z 273 (M+H).

Step D: A mixture of 2-(quinuclidin-4-yl)benzoxazole-4-carboxylic acid (221 mg, 0.81 mmol), endo-3-amino-9-methyl-9-azabicyclo[3.3.1]nonane dihydrochloride (221 mg, 0.97 mmol), 1-ethyl-3-(3-dimethylaminopropyl)carbodiimide hydrochloride (311 mg, 1.62 mmol), 1-hydroxybenzotriazole (219 mg, 1.62 mmol) and DMF (5 mL) was stirred at room temperature for 5 min, then triethylamine (0.47 mL, 3.40 mmol) was added. The resulting reaction mixture was stirred at room temperature for 40 h. The mixture was diluted with ethyl acetate (30 mL), and then washed with a saturated sodium bicarbonate (10 mL). The aqueous phase was further extracted with dichloromethane (3×15 mL). The combined organic phase was dried ($Na_2SO_4$), filtered and concentrated. The crude material was purified by column chromatography (silica gel, 100% dichloromethane to 100% 90:9:1 dichloromethane/methanol/concentrated ammonium hydroxide) to afford the requisite carboxamide (94 mg, 28%) as an off-white solid: $^1$H NMR (500 MHz, $CDCl_3$) δ 8.99 (d, J=7.0 Hz, 1H), 8.16 (dd, J=8.0, 1.0 Hz, 1H), 7.65-7.57 (m, 1H), 7.40 (t, J=8.0 Hz, 1H), 4.53-4.51 (m, 1H), 3.15-3.05 (m, 7H), 2.63-2.53 (m, 2H), 2.51 (s, 3H), 2.15-1.95 (m, 7H) 1.72-1.50 (m, 4H), 1.50-1.38 (m, 2H), 1.16-1.04 (m, 2H); MS (ESI+) m/z 409 (M+H).

Step E: To an ice-cold solution of the carboxamide from Step D (94 mg, 0.23 mmol) in dichloromethane (3 mL) was added HCl (1 M solution in ethyl ether, 0.69 mL, 0.69 mmol). The mixture was stirred at room temperature for 1 h, and then diluted with anhydrous ethyl ether (20 mL). The mixture was left at room temperature for 1 h, and then the resulting precipitate was collected by filtration and washed with ethyl ether (20 mL). The solid was dried under vacuum to afford endo-N-(9-methyl-9-azabicyclo[3.3.1]non-3-yl)-2-(quinuclidin-4-yl)benzoxazole-4-carboxamide dihydrochloride (90 mg, 77%) as a white solid: $^1$H NMR (500 MHz, DMSO-$d_6$) δ 10.82-10.70 (m, 1.3H), 10.02-9.90 (br s, 0.5H), 9.07-9.05 (m, 0.4H), 8.82-8.70 (m, 0.6H), 8.00-7.90 (m, 2H), 7.60-7.52 (m, 1H), 4.64-4.56 (m, 0.6H), 4.42-4.36 (m, 0.4H), 3.68-3.60 (m, 1H), 3.58-3.52 (m, 1H), 3.48-3.38 (m, 6H), 2.83 (s, 3H), 2.76-2.60 (m, 2H), 2.38-2.20 (m, 7H), 2.18-2.06 (m, 2H), 1.88-1.72 (m, 3H), 1.68-1.44 (m, 2H); MS (ESI+) m/z 408 (M+H); HPLC 98.3% (AUC), $t_R$=12.93 min. Anal. Calcd for $C_{24}H_{32}N_4O_2 \cdot 1.75HCl \cdot 2H_2O$: C, 56.70; H, 7.48; N, 11.02. Found: C, 56.88; H, 7.38; N, 11.12.

Example 27

Preparation of Endo-N-(9-methyl-9-azabicyclo[3.3.1]non-3-yl)-2-(piperidin-4-yl)benzoxazole-4-carboxamide Dihydrochloride Step A: A mixture of 1-(tert-butoxycarbonyl)piperidin-4-carboxylic acid (2.47 g, 10.78 mmol), 1-ethyl-3-(3-dimethylaminopropyl)carbodiimide hydrochloride (3.43 g, 17.96 mmol), 1-hydroxybenzotriazole (2.42 g, 17.96 mmol) and methyl 2-amino-3-hydroxybenzoate (1.50 g, 8.98 mmol) in dichloromethane (25 mL) was stirred under nitrogen at room temperature for 10 min, and then triethylamine (1.47 mL, 10.6 mmol) was added. The resulting reaction mixture was stirred at room temperature for 5 h, the reaction was quenched with a saturated aqueous solution of sodium bicarbonate (15 mL), and then extracted with dichloromethane (2×150 mL). The combined organic phase was washed with water (2×100 mL), brine (2×100 mL), and dried ($Na_2SO_4$), filtered and concentrated to afford a light yellow solid. The crude solid was dissolved in toluene (20 mL) and the solution was treated with p-toluenesulfonic acid monohydrate (2.08 g, 10.9 mmol). The reaction mixture was then heated to reflux under nitrogen for 4 h. The reaction was cooled to room temperature and concentrated. The crude product was purified by column chromatography (silica gel, 90:9:1 dichloromethane/methanol/concentrated ammonium hydroxide) to afford 2-(piperidin-4-yl)benzoxazole-4-carboxylate methyl ester (1.64 mg, 70%) as an off-white solid: $^1$H NMR (500 MHz, $CDCl_3$) δ 7.99 (dd, J=7.8, 0.9 Hz, 1H), 7.78 (dd, J=7.8, 0.9 Hz, 1H), 7.39 (t, J=7.8 Hz, 1H), 4.00 (s, 3H), 3.52-3.45 (m, 2H), 3.36-3.30 (m, 1H), 3.10-3.03 (m, 2H), 2.33-2.20 (m, 4H); MS (ESI+) m/z 261 (M+H).

Step B: A mixture of the 2-(piperidin-4-yl)benzoxazole-4-carboxylate methyl ester (1.64 g, 6.3 mmol), di-tert-butyldicarbonate (1.72 g, 7.87 mmol) and DMAP (153 mg, 1.26 mmol) in dichloromethane (50 mL) was stirred at room temperature for 3 h, the reaction was quenched with a saturated aqueous solution of sodium bicarbonate (10 mL), and then extracted with dichloromethane (2×100 mL). The combined organic phase was washed with water (2×75 mL), brine (2×75 mL), and dried ($Na_2SO_4$), filtered and concentrated. The crude material was purified by column chromatography (silica gel, 3:2, hexanes/ethyl acetate) to afford 2-(1-(tert-butoxycarbonyl)piperidin-4-yl)benzoxazole-4-carboxylate methyl ester (1.30 g, 58%) as a white solid: $^1$H NMR (300 MHz, $CDCl_3$) δ 7.98 (dd, J=7.8, 0.9 Hz, 1H), 7.69 (dd, J=7.8, 0.9 Hz, 1H), 7.38 (t, J=7.8 Hz, 1H), 4.26-4.22 (m, 2H), 4.02 (s, 3H), 3.30-3.18 (m, 1H), 3.00-2.90 (m, 2H), 2.20-2.10 (m, 2H), 2.03-1.90 (m, 2H), 1.48 (s, 9H); MS (ESI+) m/z 361 (M+H Step C: A mixture of the 2-(1-(tert-butoxycarbonyl)piperidin-4-yl)benzoxazole-4-carboxylate methyl ester (1.30 g, 3.60 mmol) was treated with lithium hydroxide mono hydrate (0.23 g, 5.42 mmol) in a mixture of tetrahydrofuran (15 mL) and water (5 mL). The reaction mixture was stirred under nitrogen at room temperature for 6 h, cooled to 0° C., adjusted to pH 6, and then extracted with dichloromethane (4×150 mL). The combined organic phase was washed with water (4×150 mL), brine (3×150 mL), and dried ($Na_2SO_4$), filtered and concentrated to afford the desired acid (1.20 g, 96%) as a white solid: $^1$H NMR (500 MHz, $CDCl_3$) δ 7.98 (dd, J=7.8, 0.9 Hz, 1H), 7.69 (dd, J=7.8, 0.9 Hz, 1H), 7.38 (t, J=7.8 Hz, 1H), 4.30-4.15 (m, 2H), 3.26-3.18 (m, 1H), 3.10-2.90 (m, 2H), 2.25-2.15 (m, 2H), 1.95-1.85 (m, 2H), 1.49 (s, 9H), 1.40-1.20 (m, 2H); MS (ESI+) m/z 347 (M+H).

Step D: A mixture of the 2-(1-(tert-butoxycarbonyl)piperidin-4-yl)benzoxazole-4-carboxylic acid (0.60 g, 1.73 mmol), endo-3-amino-9-methyl-9-azabicyclo[3.3.1]nonane dihydrochloride (0.47 g, 2.08 mmol), 1-ethyl-3-(3-dimethylaminopropyl)carbodiimide hydrochloride (0.66 g, 3.46 mmol) and 1-hydroxybenzotriazole (0.47 g, 3.46 mmol) in DMF (10 mL) was stirred under nitrogen at room temperature for 10 min, and then triethylamine (0.72 mL, 5.19 mmol) was added. The resulting reaction mixture was stirred at room temperature for 17 h, quenched with a saturated aqueous solution of sodium bicarbonate (15 mL), and then extracted with ethyl acetate (4×200 mL). The combined organic phase was washed with water (4×200 mL), brine (3×150 mL), and dried ($Na_2SO_4$), filtered and concentrated. The crude material was purified by column chromatography (silica gel, 90:9:1 dichloromethane/methanol/concentrated ammonium hydroxide) to afford the desired amide (480 mg, 57%) as an off-white solid: $^1$H NMR (500 MHz, $CDCl_3$) δ 8.93 (br s, 1H), 8.17 (d, J=7.8 Hz, 1H), 7.61 (d, J=7.8 Hz, 1H), 7.42 (t, J=7.8 Hz, 1H), 4.65-4.50 (m, 1H), 4.25-4.10 (m, 2H), 3.25-3.00 (m, 5H), 2.75-2.50 (m, 5H), 2.25-1.90 (m, 7H), 1.64-1.50 (m, 3H), 1.47 (s, 9H); MS (ESI+) m/z 483 (M+H).

Step E: To a solution of the amide from step D (471 mg, 0.98 mmol) in dichloromethane (0.5 mL) added a solution of HCl in dioxane dropwise (4.0 N, 1.23 mL, 4.90 mmol) at 0° C. and stirred for 2 h. The reaction mixture was concentrated and dissolved in methanol (5 mL), and then diluted with diethyl ether (250 mL). The resulting solid was filtered and washed with diethyl ether (300 mL) to afford endo-N-(9-methyl-9-azabicyclo[3.3.1]non-3-yl)-2-(piperidin-4-yl)benzoxazole-4-carboxamide dihydro chloride (306 mg, 69%) as a white solid: $^1$H NMR (500 MHz, DMSO-d$_6$) δ 10.54 (br s, 0.4H), 9.80 (br s, 0.6H), 9.22 (br s, 0.6H), 9.15 (br s, 0.4H), 9.11 (d, J=5.3 Hz, 0.4H), 8.83 (d, J=6.6 Hz, 0.6H), 8.00-7.90 (m, 2H), 7.60-7.50 (m, 1H), 4.65-4.55 (m, 0.6H), 4.45-4.35 (m, 0.4H), 3.70-3.62 (m, 1H), 3.60-3.50 (m, 2H), 3.47-3.40 (m, 2H), 3.40-3.24 (m, 2H), 3.15-3.05 (m, 2H), 2.85-2.80 (m, 3H), 2.75-2.60 (m, 2H), 2.35-2.23 (m, 3H), 2.20-2.05 (m, 4H), 1.85-1.75 (m, 2H), 1.55-1.49 (m, 2H); MS (ESI+) m/z 383 (M+H); HPLC>99% (AUC), t$_R$=11.28 min. Anal. Calcd for C$_{22}$H$_{30}$N$_4$O$_2$.2.2HCl.0.5H$_2$O: C, 56.02; H, 7.02; N, 11.88; Cl, 16.53. Found: C, 56.33; H, 7.39; N, 11.84; Cl 16.13.

Example 28

Preparation of (S)—N-(1-Azabicyclo[2.2.2]oct-3-yl)-2-(piperidin-4-yl)benzoxazole-4-carboxamide Dihydrochloride Step A: A mixture of 2-(1-(tert-butoxycarbonyl)piperidin-4-yl)benzoxazole-4-carboxylic acid (0.60 g, 1.73 mmol), 1-ethyl-3-(3-dimethylaminopropyl)carbodiimide hydrochloride (66 g, 3.46 mmol), 1-hydroxybenzotriazole (0.47 g, 3.46 mmol) and (S)-(-)-3-aminoquinuclidine dihydrochloride (0.41 g, 2.08 mmol) in DMF (10 mL) was stirred at room temperature for 10 min, then triethylamine (0.72 mL, 5.19 mmol) was added. The resulting reaction mixture was stirred at room temperature 17 h. The reaction mixture was diluted with ethyl acetate (50 mL), and then treated with a saturated aqueous solution of sodium bicarbonate (20 mL). The organic phase was separated and the aqueous layer was further extracted with ethyl acetate (3×200 mL). The combined organics were washed with water (3×100 mL) and brine (2×100 mL), dried (Na$_2$SO$_4$), filtered and concentrated. The crude material was purified by column chromatography (silica gel, 90:9:1 dichloromethane/methanol/concentrated ammonium hydroxide) to afford the desired amide (361 mg, 50%) as a white solid: $^1$H NMR (500 MHz, CDCl$_3$) δ 9.43 (d, J=7.4 Hz, 1H), 8.15 (dd, J=7.7, 0.9 Hz, 1H), 7.63 (dd, J=7.7, 0.9 Hz, 1H), 7.43 (t, J=8.0 Hz, 1H), 4.38-4.28 (m, 1H), 4.20-4.10 (m, 2H), 3.55-3.47 (m, 1H), 3.25-3.15 (m, 1H), 3.10-2.90 (m, 6H), 2.85-2.75 (m, 1H), 2.26-2.12 (m, 3H), 2.05-1.60 (m, 6H), 1.49 (s, 9H); MS (ESI+) m/z 455 (M+H).

Step B: To a solution of the amide from Step A (60 mg, 0.13 mmol) in dichloromethane (1.0 mL) was slowly added a solution of HCl in dioxane (4 N, 0.33 mL, 1.32 mmol) and stirred at 0° C. for 1 h The reaction mixture was concentrated dissolved in methanol (2 mL) and then diluted with diethyl ether. The resulting solid was filtered and washed with diethyl ether (300 mL) to afford (S)—N-(1-azabicyclo[2.2.2]oct-3-yl)-2-(piperidin-4-yl)benzoxazole-4-carboxamide dihydrochloride (41 mg, 71%) as a white solid: $^1$H NMR (500 MHz, DMSO-d$_6$) δ 10.46 (br s, 1H), 9.21 (d, J=6.5 Hz, 1H), 9.09 (br s, 1H), 7.96 (d, J=7.9 Hz, 1H), 7.69 (d, J=7.9 Hz, 1H), 7.47 (t, J=7.9 Hz, 1H), 4.46-4.40 (m, 1H), 3.75 (t, J=10.2 Hz, 1H), 3.58-3.50 (m, 1H), 3.40-3.34 (m, 3H), 3.30-3.20 (m, 2H), 3.19-3.08 (m, 4H), 2.40-2.26 (m, 4H), 2.21-2.10 (m, 3H), 1.97-1.88 (m, 3H); MS (ESI+) m/z 355 (M+H); HPLC>99% (AUC), t$_R$=14.24 min. Anal. Calcd for C$_{20}$H$_{26}$N$_4$O$_2$.2.5HCl.2.5H$_2$O: C, 49.03; H, 6.87; N, 11.40. Found: C, 49.05; H, 6.65; N, 11.31.

Example 29

Preparation of Endo-N-(9-methyl-9-azabicyclo[3.3.1]non-3-yl)-2-(1-methylpiperidin-4-yl)benzoxazole-4-carboxamide Dihydrochloride Step A: To a solution of endo-N-(9-methyl-9-azabicyclo[3.3.1]non-3-yl)-2-(piperidin-4-yl)benzoxazole-4-carboxamide (79 mg, 0.2 mmol) in methanol (3 mL) was added 37% formaldehyde (0.05 mL, 0.6 mmol) at room temperature. The resulting mixture was stirred for 17 h. To the above solution was added sodium borohydride (40 mg, 1.0 mmol) at 0° C. The resulting reaction mixture was stirred at room temperature for 3 h. The reaction was quenched with water (2 mL) and extracted with dichloromethane (3×50 mL). The combined organic phase was washed with water (2×20 mL), dried (Na$_2$SO$_4$), filtered and concentrated to afford an off-white solid. The crude material was purified by column chromatography (silica gel, 90:9:1 dichloromethane/methanol/concentrated ammonium hydroxide) to afford the desired amide (68 mg, 82%) as a white solid: $^1$H NMR (500 MHz, CDCl$_3$) δ 8.95 (d, J=7.2 Hz, 1H), 8.16 (dd, J=7.8, 0.9 Hz, 1H), 7.59 (dd, J=7.8, 0.9 Hz, 1H), 7.43 (t, J=8.0 Hz, 1H), 4.58-4.50 (m, 1H), 3.12-3.07 (m, 2H), 3.02-2.95 (m, 2H), 2.64-2.55 (m, 2H), 3.52 (s, 3H), 2.35 (s, 3H), 2.25-2.15 (m, 4H), 2.12-1.95 (m, 5H), 1.65-1.54 (m, 2H), 1.45-1.38 (m, 2H), 1.15-1.10 (m, 2H); MS (ESI+) m/z 397 (M+H).

Step B: To a solution of the amide from step A (68 mg, 0.17 mmol) in dichloromethane (2 mL) was slowly added a solution of HCl in diethyl ether (1 N, 0.36 mL, 0.36 mmol) at 0° C. The reaction mixture was diluted with diethyl ether (100 mL). The resulting solid was filtered and washed with diethyl ether (150 mL) to afford endo-N-(9-methyl-9-azabicyclo[3.3.1]non-3-yl)-2-(1-methylpiperidin-4-yl)benzoxazole-4-carboxamide dihydrochloride (63 mg, 79%) as a white solid: $^1$H NMR (500 MHz, DMSO-d$_6$) δ 11.04 (br s, 1H), 10.53 (br s, 0.4H), 9.79 (br s, 0.6H), 9.14 (br s, 0.4H), 8.87 (br s, 0.6H), 8.02-7.90 (m, 2H), 7.60-7.50 (m, 1H), 4.65-4.55 (m, 0.6H), 4.42-4.35 (m, 0.4H), 3.70-3.35 (m, 6H), 3.20-3.04 (m, 2H), 2.83 (s, 3H), 2.78-2.58 (m, 5H), 2.41-2.05 (m, 7H), 1.90-1.73 (m, 2H), 1.68-1.45 (m, 2H); MS (ESI+) m/z 397 (M+H); HPLC>99% (AUC), t$_R$=12.06 min. Anal. Calcd for C$_{23}$H$_{32}$N$_4$O$_2$.2HCl. 3H$_2$O: C, 52.77; H, 7.70; N, 10.70. Found: C, 52.60; H, 7.66; N, 10.60.

Example 30

Preparation of (S)—N-(1-Azabicyclo[2.2.2]oct-3-yl)-2-(1-methylpiperidin-4-yl)benzoxazole-4-carboxamide Dihydrochloride Dihydrochloride Step A: To a solution of endo-N-(9-methyl-9-azabicyclo[3.3.1]non-3-yl)-2-(piperidin-4-yl)benzoxazole-4-carboxamide (78 mg, 0.21 mmol) in methanol (3 mL) was added 37% formaldehyde (0.05 mL, 0.6 mmol) at room temperature. The resulting mixture was stirred for 17 h. To the above solution was added sodium borohydride (42 mg, 1.1 mmol) at 0° C. The resulting reaction mixture was stirred at room temperature for 3 h. The reaction was quenched with water (2 mL) and extracted with dichloromethane (3×50 mL). The combined organic phase was washed with water (2×20 mL), dried (Na$_2$SO$_4$), filtered and concentrated to afford an off-white solid. The crude material was purified by column chromatography (silica gel, 90:9:1 dichloromethane/methanol/concentrated ammonium hydroxide) to afford the desired methylated amine (56 mg, 72%) as a white solid: $^1$H NMR (500 MHz, CDCl$_3$) δ 9.51 (d, J=7.3 Hz, 1H), 8.15 (dd, J=7.9, 0.9

Hz, 1H), 7.62 (dd, J=7.9, 0.9 Hz, 1H), 7.42 (t, J=8.0 Hz, 1H), 4.28-4.23 (m, 1H), 3.50-3.45 (m, 1H), 3.10-2.85 (m, 7H), 2.78-2.72 (m, 1H), 2.34 (s, 3H), 2.27-2.17 (m, 4H), 2.10-1.95 (m, 4H), 1.76-1.70 (m, 2H), 1.60-1.52 (m, 1H); MS (ESI+) m/z 369 (M+H).

Step B: To a solution of the amine from Step A (56 mg, 0.15 mmol) in methanol (1.5 mL) was slowly added a solution of HCl in diethyl ether (1 N, 0.32 mL, 0.32 mmol) at 0° C. The reaction mixture was diluted with diethyl ether (150 mL). The resulting solid was filtered and washed with diethyl ether (100 mL) to afford (S)—N-(1-azabicyclo[2.2.2]oct-3-yl)-2-(1-methylpiperidin-4-yl)benzoxazole-4-carboxamide dihydrochloride (63 mg, 86%) as a white solid: $^1$H NMR (500 MHz, DMSO-$d_6$) δ 10.96 (br s, 0.7H), 10.71 (br s, 0.3H), 10.28 (br s, 1H), 9.25 (d, J=7.7 Hz, 1H), 7.97 (d, J=7.7 Hz, 1H), 7.91 (d, J=7.7 Hz, 1H), 7.47 (t, J=8.0 Hz, 1H), 4.46-4.40 (m, 1H), 3.75 (t, J=11.9 Hz, 1H), 3.55-3.35 (m, 5H), 3.30-3.10 (m, 6H), 2.76 (s, 3H), 2.45-2.35 (m, 2H), 2.30-2.10 (m, 3H), 2.00-1.95 (m, 3H); MS (ESI+) m/z 369 (M+H); HPLC 97.9% (AUC), $t_R$=11.66 min. Anal. Calcd for $C_{21}H_{28}N_4O_2 \cdot 2HCl \cdot 2.5H_2O$: C, 51.78; H, 7.25; N, 11.52. Found: C, 51.61; H, 7.17; N, 11.79.

Example 31

Preparation of (S)—N-(1-Azabicyclo[2.2.2]oct-3-yl)-2-(1-acetylpiperidin-4-yl)benzoxazole-4-carboxamide Hydrochloride Step A: To a slurry of (S)—N-(1-azabicyclo[2.2.2]oct-3-yl)-2-(piperidin-4-yl)benzoxazole-4-carboxamide (35 mg. 0.1 mmol) in acetonitrile (3 mL) was added cesium carbonate (40 mg, 0.30 mmol). The resulting reaction mixture was stirred at room temperature for 30 min, and then acetyl chloride (0.03 mL, 0.4 mmol) was added. The resulting reaction mixture was stirred at room temperature for 17 h. The reaction was quenched with water (2 mL), and then extracted with dichloromethane (3×50 mL). The combined organics were washed with brine (1×25 mL), dried (Na$_2$SO$_4$), filtered and concentrated. The crude material was purified by preparative TLC (90:9:1 dichloromethane/methanol/concentrated ammonium hydroxide) to afford the desired amide (31 mg, 77%) as a white solid: $^1$H NMR (500 MHz, CDCl$_3$) δ 9.38 (d, J=7.4 Hz, 1H), 8.16 (dd, J=7.7, 0.9 Hz, 1H), 7.64 (dd, J=7.7, 0.9 Hz, 1H), 7.45 (t, J=8.0 Hz, 1H), 4.65-4.55 (m, 1H), 4.30-4.22 (m, 1H), 4.00-3.95 (m, 1H), 3.55-3.20 (m, 3H), 3.05-2.95 (m, 5H), 2.85-2.75 (m, 1H), 2.26-2.12 (m, 3H), 2.15 (s, 3H), 2.10-1.85 (m, 4H), 1.75-1.65 (m, 2H); MS (ESI+) m/z 397 (M+H).

Step B: To a solution of the amide from Step A (31 mg, 0.08 mmol) in methanol (1.0 mL) was slowly added HCl (1 N in diethyl ether, 0.16 mL, 0.16 mmol) and stirred at 0° C. for 1 h. The compound mixture was concentrated and purified by reverse phase HPLC (100% water containing 0.05% trifluoroacetic acid (TFA) and 100% water containing 0.05% TFA). The solid obtained was treated with a solution of HCl in diethyl ether (1 N, 0.04 mL, 0.04 mmol) to afford (S—N-(1-azabicyclo[2.2.2]oct-3-yl)-2-(1-acetylpiperidin-4-yl)benzoxazole-4-carboxamide hydrochloride (16 mg, 47%) as a white solid: $^1$H NMR (500 MHz, DMSO-$d_6$) δ 10.00 (br s, 1H), 9.28 (d, J=7.4 Hz, 1H), 7.96 (d, J=7.7, Hz, 1H), 7.90 (d, J=7.7 Hz, 1H), 7.53 (t, J=8.0 Hz, 1H), 4.45-4.38 (m, 1H), 4.30-4.25 (m, 1H), 3.90-3.82 (m, 1H), 3.75 (t, J=11.0 Hz, 1H), 3.48-3.40 (m, 1H), 3.35-3.15 (m, 6H), 3.00-2.90 (m, 1H), 2.30-2.12 (m, 4H), 2.03 (s, 3H), 2.00-1.65 (m, 5H); MS (ESI+) m/z 397 (M+H); HPLC 95.2% (AUC), $t_R$=14.24 min.

Example 32

Preparation of N-(9-methyl-3-oxa-9-azabicyclo[3.3.1]non-7-yl)-2-(cyclopentyl-4-yl)benzoxazole-4-carboxamide Hydrochloride Step A: A mixture of the 2-cyclopentylbenzoxazole-4-carboxylic acid (70 mg, 0.30 mmol), 7-amino-9-methyl-3-oxa-9-azabicyclo[3.3.1]nonane dihydrochloride (83 mg, 0.36 mmol), 1-ethyl-3-(3-dimethylaminopropyl)carbodiimide hydrochloride (115 mg, 0.60 mmol) and 1-hydroxybenzotriazole (81 mg, 0.60 mmol) in DMF (4 mL) was stirred under nitrogen at room temperature for 10 min, and then triethylamine (0.15 mL, 1.20 mmol) was added. The resulting reaction mixture was stirred at room temperature for 17 h. The reaction was quenched with a saturated aqueous solution of sodium bicarbonate (10 mL), and then extracted with ethyl acetate (3×50 mL). The combined organic phase was washed with water (2×50 mL) brine (1×50 mL) and dried (Na$_2$SO$_4$), filtered and concentrated. The crude material was purified by column chromatography (silica gel, 90:9:1 dichloromethane/methanol/concentrated ammonium hydroxide) to afford the desired amide (63 mg, 57%) as a white solid: $^1$H NMR (500 MHz, CDCl$_3$) δ 9.95 (d, J=8.9 Hz, 1H), 8.09 (dd, J=7.8, 1.0 Hz, 1H), 7.56 (dd, J=7.8, 1.0 Hz, 1H), 7.36 (t, J=7.8 Hz, 1H), 4.86-4.75 (m, 1H), 4.00-3.92 (m, 2H), 3.87-3.82 (m, 2H), 2.70-2.65 (m, 2H), 2.60-2.50 (m, 5H), 2.20-2.05 (m, 4H), 1.90-1.70 (m, 5H), 1.65-1.56 (m, 2H); MS (ESI+) m/z 370 (M+H).

Step B: To a solution of the amide from step B (63 mg, 0.17 mmol) in dichloromethane (1.5 mL) was slowly added a solution of HCl in diethyl ether (1 N, 0.19 mL, 0.6 mmol) at 0° C. The reaction mixture was diluted with diethyl ether (200 mL). The resulting solid was filtered and washed with diethyl ether (300 mL) to afford N-(9-methyl-3-oxa-9-azabicyclo[3.3.1]non-7-yl)-2-(cyclopentyl-4-yl)benzoxazole-4-carboxamide hydrochloride (61 mg, 83%) as a white solid: $^1$H NMR (500 MHz, DMSO-$d_6$) δ 11.28 (br s, 0.6H), 10.82 (br s, 0.4H), 9.82-9.75 (m, 1H), 7.94 (d, J=7.8 Hz, 1H), 7.75 (d, J=7.8 Hz, 1H), 7.47 (t, J=7.8 Hz, 1H), 4.70-4.64 (m, 1H), 4.30-4.20 (m, 2H), 4.08-4.02 (m, 1.2H), 3.90-3.84 (m, 0.8H), 3.52-3.42 (m, 3H), 3.05-3.00 (m, 1H), 2.90-2.87 (m, 2H), 2.86-2.82 (m, 0.8H), 2.75-2.65 (m, 1.2H), 2.18-2.10 (m, 2H), 2.08-2.00 (m, 3H), 1.83-1.65 (m, 5H); MS (ESI+) m/z 370 (M+H); HPLC 98.4% (AUC), $t_R$=15.85 min.

Example 33

Preparation of Endo-N-(9-Methyl-9-azabicyclo[3.3.1]nonan-3-yl)-2-(1-methylpiperidin-2-yl)benzoxazole-4-carboxamide Hydrochloride Step A: A mixture of 1-methylpiperidine-2-carboxylic acid hydrochloride (0.57 g, 3.17 mmol), methyl 2-amino-3-hydroxybenzoate (0.64 g, 3.80 mmol), 1-ethyl-3-(3-dimethylaminopropyl)carbodiimide hydrochloride (1.26 g, 6.34 mmol), 1-hydroxybenzotriazole (0.85 g, 6.34 mmol) and DMF (20 mL) was stirred at room temperature for 5 min, then diisopropylethylamine (1.46 mL, 8.88 mmol) was added. The resulting reaction mixture was stirred at room temperature for 17 h. The mixture was diluted with ethyl acetate (10 mL), and then washed with saturated sodium bicarbonate (10 mL). The aqueous phase was further extracted with ethyl acetate (3×40 mL). The combined organic phase was washed with brine (10 mL), dried (Na$_2$SO$_4$), filtered and concentrated. The crude product (a mixture of 2-amino-3-(methoxycarbonyl)phenyl 1-methylpiperidine-2-carboxylate and methyl 3-hydroxy-2-(1-methylpiperidine-2-carboxamido)benzoate) was directly elaborated in step B: MS (ESI+) m/z 293 (M+H).

Step B: The crude product mixture from Step A (0.46 g, 1.59 mmol) was dissolved in toluene (20 mL) and the solution was treated with methanesulfonic acid monohydrate (2.08 g, 10.9 mmol). The reaction mixture was then heated to reflux using a Dean-Stark Trap containing 4 Å molecular sieves under nitrogen for 174 h. The reaction was cooled to room temperature and concentrated partitioned between saturated sodium bicarbonate (10 ml) and ethyl acetate (50 mL), the aqueous phase was further extracted with ethyl acetate (3×30 mL), washed with 5% lithium chloride solution, brine, dried (Na$_2$SO$_4$), filtered and concentrated. The crude product was purified by column chromatography (silica gel, 20 to 100% ethyl acetate in hexanes) to afford methyl 2-(1-methylpiperidin-2-yl)benzoxazole-4-carboxylate (233 mg, 54%) as an off-white solid: $^1$H NMR (500 MHz, CDCl$_3$) δ 8.00 (d, J=13.0 Hz, 1H), 7.74 (d, J=13.0 Hz, 1H), 4.02 (s, 3H), 3.60 (dd, J=17.2, 6.0 Hz, 1H), 3.12-3.06 (m, 1H), 2.30-2.26 (m, 4H), 2.08-1.80 (m, 3H), 1.78-1.60 (m, 2H), 1.48-1.30 (m, 2H); MS (ESI+) m/z 275 (M+H).

Step C: A mixture of methyl-2-(1-methylpiperidin-2-yl)-benzoxazole-4-carboxylate (0.33 g, 1.21 mmol), lithium hydroxide monohydrate (153 mg, 3.64 mmol) and methanol/water (3:1, 12 mL) was stirred at room temperature for 17 h. The reaction mixture was cooled to 0° C. and treated with HCl (1.0 M solution in diethyl ether, 4.30 mL, 4.30 mmol). The solvent was removed under vacuum and the crude 2-(1-methylpiperidin-2-yl)-benzoxazole-4-carboxylic acid directly elaborated without further purification: MS (ESI+) m/z 261 (M+H).

Step D: A mixture of the carboxylic acid product from Step C (310 mg, 1.21 mmol), endo-3-amino-9-methyl-9-azabicyclo[3.3.1]nonane dihydrochloride (330 mg, 1.45 mmol), 1-ethyl-3-(3-dimethylaminopropyl)carbodiimide hydrochloride (0.48 g, 2.42 mmol), 1-hydroxybenzotriazole (0.33 g, 2.42 mmol) and DMF (10 mL) was stirred at room temperature for 5 min, then triethylamine (0.50 mL, 3.63 mmol) was added. The resulting reaction mixture was stirred at room temperature for 17 h. The mixture was diluted with ethyl acetate (10 mL), and then washed with saturated sodium bicarbonate (10 mL). The aqueous phase was further extracted with ethyl acetate (3×40 mL). The combined organic phase was washed with brine (10 mL), dried (Na$_2$SO$_4$), filtered and concentrated. The crude material was purified by column chromatography (silica gel, 100% 9:1 dichloromethane/methanol to 100% 90:9:1 dichloromethane/methanol/concentrated ammonium hydroxide) to afford endo-N-(9-methyl-9-azabicyclo[3.3.1]nonan-3-yl)-2-(1-methylpiperidin-2-yl)benzoxazole-4-carboxamide (189 mg, 36%) as a off-white solid and as a mixture of enantiomers: $^1$H NMR (500 MHz, CDCl$_3$) δ 8.84 (s, 1H), 8.18 (d, J=7.5 Hz, 1H), 7.65 (d, J=8.0 Hz, 1H), 7.43 (app t, J=8.0 Hz, 1H), 4.62-4.52 (m, 1H), 3.59 (t, J=7.0 Hz, 1H), 3.15-3.06 (m, 3H), 2.64-2.50 (m, 6H), 2.35-2.28 (m, 1H), 2.24 (s, 3H), 2.16-1.88 (m, 7H), 1.83-1.74 (m, 2H), 1.56-1.40 (m, 2H), 1.17-1.07 (m, 2H); MS (ESI+) m/z 397 (M+H).

Step E: To solution of the carboxamide product from Step D (0.30 mg, 0.75 mmol) in dichloromethane (5 mL) was added HCl (1 M solution in ethyl ether, 2.26 mL, 2.26 mmol). The mixture was stirred at room temperature for 15 mins, and then the solvent was removed under vacuum. The amorphous solid was lyophilized from water (2 mL) containing a few drops of acetonitrile to afford endo-N-(9-methyl-9-azabicyclo[3.3.1]nonan-3-yl)-2-(1-methylpiperidin-2-yl)benzoxazole-4-carboxamide hydrochloride (209 mg, 94%) as an off-white solid and as a mixture of enantiomers: $^1$H NMR (500 MHz, DMSO-d$_6$) δ 12.50 (s, 0.8H), 12.35 (s, 0.2H), 10.62 (s, 0.2H), 9.72 (s, 0.8H), 8.98 (d, J=5.5 Hz, 0.2H), 8.82 (d, J=5.5 Hz, 0.6H), 8.04 (app q, J=8.5 Hz, 2H), 7.64 (app t, J=8.5 Hz, 1H), 5.00-4.88 (m, 1H), 4.82-4.72 (m, 0.8H), 4.43-4.36 (m, 0.2H), 3.63 (d, J=9.0 Hz, 1.5H), 3.58-3.50 (m, 1.5H), 3.46-3.38 (m, 0.2H), 3.28-3.19 (m, 0.8H), 2.87-2.80 (m, 3H), 2.77-2.68 (m, 3H), 2.68-2.57 (m, 1H), 2.55-2.42 (m, 2H), 2.35-2.03 (m, 7H), 1.94-1.84 (m, 3H), 1.72-1.60 (m, 1H), 1.58-1.43 (m, 3H); MS (ESI+) m/z 397 (M+H); HPLC>99% (AUC), t$_R$=12.84 min. Anal. Calcd for C$_{23}$H$_{32}$N$_4$O$_2$.2HCl.H$_2$O: C, 56.67; H, 7.44; N, 11.49. Found: C, 56.98; H, 7.67; N, 11.39.

Example 34

Preparation of Endo-N-(9-Methyl-9-azabicyclo[3.3.1]non-3-yl)-2-methylbenzoxazole-4-carboxamide Step A: To a mixture of 2-amino-3-hydroxybenzoic acid hydrobromide (0.35 g, 1.50 mmol) and acetyl chloride (0.11 mL, 1.50 mmol) in dichloromethane (10 mL) was added triethylamine (0.84 mL, 6.0 mmol) dropwise, then the reaction mixture was stirred at room temperature for 12 h. The reaction mixture was diluted with dichloromethane, and then washed with 2 N HCl. The aqueous layer was extracted with dichloromethane. The combined organic layers were washed with brine, dried (Na$_2$SO$_4$), filtered and concentrated. The crude product was dissolved in toluene (10 mL) and the solution was treated with p-toluenesulfonic acid monohydrate (263 mg, 1.38 mmol). The reaction mixture was then heated to reflux for 1.5 h. The reaction was cooled to room temperature, poured into water and extracted with ethyl acetate. The organic layer was separated then washed with water, brine, dried (Na$_2$SO$_4$), filtered and concentrated. The crude product was purified by column chromatography (silica gel, 9:1 to 3:1 ethyl acetate/methanol) to afford 2-methylbenzoxazole-4-carboxylic acid (0.17 g, 64%) as an off-white solid: MS (ESI+) m/z 178 (M+H).

Step B: A mixture of 2-methylbenzoxazole-4-carboxylic acid from Step A (75 mg, 0.42 mmol), endo-3-amino-9-methyl-9-azabicyclo[3.3.1]nonane dihydrochloride (95 mg, 0.42 mmol), 1-ethyl-3-(3-dimethylaminopropyl)carbodiimide hydrochloride (161 mg, 0.84 mmol) and 1-hydroxybenzotriazole (114 mg, 0.84 mmol) in DMF (4 mL) was stirred at room temperature for 5 min, then triethylamine (0.22 mL, 1.68 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried (Na$_2$SO$_4$), filtered and concentrated. The crude material was purified by column chromatography (silica gel, 89:10:1 dichloromethane/methanol/concentrated ammonium hydroxide) to afford endo-N-(9-methyl-9-azabicyclo[3.3.1]non-3-yl)-2-methylbenzoxazole-4-carboxamide (40 mg, 30%) as a white solid: $^1$H NMR (500 MHz, CDCl$_3$) δ 8.84 (d, J=6.0 Hz, 1H), 8.16 (dd, J=7.5, 1.0 Hz, 1H), 7.58 (dd, J=7.5, 1.0 Hz, 1H), 7.39 (t, J=8.0 Hz, 1H), 4.64-4.55 (m, 1H), 3.12 (d, J=10.5 Hz, 2H), 2.71 (s, 3H), 2.65-2.55 (m, 2H), 2.53 (s, 3H), 2.12-1.95 (m, 3H), 1.60-1.52

(m, 1H), 1.45 (t, J=10.5 Hz, 2H), 1.12 (d, J=12.5 Hz, 2H); MS (ESI+) m/z 314 (M+H); HPLC 98.0% (AUC), $t_R$=11.78 min.

Example 35

Preparation of (S)—N-(1-Azabicyclo[2.2.2]oct-3-yl)-2-methylbenzoxazole-4-carboxamide A mixture of 2-methylbenzoxazole-4-carboxylic acid (75 mg, 0.42 mmol), (S)-(−)-3-aminoquinuclidine dihydrochloride (84 mg, 0.42 mmol), 1-ethyl-3-(3-dimethylaminopropyl) carbodiimide hydrochloride (161 mg, 0.84 mmol) and 1-hydroxybenzotriazole (114 mg, 0.84 mmol) in DMF (4 mL) was stirred at room temperature for 5 min, then triethylamine (0.22 mL, 1.68 mmol) was added. The resulting reaction mixture was stirred at room temperature for 12 h. The mixture was diluted with dichloromethane (20 mL), then washed with a saturated solution of sodium bicarbonate (10 mL). The aqueous layer was further extracted with dichloromethane (3×15 mL). The combined organics were dried ($Na_2SO_4$), filtered and concentrated. The crude material was purified by column chromatography (silica gel, 89:10:1 dichloromethane/methanol/concentrated ammonium hydroxide) to afford (S)—N-(1-azabicyclo[2.2.2]oct-3-yl)-2-methylbenzoxazole-4-carboxamide (39 mg, 33%) as a white solid: $^1$H NMR (500 MHz, $CDCl_3$) δ 9.37 (d, J=7.0 Hz, 1H), 8.14 (dd, J=7.5, 1.0 Hz, 1H), 7.60 (dd, J=8.0, 2.0 Hz, 1H), 7.41 (t, J=8.0 Hz, 1H), 4.28-4.23 (m, 1H), 3.47 (ddd, J=11.5, 9.5, 2.0 Hz, 1H), 3.08-2.85 (m, 4H), 2.76 (dd, J=14.0, 4.5 Hz, 1H), 2.70 (s, 3H), 2.13-2.07 (m, 1H), 2.02-1.93 (m, 1H), 1.78-1.70 (m, 2H), 1.60-1.51 (m, 1H); MS (ESI+) m/z 286 (M+H); HPLC>99% (AUC), $t_R$=11.14 min.

Example 36

Preparation of N-(9-Azabicyclo[3.3.1]non-3-yl)-2-cyclopropylbenzoxazole-4-carboxamide Hydrochloride Step A: To a solution of endo-N-(9-methyl-9-azabicyclo [3.3.1]non-3-yl)-2-cyclopropylbenzoxazole-4-carboxamide (260 mg, 0.766 mmol) in THF (2 mL) was added a solution of sodium hydroxide (0.60 g, 15 mmol) in water (10 mL) at 0° C., followed by a solution of $KMnO_4$ (0.60 g, 3.8 mmol) in water (30 mL). The mixture was stirred at 0° C. for 1 h, and then was quenched with a saturated solution of sodium bicarbonate and extracted with methylene chloride. The combined organic layers were washed with brine, dried ($Na_2SO_4$), filtered and concentrated. The crude material was purified by column chromatography (silica gel, 90:9:1 dichloromethane/methanol/concentrated ammonium hydroxide) to afford the desired secondary amine (37 mg, 15%) as a white solid: $^1$H NMR (500 MHz, $CDCl_3$) δ 8.90 (d, J=7.5 Hz, 1H), 8.11 (dd, J=7.5, 1.0 Hz, 1H), 7.53 (dd, J=7.5, 1.0 Hz, 1H), 7.34 (t, J=7.5 Hz, 1H), 4.32-4.23 (m, 1H), 3.45-3.40 (m, 2H), 2.44-2.28 (m, 3H), 2.05-1.70 (m, 4H), 1.60-1.25 (m, 9H); MS (ESI+) m/z 326 (M+H).

Step B: Hydrogen chloride in diethyl ether (1.0 M, 0.11 mL, 0.11 mmol) was added dropwise to a solution of the amine from Step A (35 mg, 0.11 mmol) in methylene chloride (1 mL) at 0° C. The mixture was stirred for 2 min, and then was diluted with diethyl ether (30 mL). The white solid was filtered, washed with diethyl ether, and dried under vacuum overnight to afford N-(9-azabicyclo[3.3.1]non-3-yl)-2-cyclopropylbenzoxazole-4-carboxamide hydrochloride (30 mg, 77%) as a white solid: $^1$H NMR (500 MHz, DMSO-$d_6$) δ 8.83-8.49 (m, 3H), 7.88-7.84 (m, 2H), 7.44 (t, J=7.5 Hz, 1H), 4.44-4.35 (m, 1H), 3.85-3.80 (m, 2H), 2.50-2.40 (m, 3H), 2.12-1.85 (m, 3H), 1.65-1.23 (m, 9H); MS (ESI+) m/z 326 (M+H); HPLC>99% (AUC), $t_R$=11.80 min.

Example 37

Preparation of Endo-N-(9-methyl-9-azabicyclo [3.3.1]non-3-yl)-2-tert-butyl benzoxazole-7-carboxamide Hydrochloride Step A: A mixture of pivaldehyde (1.65 mL, 15.4 mmol), methyl 3-amino-2-hydroxybenzoate (501 mg, 3.0 mmol) and Darco KB-B (375 mg) in xylenes (8 mL) was heated under an oxygen atmosphere at 120° C. for 12 h. The reaction mixture was cooled to room temperature, filtered through a celite pad. The filtrate was concentrated and the crude material was purified by column chromatography (silica gel, 7:3 hexanes/ethyl acetate) to afford the desired methyl 2-tert-butylbenzoxazole-7-carboxylate (417 mg, 60%) as a light orange oil: $^1$H NMR (500 MHz, $CDCl_3$) δ 7.94 (dd, J=7.8, 0.9 Hz, 1H), 7.88 (dd, J=7.8, 0.9 Hz, 1H), 7.36 (t, J=7.8 Hz, 1H), 4.01 (s, 3H), 1.54 (s, 9H); MS (ESI+) m/z 234 (M+H).

Step B: A mixture of methyl 2-tert-butylbenzoxazole-7-carboxylate (0.41 g, 1.77 mmol), lithium hydroxide monohydrate (222 mg, 5.30 mmol) and tetrahydrofuran/water (5:1, 6 mL) was stirred at room temperature for 17 h. The reaction mixture was cooled to 0° C., adjusted to pH 2 using 1 N HCl, and then extracted with dichloromethane (2×200 mL). The combined organic phase was washed with brine (2×50 mL), dried ($Na_2SO_4$), filtered and concentrated to afford the desired 2-tert-butylbenzoxazole-7-carboxylic acid (336 mg, 86%) as a pink solid: $^1$H NMR (300 MHz, DMSO-$d_6$) δ 13.20 (br s, 1H), 7.95 (d, J=7.8 Hz, 1H), 7.84 (d, J=7.8 Hz, 1H), 7.45 (t, J=7.8 Hz, 1H), 1.45 (s, 9H); MS (ESI+) m/z 220 (M+H).

Step C: A mixture of 2-tert-butylbenzoxazole-7-carboxylic (200 mg, 0.91 mmol), 3-amino-9-methyl-9-azabicyclo[3.3.1] nonane dihydrochloride (259 mg, 1.14 mmol), 1-ethyl-3-(3-dimethylaminopropyl)carbodiimide hydrochloride (348 mg, 1.82 mmol) and 1-hydroxybenzotriazole (246 mg, 1.82 mmol) in DMF (5 mL) was stirred under nitrogen at room temperature for 10 min, and then triethylamine (0.51 mL, 3.64 mmol) was added. The resulting reaction mixture was stirred at room temperature for 17 h. The reaction was quenched with saturated aqueous sodium bicarbonate (10 mL), and then extracted with ethyl acetate (2×100 mL). The combined organic phase was washed with water (1×50 mL), brine (1×50 mL) dried ($Na_2SO_4$), filtered and concentrated. The crude material was purified by column chromatography (silica gel, 90:6:1 dichloromethane/methanol/concentrated ammonium hydroxide) to afford endo-N-(9-methyl-9-azabicyclo[3.3.1]non-3-yl)-2-tert-butyl benzoxazole-7-carboxamide (266 mg, 82%) as a white solid: $^1$H NMR (500 MHz, $CDCl_3$) δ 8.05 (d, J=7.8 Hz, 1H), 7.81 (d, J=7.8 Hz, 1H), 7.41 (t, J=7.8 Hz, 1H), 6.92 (d, J=6.2 Hz, 1H), 4.65-4.54 (m, 1H), 3.15 (d, J=9.1 Hz, 2H), 2.67-2.60 (m, 2H), 2.55 (s, 3H), 2.10-1.95 (m, 3H), 1.65-1.58 (m, 1H), 1.55 (s, 9H), 1.45-1.35 (m, 2H), 1.18-1.10 (m, 2H); MS (ESI+) m/z 356 (M+H).

Step D: To an ice cold solution of endo-N-(9-methyl-9-azabicyclo[3.3.1]non-3-yl)-2-tert-butyl benzoxazole-7-carboxamide (141 mg, 0.39 mmol) in methanol (2 mL) and dichloromethane (2 mL) was slowly added a solution of HCl (1 N in diethyl ether, 0.39 mL, 0.39 mmol). The reaction mixture was diluted with diethyl ether (250 mL). The resulting solid was filtered and washed with diethyl ether (200 mL) to afford a white solid. The solid was lyophilized from water (4 mL) and acetonitrile (2 mL) to afford endo-N-(9-methyl-9-azabicyclo[3.3.1]non-3-yl)-2-tert-butyl benzoxazole-7- carboxamide hydrochloride (160 mg, 100%) as a white solid: $^1$H NMR (500 MHz, DMSO-$d_6$) δ 10.18 (br s, 0.25H), 9.44 (br s, 0.75H), 8.47 (d, J=7.4 Hz, 0.25H), 8.37 (d, J=7.4, Hz, 0.75H), 7.87-7.84 (m, 1H), 7.63-7.68 (m, 1H), 7.46-7.42 (m, 1H), 4.65-4.55 (m, 0.75H), 4.38-4.30 (m, 0.25H), 3.65-3.56 (m, 2H), 3.55-3.38 (m, 2H), 2.84-2.80 (m, 3H), 2.64-2.60 (m, 1H), 2.20-2.02 (m, 3H), 1.85-1.75 (m, 3H), 1.60-1.52 (m, 1H), 1.46 (s, 9H); MS (ESI+) m/z 356 (M+H); HPLC 93.4% (AUC), $t_R$=9.70 min. Anal. Calcd for $C_{21}H_{29}N_3O_2$.HCl: C, 58.31; H, 7.86; N, 9.71; Cl, 10.24. Found: C, 58.29; H, 7.79; N, 9.71; Cl, 10.29.

Example 38

Preparation of (S)—N-(Azabicyclo[2.2.2]oct-3-yl)-2-(morpholinomethyl)benzoxazole-4-carboxamide Hydrochloride Step A: To an ice-cooled suspension of 2-amino-3-hydroxybenzoic acid hydrobromide (3.0 g, 12.8 mmol) in toluene (30 mL) and methanol (30 mL) was added (trimethylsilyl)diazomethane (16.0 mL, 2 M solution in ethyl ether, 32.0 mmol) slowly, then the mixture was stirred at 0° C. for 20 min. Acetic acid (5 mL) was added into the reaction mixture at 0° C., then the mixture was stirred at room temperature for 0.5 h. The reaction mixture was concentrated under reduced pressure, and then the crude was dissolved in ethyl acetate and washed with a saturated solution of sodium bicarbonate and brine. The organic layer was dried ($Na_2SO_4$), filtered and concentrated under reduced pressure. The crude product was purified by column chromatography (silica gel, 1:1 hexanes/ethyl acetate) to afford the desired product (2.04 g, 95%) as a light brown solid: $^1$H NMR (500 MHz, $CDCl_3$) δ 7.48 (dd, J=8.0, 1.5 Hz, 1H), 6.81 (dd, J=7.5, 1.5 Hz, 1H), 6.50 (t, J=8.0 Hz, 1H), 5.80 (br s, 2H), 3.87 (s, 3H); MS (ESI+) m/z 168 (M+H).

Step B: A mixture of methyl 2-amino-3-hydroxybenzoate (3.5 g, 20.70 mmol) and 2-chloro-1,1,1-trimethoxyethane (3.0 mL, 22.06 mmol) in ethanol (30 mL) was stirred under reflux for 6 h. The reaction mixture was cooled to ambient temperature and the solvent volume was reduced under reduced pressure approximately to ⅔ of initial volume. The precipitate formed was filtered, washed with ether (3×10 mL), and dried under vacuum to afford methyl 2-(chloromethyl)benzoxazole-4-carboxylate (3.1 g, 66%) as a yellow solid: $^1$H NMR (500 MHz, $CDCl_3$) δ 8.05 (dd, J=8.0, 1.0 Hz, 1H), 7.78 (dd, J=9.0, 1.0 Hz 1H), 7.47 (t, J=5.0 Hz, 1H), 4.84 (s, 2H), 4.04 (s, 3H); (APCI+) m/z 226 (M+H).

Step C: A mixture of the product from Step B (281 mg, 1.24 mmol) and morpholine (2.0 mL, 23 mmol) in DMF (10 mL) was stirred at ambient temperature for 16 h. The solvent was removed under reduced pressure and the residue was treated with ethyl acetate (10 mL). The formed precipitate was filtered off and mother liquor was concentrated under reduced pressure to afford methyl 2-(morpholinomethyl)benzoxazole-4-carboxylate (333 mg, 97%) as a yellow solid: $^1$H NMR (300 MHz, $CDCl_3$) δ 8.01 (dd, J=9.0, 1.0 Hz, 1H), 7.74 (dd, J=9.0, 1.0 Hz, 1H), 6.40 (t, J=7.8 Hz, 1H), 4.02 (s, 2H), 3.97 (s, 3H), 3.78-3.74 (m, 4H), 2.69-2.65 (m, 4H); MS (ESI+) m/z 277 (M+H).

Step D: A mixture of the product from Step C (333 mg, 1.20 mmol) and lithium iodide (642 mg, 4.80 mmol) in pyridine (15 mL) was stirred at 120° C. for 16 h. The solvent was removed under reduced pressure to afford a black powder (0.9 g). Analysis by LC-MS indicated only one main product with (APCI+) m/z 273 (M+H), consistent with desired acid. The obtained powder was dissolved in anhydrous DMF (15 mL) and the obtained solution was elaborated into next step without further purification. (S)-(−)-3-Aminoquinuclidine dihydrochloride (140 mg, 0.72 mmol) and HBTU (224 mg, 0.58 mmol) were added to the obtained solution (7.5 mL) and the mixture was stirred under nitrogen at room temperature for 10 min. Triethylamine (0.15 mL, 1.2 mmol) was added and the resulting reaction mixture was stirred at room overnight. The reaction was quenched with saturated aqueous sodium bicarbonate (50 mL), and then extracted with dichloromethane (2×100 mL). The combined organic phase was washed with brine (2×100 mL), water (2×100 mL), dried ($Na_2SO_4$), filtered, and concentrated under reduced pressure. The crude material was purified by column chromatography (silica gel, 10:1:0.1 dichloromethane/methanol/concentrated ammonium hydroxide) to afford (S)—N-(quinulidin-8-yl)-2-(morpholinomethyl)benzoxazole-4-carboxamide (62 mg, 29%) as a yellow solid: $^1$H NMR (300 MHz, $CDC_3$) δ 9.34 (d, J=6.0 Hz, 1H), 8.17 (dd, J=7.8, 1.0 Hz, 1H), 7.68 (dd, J=9.0, 1.0 Hz, 1H), 7.47 (t, J=8.1 Hz, 1H), 4.48-4.35 (m, 1H), 3.90 (s, 2H), 3.79-3.72 (m, 4H), 3.57-3.45 (m, 1H), 3.10-3.00 (m, 1H), 2.98-2.92 (m, 2H), 2.85-2.74 (m, 1H), 2.71-2.68 (m, 4H), 2.20-2.08 (m, 1H), 2.07-1.92 (m, 2H), 1.84-1.72 (m, 2H), 1.68-1.52 (m, 1H); MS (APCI+) m/z 371 (M+H).

Step E: To a solution of the product from Step D (30 mg, 0.07 mmol) in methanol (2 mL) was slowly added a solution of HCl (1.25 N in methanol, 0.12 mL, 0.14 mmol). The reaction mixture was stirred for 5 minutes at ambient temperature and then concentrated under reduced pressure. The resulting residue was lyophilized from water (5 mL) to afford (S)—N-(quinulidin-8-yl)-2-(morpholinomethyl)benzoxazole-4-carboxamide hydrochloride (26 mg, 82%) as a white solid: $^1$H NMR (500 MHz, DMSO-$d_6$) δ 10.14 (s, 1H), 9.05 (s, 1H), 8.03 (d, J=8.1, 1H), 7.95 (d, J=7.8 Hz, 1H), 7.61 (t, J=8.0 Hz, 1H), 4.35 (s, 1H), 3.92-3.82 (m, 4H), 3.74-3.70 (m, 2H), 3.60-3.40 (m, 6H), 3.25-3.23 (m, 4H), 2.28-2.26 (m, 1H), 2.20-2.12 (m, 1H), 1.97-1.94 (m, 2H), 1.90-1.80 (m, 1H); MS (ESI) m/z 371 (M+H); HPLC 98.0% (AUC), $t_R$=9.91 min.

Example 39

Preparation of Endo-N-(9-Methyl-9-azabicyclo[3.3.1]nonan-3-yl)-2-(morpholinomethyl)benzoxazole-4-carboxamide Hydrochloride Step A: Endo-N-3-amino-(9-methyl-9-azabicyclo[3.3.1]nonane dihydrochloride (160 mg, 0.72 mmol) and HBTU (224 mg, 0.58 mmol) were added to the solution (7.5 mL) of crude 2-(morpholinomethyl)benzoxazole-4-carboxylic acid. The mixture was stirred under nitrogen at ambient temperature for 10 min, and then triethylamine (0.15 mL, 1.2 mmol) was added. The resulting reaction mixture was stirred at ambient temperature for 16 h. The reaction was quenched with saturated aqueous sodium bicarbonate (50 mL), and then extracted with dichloromethane (2×100 mL). The combined organic phase was washed with brine (2×100 mL), water (2×100 mL), dried ($Na_2SO_4$), filtered, and concentrated under reduced pressure. The crude material was purified by column chromatography (silica gel, 10:1:0.1 dichloromethane/methanol/concentrated ammonium hydroxide) to afford (endo-N-(9-methyl-9-azabicyclo[3.3.1]nonan-3-yl)-2-(morpholinomethyl)benzoxazole-4-carboxamide (90 mg, 39%) as a yellow powder; MS (APCI) m/z 399 (M+H).

Step B: To a solution of the product from Step A (88 mg, 0.22 mmol) in methanol (2 mL) was slowly added a solution of HCl (1.25 N in methanol, 0.35 mL, 0.44 mmol). The reaction mixture was stirred for 10 min at ambient temperature and concentrated under reduced pressure. The resulting residue was lyophilized from water (5 mL) to afford endo-N-(9-methyl-9-azabicyclo[3.3.1]nonan-3-yl)-2-(morpholinomethyl)benzoxazole-4-carboxamide hydrochloride (65 mg, 68%) as a white solid: $^1$H NMR (500 MHz, DMSO-d$_6$) δ 10.45 (s, 0.3H), 9.63 (s, 0.7H), 9.06 (br s, 0.3H), 8.84 (d, J=6.0 Hz, 0.7H), 8.02-7.99 (m, 1H), 7.97-7.94 (m, 1H), 7.58 (t, J=7.5 Hz, 1H), 4.72-4.5.6 (m, 2H), 4.40-4.38 (m, 1H), 4.06-3.70 (m, 4H), 3.65 (d, J=9.5 Hz, 2H), 3.57 (d, J=6.5 Hz, 1H), 3.52-3.30 (m, 4H), 2.87-2.82 (m, 3H), 2.71-2.61 (m, 1H), 2.54 (s, 1H), 2.32-2.20 (m, 1.5H), 2.17-2.08 (m, 1.5H), 1.98 (s, 1H), 187-1.70 (m, 1H), 1.54-1.46 (m, 2H); MS (ESI) m/z 399 (M+H); HPLC 98.14% (AUC), $t_R$=9.90 min.

Example 40

Preparation of (S)—N-(Azabicylco[2.2.2]oct-3-yl)-2-(diethylaminomethyl)benzoxazole-4-carboxamide Hydrochloride Step A: A mixture of methyl 2-(chloromethyl)benzoxazole-4-carboxylate (267 mg, 1.18 mmol) and diethylamine (2.0 mL, 27.4 mmol) in THF (15 mL) was stirred at ambient temperature overnight. The solvent was removed under reduced pressure and the residue was purified by column chromatography (silica gel, 10:1:0.1 dichloromethane/methanol/concentrated ammonium hydroxide), followed by purification by preparative TLC (silica gel, 10:1:0.1 dichloromethane/methanol/concentrated ammonium hydroxide) to afford methyl 2-(diethylaminomethyl)benzoxazole-4-carboxylate (200 mg, 64%) as a yellow oil: $^1$H NMR (300 MHz, CDCl$_3$) δ 7.99 (dd, J=9.0, 1.0 Hz, 1H), 7.74 (dd, J=9.0, 1.0 (1H), 6.40 (t, J=8.1 Hz, 1H), 4.09 (s, 2H), 4.04 (s, 3H), 2.74-2.69 (m, 4H), 1.13 (t, J=6.6 Hz, 1H); MS (ESI+) m/z 263 (M+H).

Step B: A mixture of the product from Step A (200 mg, 0.7 mmol) and lithium iodide (398 mg, 2.97 mmol) in pyridine (15 mL) was stirred at 125° C. overnight. The solvent was removed under reduced pressure to afford a brown oil (0.7 g). Analysis by LC-MS indicated only one main product with (APCI+) m/z 249 (M+H), consistent with desired acid. The obtained oil was dissolved in anhydrous DMF (15 mL) and the obtained solution was elaborated into the next step without further purification. (S)-(−)-3-Aminoquinuclidine dihydrochloride (120 mg, 0.60 mmol) and HBTU (305 mg, 0.80 mmol) were added to the obtained solution (10 mL) and the mixture was stirred under nitrogen at room temperature for 10 min, and then triethylamine (0.30 mL, 2.16 mmol) was added. The resulting reaction mixture was stirred at ambient temperature overnight. The reaction was quenched with saturated aqueous sodium bicarbonate (50 mL), and then extracted with dichloromethane (2×100 mL). The combined organic phase was washed with brine (2×100 mL) water (2×100 mL), dried (Na$_2$SO$_4$), filtered and concentrated under reduced pressure. The crude material was purified by column chromatography (silica gel, 10:1:0.1 dichloromethane/methanol/concentrated ammonium hydroxide), followed by purification by preparative TLC (silica gel, 10:1:0.1 dichloromethane/methanol/concentrated ammonium hydroxide) to afford (S)—N(quinulidin-8-yl)-2-(diethylaminomethyl)benzoxazole-4-carboxamide (63 mg, 29%) as a yellow solid: MS (APCI+) m/z 357 (M+H).

Step C: To a solution of the product from Step B (52 mg, 0.14 mmol) in methanol (2 mL) was slowly added a solution of HCl (1.25 N in methanol, 0.32 mL, 0.40 mmol). The reaction mixture was stirred for 10 minutes at ambient temperature and concentrated under reduced pressure. The resulting residue was lyophilized from water (5 mL) to afford (S)—N-(quinulidin-8-yl)-2-(diethylaminomethyl)benzoxazole-4-carboxamide hydrochloride (57 mg, 65%) as a white solid: $^1$H NMR (500 MHz, DMSO-d$_6$) δ 10.71 (s, 1H), 10.14 (s, 1H), 8.96 (d, J=5.1 Hz, 1H), 8.06 (d, J=8.0 Hz, 1H), 7.65-7.61 (m, 1H), 4.90 (s, 2H), 4.64 (s, 1H), 3.72 (d, J=10.8 Hz, 1H), 3.54-3.48 (m, 4H), 3.44-3.27 (m, 8H), 3.24 (d, J=7.2 Hz, 3H), 2.31-2.26 (m, 1H), 2.17-2.09 (m, 1H), 1.97-1.94 (m, 2H), 1.89-1.71 (m, 1H), 1.35 (s, 3H); MS (ESI) m/z 357 (M+H); HPLC 98.50% (AUC), $t_R$=9.73 min.

Example 41

Preparation of Endo-N-(9-Methyl-9-azabicyclo[3.3.1]nonan-3-yl)-2-(diethylaminomethyl)benzoxazole-4-carboxamide Hydrochloride Step A: A mixture of methyl 2-amino-3-hydroxybenzoate (3.5 g, 20.70 mmol) and 2-chloro-1,1,1-trimethoxyethane (3.0 mL, 22.06 mmol) in ethanol (30 mL) was stirred under reflux for 6 h. The reaction mixture was cooled to ambient temperature and the solvent volume was reduced under reduced pressure approximately to ⅔ of initial volume. The precipitate formed was filtered, washed with ether (3×10 mL) and dried to afford methyl 2-(chloromethyl)benzoxazole-4-carboxylate (3.1 g, 66%) as a yellow solid: $^1$H NMR (500 MHz, CDCl$_3$) δ 8.05 (dd, J=8.0, 1.0 Hz, 1H), 7.78 (dd, J=9.0, 1.0 Hz 1H), 7.47 (t, J=5.0 Hz, 1H), 4.84 (s, 2H), 4.04 (s, 3H); (APCI+) m/z 226 (M+H).

Step B: A mixture of methyl 2-(chloromethyl)benzoxazole-4-carboxylate (267 mg, 1.18 mmol) and diethylamine (2.0 mL, 27.4 mmol) in THF (15 mL) was stirred at ambient temperature overnight The solvent was removed under reduced pressure and the residue was purified by column chromatography (silica gel, 10:1:0.1 dichloromethane/methanol/concentrated ammonium hydroxide), followed by purification by preparative TLC (silica gel, 10:1:0.1 dichloromethane/methanol/concentrated ammonium hydroxide) to afford methyl 2-(diethylaminomethyl)benzoxazole-4-carboxylate (200 mg, 64%) as a yellow oil: $^1$H NMR (300 MHz, CDCl$_3$) δ 7.99 (dd, J=9.0, 1.0 Hz, 1H), 7.74 (dd, J=9.0, 1.0 (1H), 6.40 (t, J=8.1 Hz, 1H), 4.09 (s, 2H), 4.04 (s, 3H), 2.74-2.69 (m, 4H), 1.13 (t, J=6.6 Hz, 1H); MS (ESI+) m/z 263 (M+H).

Step C: A mixture of methyl 2-((diethylamino)methyl)benzoxazole-4-carboxylic acid (200 mg, 0.7 mmol) and lithium iodide (398 mg, 2.97 mmol) in pyridine (15 mL) was stirred at 125° C. overnight. The solvent was removed under reduced pressure to afford a brown oil (0.7 g). Analysis by LC-MS indicated only one main product with (APCI+) m/z 249 (M+H), consistent with the desired acid. The obtained oil was dissolved in anhydrous DMF (15 mL) and the obtained solution was elaborated into the next step without further purification. 1-Ethyl-3-(3-dimethylaminopropyl)carbodiimide hydrochloride (90 mg, 0.5 mmol), 1-hydroxybenzotriazole (70 mg, 0.5 mmol), and endo-N-3-amino-(9-methyl-9-azabicyclo[3.3.1]nonane dihydrochloride (57 mg, 0.25 mmol) were added to the obtained solution (5 mL) and the mixture was stirred under nitrogen at room temperature for 10 min, and then triethylamine (0.15 mL, 1.08 mmol) was added. The resulting reaction mixture was stirred at ambient temperature for 16 h. The reaction was quenched with saturated aqueous sodium bicarbonate solution (50 mL), and then extracted with dichloromethane (2×100 mL). The combined organic phase was washed with brine (2×100 mL) water (2×100 mL), dried (Na$_2$SO$_4$), filtered, and concentrated under reduced pressure. The crude material was purified by column chromatography (silica gel, 10:1:0.1 dichloromethane/methanol/concentrated ammonium hydroxide), followed by purification by preparative TLC (silica gel, 10:1:0.1 dichloromethane/methanol/concentrated ammonium hydroxide) to afford endo-N-(9-methyl-9-azabicyclo[3.3.1]nonan-3-yl)-2-(diethylaminomethyl)benzoxazole-4-carboxamide (43 mg, 55%) as a clear oil: MS (APCI+) m/z 385 (M+H).

Step D: To a solution of the product from Step C (43 mg, 0.11 mmol) in methanol (2 mL) was slowly added a solution of hydrochloric acid (1.25 N in methanol, 0.16 mL, 0.20 mmol). The reaction mixture was stirred for 10 min at ambient temperature and then concentrated under reduced pressure. The resulting residue was lyophilized from water (5 mL) to afford endo-N-(9-methyl-9-azabicyclo[3.3.1]nonan-3-yl)-2-(diethylaminomethyl)benzoxazole-4-carboxamide hydrochloride (37 mg, 73%) as a white solid: $^1$H NMR (500 MHz, DMSO-$d_6$) δ 10.47 (s, 0.2H), 9.55 (s, 0.8H), 8.84 (s, 0.2H); 8.76 (d, J=7.5 Hz, 0.8H), 8.06-8.03 (m, 1H), 8.00-7.96 (m, 1H), 7.66-7.59 (m, 1H), 4.88-4.85 (m, 2H), 4.79-4.70 (m, 0.8H), 4.43-4.38 (m, 0.2H), 3.67-3.64 (m, 1.5H), 3.60-3.58 (m, 0.5H), 3.37-3.34 (m, 8H), 2.69-2.62 (m, 0.5H), 2.39-2.28 (m, 1H), 2.23-2.21 (m, 0.5H), 2.12-1.99 (m, 3H), 1.91-1.88 (m, 0.5H), 1.81-1.78 (0.5H), 1.52-1.49 (m, 1H), 1.46-1.42 (m, 2H), 1.38-1.35 (m, 6H); MS (ESI) m/z 385 (M+H); HPLC 98.07% (AUC), $t_R$=10.42 min.

Example 42

Preparation of Endo-N-(9-methyl-9-azabicyclo[3.3.1]nonan-3-yl)-2-((4S,5R/4R,5S)-3,5-dimethyl-2-oxo-oxazolidin-4-yl)benzoxazole-4-carboxamide Step A: To a solution of (2S,3R/2R,3S)-methyl 3-hydroxy-2-(methylamino)butanoate[1] (600 mg, 4.08 mmol) and triethylamine (1.71 mL, 12.27 mmol) in dichloromethane (30 mL) was added a solution of triphosgene (424 mg, 1.43 mmol) in dichloromethane (10 mL). The reaction was stirred at ambient temperature for 8 h then partitioned with 1 N HCl (20 mL). The organic layer was dried over $Na_2SO_4$ and concentrated under reduced pressure. The crude material was dissolved in methanol (10 mL) and treated with a solution of NaOH (326 mg, 8.15 mmol) in water (2 mL). The reaction mixture was stirred at ambient temperature for 14 h, then 2 N HCl added until the mixture attained pH 5. The reaction mixture was concentrated under reduced pressure and the residue was lyophilized. The resulting solid was heated with acetonitrile (50 mL) at 60° C. and insoluble inorganic salts removed by filtration. The filtrate was concentrated under reduced pressure to afford (4S,5R/4R,5S)-3,5-dimethyl-2-oxo-oxazolidine-4-carboxylic acid as a colorless oil (410 mg, 63%): $^1$H NMR (300 MHz, $CD_3OD$) δ 4.48-4.57 (m, 1H), 3.84 (d, J=5.7 Hz, 1H), 2.90 (s, 3H), 1.47 (d, J=6.3 Hz, 3H).

[1] (2S,3R/2R,3S)-methyl 3-hydroxy-2-(methylamino)butanoate was prepared according to a literature procedure: Beulshausen et al. *Liebigs Ann. Chem.* 1992, 523-526.

Step B: To a solution of (4S,5R/4R,5S)-3,5-dimethyl-2-oxo-oxazolidine-4-carboxylic acid (200 mg, 1.26 mmol) in DMF (0.5 mL) and THF (4.5 mL) at 0° C. was added oxalyl chloride (123 μL, 1.38 mmol). The reaction was stirred at ambient temperature for 2 h then concentrated under reduced pressure. The residue was dissolved in THF (5 mL) and methyl 2-amino-3-hydroxybenzoate (420 mg, 2.51 mmol) added followed by pyridine (255 μL, 3.15 mmol). The reaction mixture was stirred at ambient temperature for 60 h then partitioned with ethyl acetate (50 mL) and 0.5 M citric acid (20 mL). The organic layer was washed with brine, dried over $Na_2SO_4$ and concentrated under reduced pressure. The residue was purified by flash column chromatography (20 to 60% ethyl acetate/hexanes) to afford methyl 2-((4S,5R/4R,5S)-3,5-dimethyl-2-oxo-oxazolidine-4-carboxamido)-3-hydroxybenzoate as a yellow oil (195 mg, 50%): $^1$H NMR (300 MHz, $CDCl_3$) δ 7.60-7.65 (m, 1H), 7.20-7.27 (m, 2H), 4.60-4.72 (m, 1H), 4.00-4.08 (m, 1H), 3.94 (s, 3H), 3.03 (s, 3H), 1.60 (d, J=6.4 Hz, 3H).

Step C: To a solution of methyl 2-((4S,5R/4R,5S)-3,5-dimethyl-2-oxo-oxazolidine-4-carboxamido)-3-hydroxybenzoate (226 mg, 0.73 mmol), triphenylphosphine (495 mg, 1.89 mmol) and diisopropylethylamine (0.77 mL, 4.40 mmol) in dichloromethane (10 mL) was added hexachloroethane (434 mg, 1.83 mmol). The reaction mixture was stirred at ambient temperature for 20 h then quenched with a saturated solution of ammonium chloride (4 mL). The mixture was partitioned with dichloromethane (30 mL) and water (20 mL). The organic layer was washed with brine, dried ($Na_2SO_4$) and concentrated under reduced pressure. The crude material was purified by column chromatography (silica gel, EtOAc) to afford methyl 2-((4S,5R/4R,5S)-3,5-dimethyl-2-oxo-oxazolidin-4-yl)benzoxazole-4-carboxylate as a yellow oil (180 mg, 85%): $^1$H NMR (300 MHz, $CDCl_3$) δ 8.06 (dd, J=7.8, 1.0 Hz, 1H), 7.79 (dd, J=8.2, 1.0 Hz, 1H), 7.50 (t, J=8.0 Hz, 1H), 4.80-4.88 (m, 1H), 4.76 (d, J=5.6 Hz, 1H), 4.03 (s, 3H), 2.91 (s, 3H), 1.61 (d, J=6.2 Hz, 3H); MS (ESI+) m/z 291 (M+H).

Step D: To a solution of methyl 2-((4S,5R/4R,5S)-3,5-dimethyl-2-oxo-oxazolidin-4-yl)benzoxazole-4-carboxylate (180 mg, 0.62 mmol) in pyridine (7 mL) was added lithium iodide (831 mg, 6.20 mmol). The reaction mixture was heated at 110° C. for 5 h and allowed to cool to ambient temperature before it was partially concentrated under reduced pressure. The residue was partitioned with dichloromethane (30 mL) and 1 N HCl (20 mL). The organic layer was washed with brine, dried over $Na_2SO_4$ and concentrated under reduced pressure to afford crude 2-((4S,5R/4R,5S)-3,5-dimethyl-2-oxo-oxazolidin-4-yl)benzoxazole-4-carboxylic acid as an orange oil. This material was directly elaborated without purification.

Step E: To 2-((4S,5R/4R,5S)-3,5-dimethyl-2-oxo-oxazolidin-4-yl)benzoxazole-4-carboxylic acid (171 mg, 0.62 mmol), in N,N-dimethylformamide (4 mL), was added successively endo-9-methyl-3-oxa-9-azabicyclo[3.3.1]nonan-7-amine dihydrochloride (155 mg, 0.68 mmol), 1-hydroxybenzotriazole (168 mg, 1.24 mmol), 1-ethyl-3-(3-dimethylamino-propyl)carbodiimide hydrochloride (238 mg, 1.24 mmol) and triethylamine (261 μL, 1.86 mmol). The reaction was stirred at ambient temperature for 16 h then partitioned with a 9:1 mixture of dichloromethane and 2-propanol (100 mL) and water (100 mL). The phases were separated and the organic layer washed with brine before drying over $Na_2SO_4$. The organic layer was concentrated under reduced pressure and the residue purified by flash column chromatography (silica gel, 90:9:1 dichloromethane/methanol/concentrated ammonium hydroxide) to afford endo-N-(9-methyl-9-azabicyclo[3.3.1]nonan-3-yl)-2-((4S,5R/4R,5S)-3,5-dimethyl-2-oxo-oxazolidin-4-yl)benzoxazole-4-carboxamide (108 mg, 42%) as an off-white solid: $^1$H NMR (500 MHz, $CDCl_3$) δ 8.54 (d, J=12.6 Hz, 1H), 8.26 (dd, J=7.7, 0.9 Hz, 1H), 7.70 (dd, J=8.2, 0.9 Hz, 1H), 7.53 (t, J=8.0 Hz, 1H), 4.82-4.87 (m, 1H), 4.67 (d, J=5.7 Hz, 1H), 4.52-4.61 (m, 1H), 3.10 (d, J=10.4 Hz, 2H), 3.00 (s, 3H), 2.53-2.62 (m, 2H), 2.52 (s, 3H), 1.95-2.10 (m, 3H), 1.66 (d, J=6.3 Hz, 3H), 1.53-1.59 (m, 1H), 1.37-1.44 (m, 2H), 1.08-1.14 (m, 2H); MS (ESI+) m/z 413 (M+H); HPLC>99% (AUC), $t_R$ 12.7 min.

In other embodiments where $R^2$ is not hydrogen or halogen, the method of preparation of the foregoing is similar to those presented in U.S. Patent Application 2006/183769, the entire contents of which are herein incorporated by reference. In situations where an inconsistency in nomenclature between the foregoing application and the present application may exist, the nomenclature and definitions of the present application take precedence.

Compound Affinity for the Human 5-HT$_3$ Receptor (Assay A)

Compounds were tested by MDS Pharma Services—Taiwan Ltd., 158 Li—The Road, Peitou, Taipei, Taiwan 112 R.O.C. In order to evaluate the relative affinity of the various compounds for the human 5-HT$_3$ receptor, N1E-155 cell lines were developed to express the target protein. For binding, these cells were homogenized, centrifuged and washed with buffer (20 mM HEPES, 150 mM NaCl, pH 7.4) then suspended in 0.5 mL of buffer and [$^3$H]-GR65630 added at a concentration of $3.5 \times 10^{-10}$ M. An initial single concentration of $10^{-7}$ M of the test compound was then added. Incubation was carried out at room temperature for 60 minutes at 25° C. then was terminated by rapid removal of the incubation medium. Radioactivity was assessed using liquid scintillation spectrophotometry after exposure to scintillation cocktail for at least three hours. Compounds displaying greater than 75% inhibition of radioligand binding at $10^{-7}$ M were then resubmitted to the above protocol using the following range of test compound concentrations: $10^{-9}$ M, $10^{-8}$ M, $3 \times 10^{-8}$ M, $10^{-7}$ M, $3 \times 10^{-7}$ M and $10^{-6}$ M. Competition curves were then plotted and IC$_{50}$ determinations made using non-linear regression analysis. Ki values were then calculated from the Cheng-Prusoff equation. In all of the above binding studies the non-specific determinant was MDL-72222 (1.0 µM).

Compound Affinity for the Human 5-HT$_3$ Receptor (Assay B)

The relative affinity of the various compounds for the human 5-HT$_3$ receptor was measured in a radioligand binding assay, using a scintillation proximity assay (SPA) format. Test compounds were dissolved to 10 mM in 100% DMSO, then serially diluted at 10× assay concentrations in 100% DMSO in 96-well polypropylene plates and further diluted to 4× assay concentrations with the assay buffer. Samples were incubated in 50 mM Tris-HCl, pH 7.5, 3 mM MgCl$_2$, 1 mM EDTA and 10% DMSO with 10 nM [9-methyl-$^3$H]BRL-43694 (Perkin Elmer), 3 µg of human 5-HT$_3$ receptor membranes (Perkin Elmer) and 0.5 mg/mL SPA beads (WGA PVT, Amersham Biosciences) in a final volume of 0.2 mL. Binding reactions were set up in wells of PicoPlates-96 (Perkin Elmer) by adding consecutively 50 µL of each competing compound or buffer, SPA beads, the radioligand and 5-HT$_3$ receptor membranes. After 60-min incubation at room temperature on a Nutator mixer, plates were centrifuged for 15 min at 1,500 rpm, followed by incubation in the dark for 30 min. Radioactivity was counted in the TopCount microplate counter (Perkin Elmer) for 5 min. Total binding control contained buffer only; nonspecific binding was determined in the presence of 30 µM MDL-72222. Specific binding was determined by subtracting nonspecific binding from total binding. All experiments were performed in duplicate using ten concentrations of a competing ligand, with ondansetron included as a control in every run. IC$_{50}$ values were determined from specific binding data using XLfit4.1 curve fitting software from IDBS Ltd. K$_i$ values were then calculated from the Cheng-Prusoff equation.

Compound Affinity for the Mouse 5-HT$_3$ Receptor (Assay C)

Compounds were tested by Novoscreen Biosciences Corporation, 7170 Standard Drive, Hanover, Md. in a radioligand binding assay using the mouse 5-HT$_3$ receptor derived from mouse neuroblastoma cells and [$^3$H]-GR65630 (ligand). The non-specific binding determinant was MDL 72222. Compounds were tested at a single concentration of 100 nM in duplicate. Percent inhibition is reported. In order to evaluate the relative affinity of the various compounds for the 5-HT$_3$ receptor, N1E-155 cell lines were developed to express the target protein. For binding, these cells were homogenized, centrifuged and washed with buffer (20 mM HEPES, 150 mM NaCl, pH 7.4) then suspended in 0.5 mL of buffer and [$^3$H]-GR65630 added at a concentration of $3.5 \times 10^{-10}$ M. An initial single concentration of $10^{-7}$ M of the test compound was then added. Incubation was carried out at room temperature for 60 minutes at 25° C. then was terminated by rapid removal of the incubation medium. Radioactivity was assessed using liquid scintillation spectrophotometry after exposure to scintillation cocktail for at least three hours. Compounds displaying greater than 75% inhibition of radioligand binding at $10^{-7}$ M were then resubmitted to the above protocol using the following range of test compound concentrations: $10^{-9}$M, $10^{-8}$M, $3 \times 10^{-8}$ M, $10^{-7}$ M, $3 \times 10^{-7}$ M and $10^{-6}$ M. Competition curves were then plotted and IC$_{50}$ determinations made using non-linear regression analysis. Ki values were then calculated from the Cheng-Prusoff equation. In all of the above binding studies the non-specific determinant was MDL-72222 (1.0 µM).

Compound Affinity for the Human 5-HT$_3$Receptor (Assay D)

Compounds were tested by Cerep, Le Bois l'Evéque—B.P. 1—86600 Celle, L'Evescault, France in a radioligand binding assay using the human recombinant 5-HT$_3$ receptor (CHO cells, Hope, A. G., Peters, J. A., Brown, A. M., Lambert, J. J. and Blackburn, T. P. *Brit. J, Pharmacol.*, 1996, 118: 1237-1245) and [$^3$H]BRL 43694 (ligand) with a 90 incubation at 22° C. For the above studies, the non-specific binding determinant was MDL 72222 (10 µM). The IC$_{50}$ values (concentration causing a half-maximal inhibition of control specific binding) and Hill coefficients were determined by non-linear regression analysis of the competition curves using Hill equation curve fitting. The inhibition constants (K$_i$) were calculated from the Cheng Prusoff equation (K$_i$=IC$_{50}$/(1+(L/K$_D$)), where L=concentration of radioligand in the assay, and K$_D$=affinity of the radioligand for the receptor).

In the table below, the assay in which the data were obtained is shown (as A, B, C, or D) along with the data.

| Example | Structure | Mouse % Inhibition @ 100 nM | Human 5HT$_3$ K$_i$ (nM) |
|---|---|---|---|
| 1 | 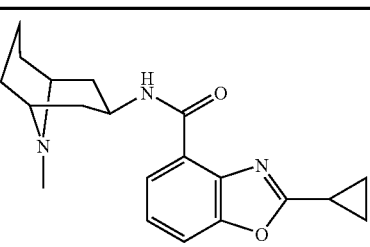 | C<br>96.1 | B<br>4.1 |

-continued

| Example | Structure | Mouse % Inhibition @ 100 nM | Human 5HT$_3$ K$_i$ (nM) |
|---|---|---|---|
| 2 | 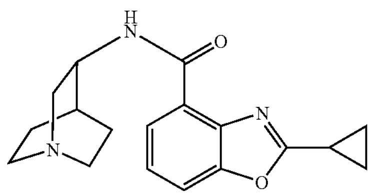 | C 87.7 | B 11 |
| 3 | 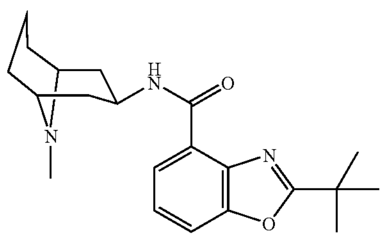 | C 104.2 | D 4.7 |
| 4 | 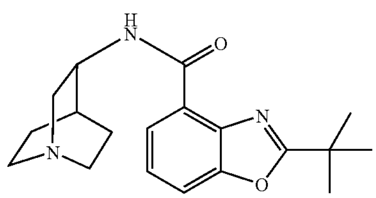 | C 94.3 | D 30 |
| 5 | 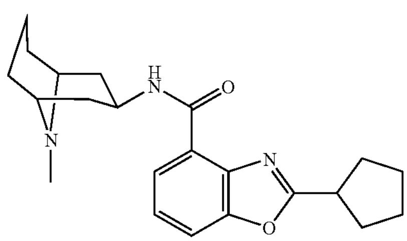 | C 96.2 | A 2.27 |
| 6 | 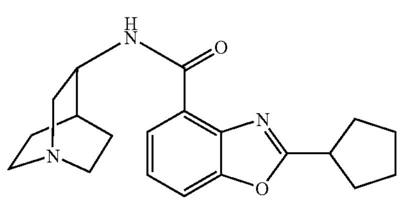 | C 90.2 | |
| 7 | 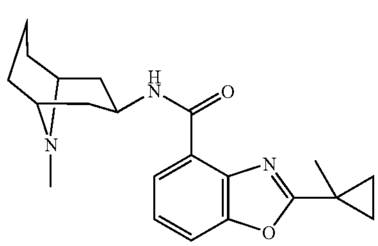 | C 96.7 | D 3.3 |
| 8 | 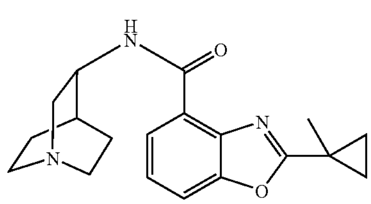 | C 97.6 | D 19 |

| Example | Structure | Mouse % Inhibition @ 100 nM | Human 5HT$_3$ K$_i$ (nM) |
|---------|-----------|------------------------------|--------------------------|
| 9 | 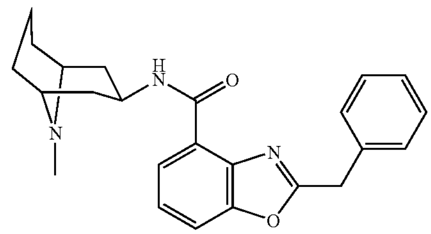 | C 94.7 | D 11 |
| 10 | 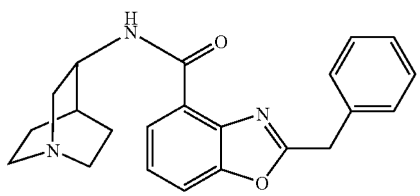 | | D 21 |
| 11 | 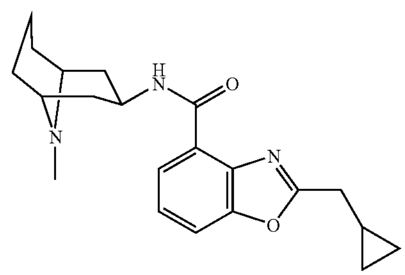 | C 98.6 | D 8.6 |
| 12 | 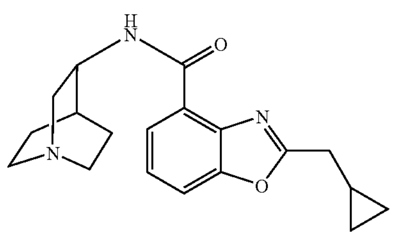 | C 90.6 | D 26 |
| 13 | 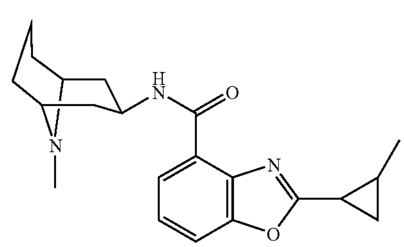 | C 88.1 | A 5.74 |
| 14 | 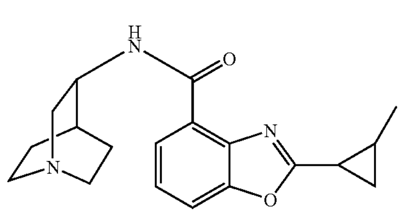 | C 93.6 | |

-continued

| Example | Structure | Mouse % Inhibition @ 100 nM | Human 5HT$_3$ K$_i$ (nM) |
|---|---|---|---|
| 15 | 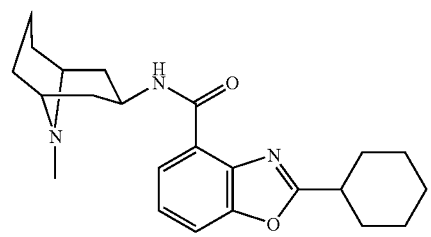 | C 104.9 | |
| 16 | 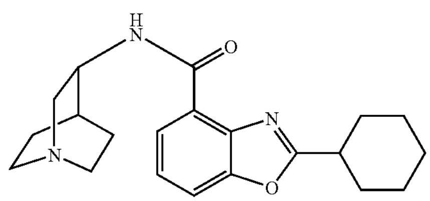 | C 94.1 | |
| 17 | 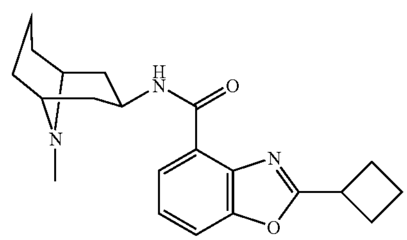 | C 107.7 | D 7 |
| 18 | 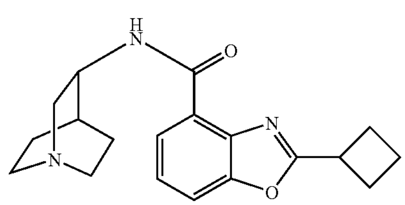 | C 107.7 | D 7 |
| 19 | 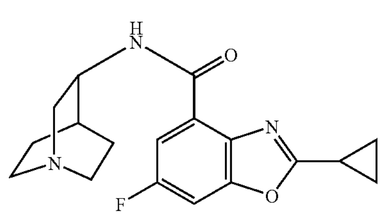 | | D 44 |
| 20 | 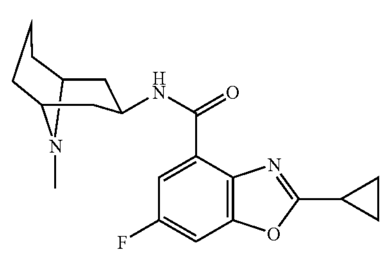 | | D 5.4 |

-continued
| Example | Structure | Mouse % Inhibition @ 100 nM | Human 5HT$_3$ K$_i$ (nM) |
|---|---|---|---|
| 21 | 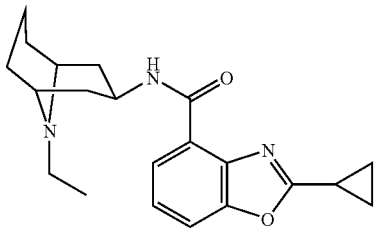 | C 34.9 | |
| 22 | 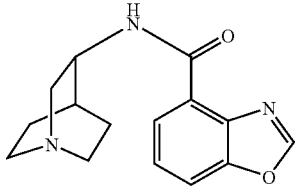 | | A 16.6 |
| 23 | 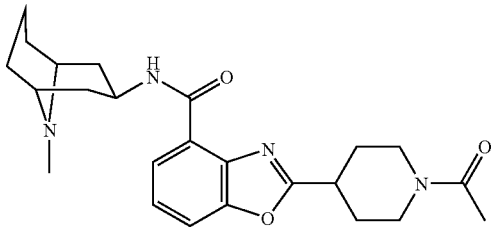 | | A 36.6 |
| 24 | 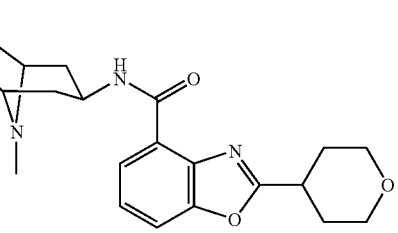 | | A 17.6 |
| 25 | 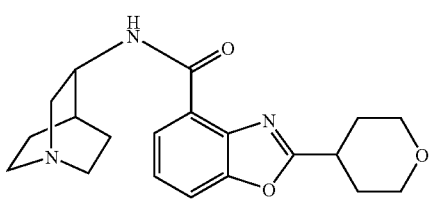 | | B 126 |
| 26 | 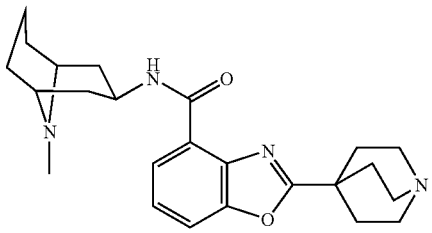 | | B 173 |

-continued
| Example | Structure | Mouse % Inhibition @ 100 nM | Human 5HT$_3$ K$_i$ (nM) |
|---|---|---|---|
| 27 | 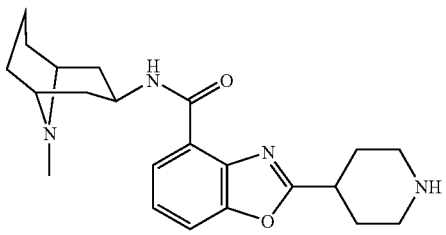 | | B<br>41 |
| 28 | 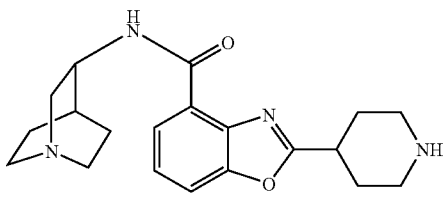 | | B<br>111 |
| 29 | 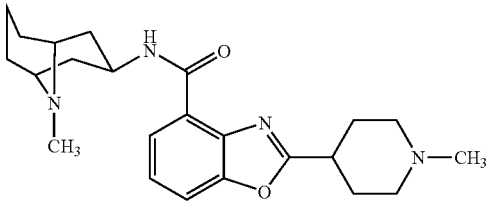 | | B<br>28 |
| 30 | 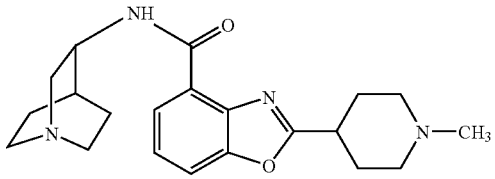 | | B<br>83 |
| 31 | 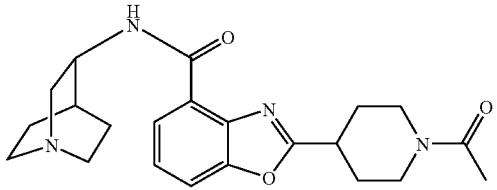 | | B<br>356 |
| 32 | 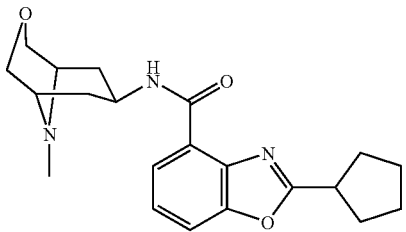 | | B<br>81.9 |

-continued
| Example | Structure | Mouse % Inhibition @ 100 nM | Human 5HT$_3$ K$_i$ (nM) |
|---|---|---|---|
| 33 | 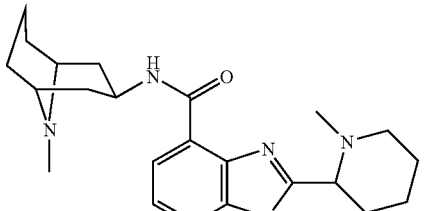 |  | B<br>21.6 |
| 34 | 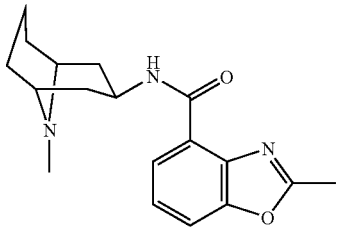 | C<br>79 | D<br>5.5 |
| 35 | 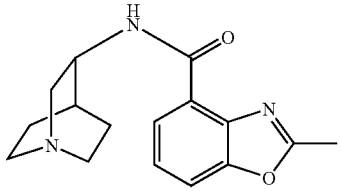 | C<br>83 | D<br>12 |
| 36 | 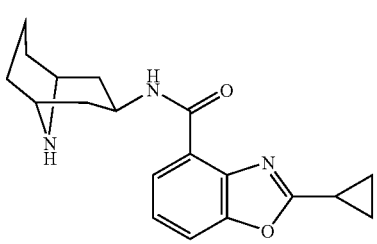 |  | B<br>6.3 |
| 37 | 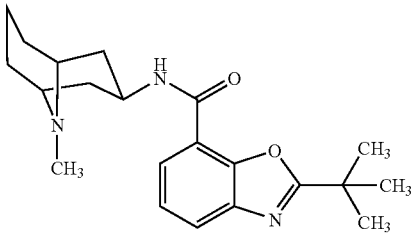 |  | B<br>166 |
| 38 | 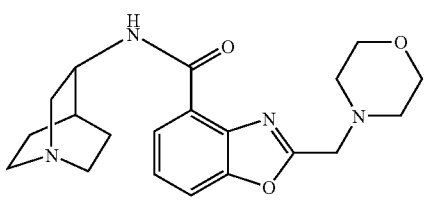 |  | B<br>74% inhibition @ 10 μM |

-continued

| Example | Structure | Mouse % Inhibition @ 100 nM | Human 5HT$_3$ K$_i$ (nM) |
|---|---|---|---|
| 39 | 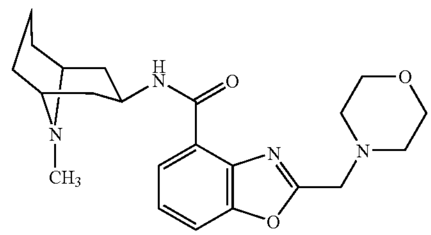 | | B<br>77.1 |
| 40 | 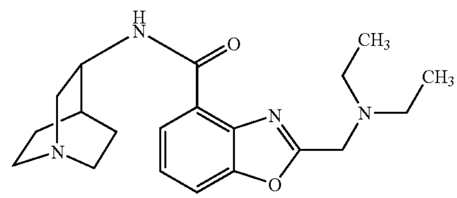 | | B<br>129 |
| 41 | 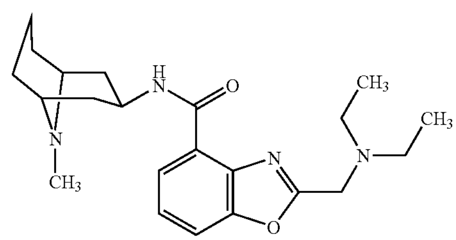 | | B<br>15.3 |
| 42 | 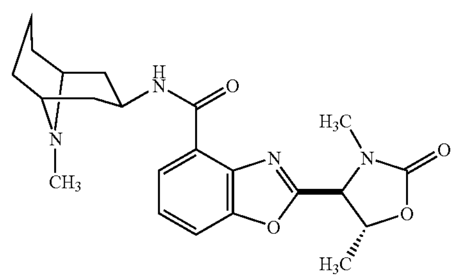 | | B<br>24.9 |

Bezold-Jarisch Assay in vivo. In order to demonstrate functional antagonism of 5-HT$_3$ receptors, compounds 1 and 2 were evaluated for their ability to inhibit serotonin induced bradycardia in vivo in the mouse [Saxena, P. R, and Lawang, A. A comparison of cardiovascular and smooth muscle effects of 5-hydroxytryptamine and 5-carboxamidotryptamine, a selective agonist of 5-HT$_1$ receptors. Arch. Int. Pharmacodyn. 277: 235-252, 1985]. Test substances and vehicle [2% Tween 80] were each administered orally (30 mg/kg) to a group of 5 male or female CD-1 (Crl.) mice each weighing 24±2 g. A dosing volume of 10 mL/kg was used. Sixty minutes later, 5-HT (0.5 mg/kg IV)-induced bradycardia was recorded in pentobarbital (80 mg/kg IP, given 10 minutes before 5-HT)-anesthetized animals. Compounds 1 and 2 exhibited 56% and 80% inhibition, respectively.

The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein. Indeed, the 2006 edition of the Physician's Desk Reference, which is the standard text in the field, employs the term "prevent", or "prevention" not less than 10 times in its description of the indications for palonosetron.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. A simple solid line implies nothing about stereochemistry. For example, a solid line is shown in the graphic for example 2 above, but the compound of the example is actually a single enantiomer of the S configuration and could have been accurately depicted as

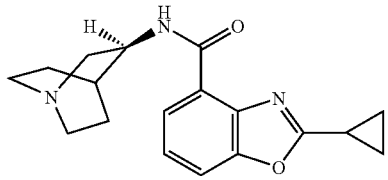

While it may be possible for the compounds of formulas I and II to be administered as the raw chemical, it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or II or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Preferred unit dosage formulations are those containing an effective dose or an appropriate fraction thereof, of the active ingredient.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

It should be understood that in addition to the ingredients particularly mentioned above, the formulations of this invention may include other agents conventional in the art having regard to the type of formulation in question, for example those suitable for oral administration may include flavoring agents.

Although the foregoing invention has been described in some detail for purposes of illustration, it will be readily apparent to one skilled in the art that changes and modifications may be made without departing from the scope of the invention described herein.

What is claimed is:

1. A compound of formula

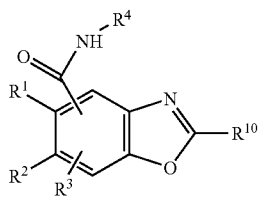

wherein
  $R^1$, $R^2$ and $R^3$ are independently selected from hydrogen, halogen, amino, alkylamino, dialkylamino, acylamino, morpholinyl, —O-loweralkyl, hydroxy, loweralkyl, fluoroloweralkyl, —O-lowerfluoroalkyl, methylenedioxy, ethylenedioxy, alkoxy-loweralkyl and hydroxyloweralkyl;
  $R^4$ is a residue chosen from:
    (i) a saturated nitrogen heterocycle or methyl-substituted saturated nitrogen heterocycle, in which said nitrogen is tertiary, said heterocycle containing at least one 5 or 6-membered ring; and
    (ii) an imidazolylalkyl residue wherein the imidazole of said imidazolylalkyl is optionally substituted with up to three groups chosen from halogen, $(C_1-C_4)$alkyl, substituted $(C_1-C_4)$alkyl and $NH_2$; and
  $R^{10}$ is chosen from the group consisting of
    (i) hydrogen;
    (ii) $(C_1-C_{10})$alkyl;
    (iii) substituted $(C_1-C_{10})$alkyl;
    (iv) saturated C-attached heterocyclyl; and
    (v) substituted, saturated C-attached heterocyclyl.

2. A compound of formula I

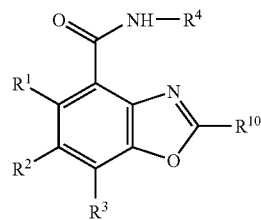

according to claim 1.

3. A compound of formula II

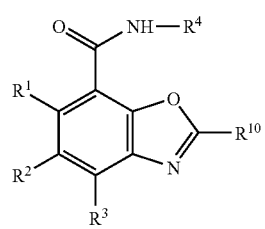

according to claim 1.

4. A compound according to claim 1 wherein $R^4$ is chosen from:

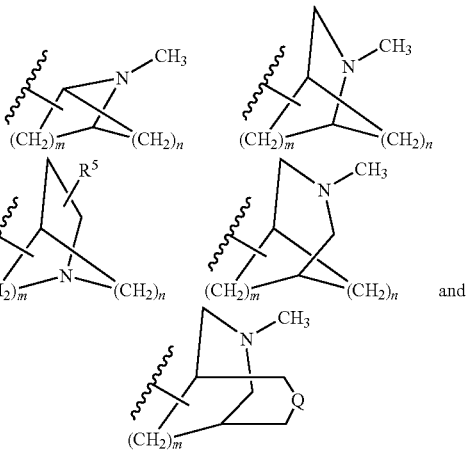

wherein
  m is 1, 2, 3 or 4;
  n is 0, 1, 2, 3 or 4;
  Q is $N(CH_3)$ or —O—; and
  $R^5$ is hydrogen or methyl.

5. A compound according to claim 4, wherein $R^4$ is chosen from quinuclidine, tropane, azabicyclo[3.3.1]nonane, methyl azabicyclo[3.3.1]nonane and dimethyl diazabicyclo[3.3.1]nonane.

6. A compound according to claim 1, wherein $R^1$, $R^2$ and $R^3$ are hydrogen.

7. A compound according to claim 1, wherein one of $R^1$, $R^2$ and $R^3$ is halogen.

8. A compound according to claim 1, wherein $R^{10}$ is chosen from the group consisting of hydrogen and $(C_1$ to $C_3)$alkyl.

9. A compound according to claim 1, wherein $R^{10}$ is chosen from the group consisting of $(C_4$ to $C_{10})$alkyl and substituted $(C_1-C_{10})$alkyl.

10. A compound according to claim 9, wherein $R^{10}$ is chosen from

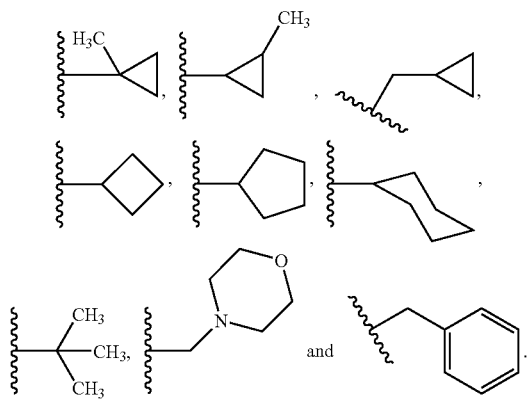

11. A compound according to claim 1, wherein $R^{10}$ is chosen from the group consisting of saturated, C-attached, nitrogenous heterocyclyl; and substituted, saturated, C-attached, nitrogenous heterocyclyl.

12. A compound according to claim 1, wherein $R^{10}$ is chosen from the group consisting of saturated, C-attached, oxygen heterocyclyl; and substituted, saturated, C-attached, oxygen heterocyclyl.

13. A pharmaceutical composition comprising a pharmaceutically acceptable carrier and a therapeutically effective amount of a compound according to claim 1.

14. A pharmaceutical composition according to claim 13 additionally comprising a second antiemetic agent.

15. A pharmaceutical composition according to claim 14, wherein said second antiemetic agent is a neurokinin antagonist.

16. A pharmaceutical composition according to claim 13 additionally comprising a corticosteroid.

* * * * *